US006693178B2

(12) United States Patent
Buchwald et al.

(10) Patent No.: US 6,693,178 B2
(45) Date of Patent: Feb. 17, 2004

(54) PROTECTING GROUPS USEFUL IN THE SYNTHESIS OF POLYSACCHARIDES, NATURAL PRODUCTS, AND COMBINATORIAL LIBRARIES

(75) Inventors: Stephen L. Buchwald, Newton, MA (US); Obadiah J. Plante, Beverly, MA (US); Peter H. Seeberger, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 10/146,711

(22) Filed: May 15, 2002

(65) Prior Publication Data

US 2003/0181690 A1 Sep. 25, 2003

Related U.S. Application Data

(62) Division of application No. 09/717,197, filed on Nov. 21, 2000, now Pat. No. 6,426,421.
(60) Provisional application No. 60/167,302, filed on Nov. 24, 1999.

(51) Int. Cl.$^7$ .......................... C07H 17/00; C07H 15/00
(52) U.S. Cl. ........................... 536/4.1; 536/18.4; 536/8; 549/356; 549/416
(58) Field of Search ........................... 536/4.1, 8, 18.4; 549/356, 416; 570/182

(56) References Cited

U.S. PATENT DOCUMENTS

| | | | |
|---|---|---|---|
| 4,534,785 A | * 8/1985 | Loh | 71/88 |
| 4,675,392 A | 6/1987 | Dahmen et al. | 536/17.6 |
| 4,818,816 A | 4/1989 | Petitou et al. | 536/55.2 |
| 5,094,848 A | 3/1992 | Brixner | 424/85.91 |
| 5,221,736 A | 6/1993 | Coolidge et al. | 536/25.31 |
| 5,464,759 A | 11/1995 | Coolidge et al. | 435/91.2 |
| 5,470,949 A | 11/1995 | Polt | 530/322 |
| 5,576,460 A | 11/1996 | Buchwald et al. | 564/386 |
| 5,587,474 A | 12/1996 | Kondo et al. | 540/350 |
| 5,616,698 A | 4/1997 | Krepinsky et al. | 536/18.6 |
| 5,767,254 A | 6/1998 | Polt | 536/17.2 |
| 5,777,077 A | 7/1998 | Albericio et al. | 530/335 |
| 5,817,877 A | 10/1998 | Hartwig et al. | 564/399 |
| 5,837,866 A | 11/1998 | Magda et al. | 540/145 |
| 5,840,485 A | 11/1998 | Lebl et al. | 435/6 |
| 5,847,166 A | 12/1998 | Buchwald et al. | 549/355 |
| 5,861,351 A | 1/1999 | Albericio et al. | 502/150 |
| 5,874,532 A | 2/1999 | Pieken et al. | 530/338 |
| 5,977,361 A | 11/1999 | Hartwig et al. | 544/264 |
| 6,001,966 A | 12/1999 | Pieken et al. | 530/338 |
| 6,090,912 A | 7/2000 | Lebl et al. | 530/300 |
| 6,166,226 A | 12/2000 | Buchwald et al. | 549/355 |

FOREIGN PATENT DOCUMENTS

| | | |
|---|---|---|
| EP | 0 337 920 B1 | 4/1989 |
| WO | WO 00/20428 | 4/2000 |

OTHER PUBLICATIONS

Martin, O.R. et al. : An efficient synthesis of partially protected alpha–D–ribofuranosides from D–ribose by way of a unique selective debenzylation reaction. J. Org. Chem. vol. 52, pp. 2922–2925, 1987.*
Koto, S. et al. : Some 2,3,4,6–tetra–O–(p–chlorobenzyl)–alpha–D–hexopyranoses. Carbohyd. Res. vol. 87, pp. 294–296, 1980.*
Kong, F. et al. : Improved synthesis of substituted 2,6–dioxabicyclo[3.1.1]heptanes. Carbohyd. Res. vol. 112, pp. 141–147, 1983.*
Fukase et al.; "Novel Oxidatively Removable Protecting Groups and Linkers for Solid–phase Synthesis of Oligosaccharides", Molecular Diversity, 2: 182–188, (1996).
Hartwig F. John; "Transition Metal Catalyzed Synthesis of Arylamines and Aryl Ethers from Aryl Halides and Triflates: Scope and Mechanism", Angew. Chem. Int. Ed. 37:2046–2067, (1998).
Koto et al.; "Some 2,3,4, 6–tetra–0–(p–chlorobenzyl)–α–D–hexopyranoses", Carobhydrate Research, 87: 294–296, (1980).
Kovalainen et al.; "Synthesis and Vitro Pharmacology of a Series of New Chiral Histamine H$_3$–Receptor Ligands: 2–(R and S)–Amino–3–(1H–Imidazol–4(5)–yl)Propyl Ether Derivatives", J. Med. Chem. 42: 1193–1202, (1999).
Nametz, Goerner; "p–Bromobenzyl Chloride", J. Am. Chem. Soc. 73: 2940, (1951).
Patai, Weizmann; "p–Bromobenzyl Bromide", J. Am. Chem. Soc. , 68:150 (1946).
Plante et al.; Halobenzyl Ethers as Protecting Group for Organic Synthesis), J. Am. Chem. Soc. 122: 7148–7149, (2000).
Pohl and Kiessling; "Para–Chlorobenzyl Protecting Groups As Stabilizers of the Glycosidic Linkage: Synthesis of the 3'–0–Sulfate Lewis X Trisaccharide", Tetrahedron Letters 38(40): 6985–6988, (1997).
Püschl et al.; "Solution Phase Synthesis of Dithymine Phosphorothioate by a Phosphotriester Method Using New S–Protecting Groups", Nucleosides & Nucleotides, 16(1&2): 145–158 (1997).

(List continued on next page.)

Primary Examiner—Charanjit S. Aulakh
(74) Attorney, Agent, or Firm—Dana M. Gordon; Foley Hoag LLP

(57) ABSTRACT

One aspect of the present invention relates to optionally substituted halogenated benzyl halides and the like. These compounds are useful as halogenated benzyl ether-based protecting groups for a variety of functional groups. Another aspect of the present invention relates to use of said protecting groups in an orthogonal protecting group strategy for the synthesis of complex molecules that comprise a number of suitable functional groups. Another aspect of the present invention relates to saccharides bearing various arrays of protecting groups of the present invention. Another aspect of the present invention relates to a method of synthesizing an oligosaccharide or glycoconjugate, comprising the steps of: using a saccharide bearing at least one protecting group of the present invention to glycosylate a second molecule to give a product comprising said saccharide; and removing a protecting group of the present invention from said product.

10 Claims, 9 Drawing Sheets

OTHER PUBLICATIONS

Yamashiro Donald; "Protection of Aspartic Acid, Serine, and Threonine in Solid–Phase Peptide Synthesis", J. Org. Chem. 42(3): 523–525, (1977).

"Catalog Handbook of Fine Chemicals", 1996–1997, Aldrich, Nederland, p. 220, (1996); XP–002164979.

International Search Report, Completed on Apr. 20, 2001 and mailed on Jun. 15, 2001.

Wu, X. et al.; "Synthesis, Crystalline Structure, Conformational Analysis, and Azidolysis of Methyl 2,3–Anhydro–α–D–Manno–and–allo–pyranoside p–bromobenzyl Ethers", Carboh. Res. 235: 163–178, (1992).

Wu, E. et al.; "Synthesis and Conformational Analysis of Substituted 2,6–Dioxabicyclo(3.1.1)Heptanes: 1,3–Anhydro–2,4–Di–O–Benzyl–And–2,4–Di–O–(p–Bromobenzyl)–β–1–Rhamnopyranose", Carboh. Res. 161:235–246, (1987).

* cited by examiner

Figure 6

*Pd Catalyzed Amination of Halogenated Benzyl Ether Protecting Groups*

| Halide | Amine | Product | | Isolated Yield (%) |
|---|---|---|---|---|
| 2 | H$_2$N-Bn | Sugar-O-C$_6$H$_4$-NHBn | 16 | 91 |
| | Me-NH-Ph | Sugar-O-C$_6$H$_4$-N(Me)Ph | 17 | 96 |
| | H$_2$N-n-Hex | Sugar-O-C$_6$H$_4$-NH-n-Hex | 18 | 78 |
| 3 | Me-NH-Ph | 17 | | 89 |
| | HN(morpholine) | Sugar-O-C$_6$H$_4$-N(morpholine) | 19 | 95 |
| 4 | H$_2$N-Bn | Sugar-O-CH$_2$-C$_6$H$_4$-NHBn (ortho) | 20 | 76 |

*Halides 2, 3, and 4 are depicted in Figure 1.*

Figure 7

Cleavage of Aminated Benzyl Ether Protecting Groups

| Amine | Activator | Time | Yield |
|---|---|---|---|
| Sugar-O—⟨⟩—NHBn  16 | TiCl$_4$ | 5 min | 100 |
|  | SnCl$_4$ | 5 min | 100 |
|  | ZnCl$_2$ | 16 h | NR |
|  | TMSOTf | 1 h | decomp |
|  | NaOMe | 16 h | NR |
|  | DDQ | 30 min | ~25 |
|  | CAN | 30 min | ~75 |
| Sugar-O—⟨⟩—N(Me)Ph  17 | TiCl$_4$ | 5 min | 100 |
|  | SnCl$_4$ | 5 min | 100 |
|  | ZnCl$_2$ | 30 min | 100 |
| Sugar-O—⟨⟩—NH-n-Hex  18 | TiCl$_4$ | 5 min | ~75 |
|  | ZnCl$_2$ | 16 h | NR |
| 19 | TiCl$_4$ | 5 min | ~75 |
| BnHN—⟨⟩—CH$_2$-O-Sugar  20 | TiCl$_4$ | 5 min | 100 |
|  | SnCl$_4$ | 16 h | NR |
|  | ZnCl$_2$ | 16 h | NR |

*Compound 19 is depicted in Figure 6.*

Synthesis of 10 and 19

Synthesis of 20-22

Synthesis of 23

Synthesis of 24

PROTECTING GROUPS USEFUL IN THE SYNTHESIS OF POLYSACCHARIDES, NATURAL PRODUCTS, AND COMBINATORIAL LIBRARIES

RELATED APPLICATIONS

This application is a divisional of U.S. patent application Ser. No. 09/717,197, filed Nov. 21, 2000 now U.S. Pat. No. 6,426,421; which claims the benefit of the priority date of U.S. Provisional Patent Application Ser. No. 60/167,302, filed Nov. 24, 1999.

GOVERNMENT SUPPORT

This invention was made with support provided by the National Institutes of Health (Grant Number GM 58160). Therefore, the government has certain rights in the invention.

BACKGROUND OF THE INVENTION

The differential protection of functional groups of similar reactivity is a major challenge for the synthesis of complex natural products. The task of distinguishing specific hydroxyl and amino functionalities becomes particularly daunting in carbohydrate chemistry when highly branched structures call for several selectively removable masking groups. Over the years a host of protecting groups has been introduced, each making use of the unique reactivity of the particular masking moiety. Greene, T. W.; Wuts, P. G. M. *Protective Groups in Organic Synthesis*; John Wiley & Sons; New York, 1999. Traditionally, benzyl ethers have been employed for 'permanent' protection and are removed during the late stages of the synthesis, while ester moieties and silyl ethers are used to 'temporarily' mask hydroxyl groups to be unveiled during the synthesis. Orthogonality of protecting groups, or the ability to remove one particular masking entity without affecting the others, is a key issue for synthetic planning and experimental execution.

The reactivity of benzyl ethers has been tuned by using substituted benzyl ether protecting groups which could be selectively removed in the presence of unsubstituted benzyl ethers. These substituted benzyl ethers were generally less stable to reaction conditions than unsubstituted benzyl ethers. Greene, T. W.; Wuts, P. G. M. *Protective Groups in Organic Synthesis*; John Wiley & Sons; New York, 1999, p 86–113. The 4-O-methoxy benzyl group (PMB) has found frequent applications in natural product synthesis since it can be cleaved oxidatively thus sparing most other protective groups. Greene, T. W.; Wuts, P. G. M. *Protective Groups in Organic Synthesis*; John Wiley & Sons; New York, 1999, p 86–91. The acid sensitivity of this group has somewhat restricted its synthetic utility. More recently, other 4-O-substituted benzyl ethers containing acetate and silyl substituents have been reported. Jobron, L.; Hindsgaul, O. *J. Am. Chem. Soc.* 1999, 121, 5835–5836. While these benzyl ether groups do not require palladium catalyzed hydrogenation for their removal, they necessitate treatment with base or fluoride respectively, followed by oxidative cleavage. These deprotection protocols forfeit compatibility of these 4-substituted benzyl ethers with ester, silyl, or PMB protecting groups.

SUMMARY OF THE INVENTION

One aspect of the present invention relates to optionally substituted halogenated benzyl halides and the like. These compounds are useful as halogenated benzyl ether-based protecting groups for a variety of functional groups, e.g., alcohols, thiols, amines, carboxylic acids, and phosphoric acids. The corresponding protected functional groups are stable to a wide range of reaction conditions; however, they can be removed readily using methods of the present invention.

Certain methods of the present invention pertain to the selective removal of the benzyl ether-based protecting groups of the present invention. These methods comprise the steps of: replacing the halide moiety of the protecting group with a heteroatomic group, e.g., an alcohol, thiol, or amine, via transition metal catalysis to give a second benzyl ether-based protecting group (incorporating said heteroatomic group); and removing said second benzyl ether-based protecting group by treatment with a Lewis acid or oxidizing agent.

Another aspect of the present invention relates to use of the protecting groups and methods in concert to develop and exploit an orthogonal protecting group strategy for the synthesis of complex molecules, e.g., natural products, oligosaccharides, or combinatorial libraries of one or both, comprising a number of functional groups selected from the group comprising alcohols, thiols, amines, carboxylic acids, and phosphoric acids.

Another aspect of the present invention relates to mono- and oligo-saccharides bearing various arrays of protecting groups of the present invention. These compounds will be useful to synthetic, medicinal, and process chemists pursuing the synthesis of oligo- and poly-saccharides and glycoconjugates. Furthermore, another aspect of the present invention relates to a method of synthesizing an oligosaccharide or glycoconjugate, comprising the steps of: using a mono- or oligo-saccharide bearing at least one protecting group of the present invention to glycosylate a molecule to give a product comprising said mono- or oligo-saccharide; and removing at least one protecting group of the present invention from said product.

BRIEF DESCRIPTION OF THE FIGURES

FIG. 6 presents the results of palladium-catalyzed aminations of halogenated benzyl ethers.

FIG. 7 presents the results of deprotections of hydroxyl groups protected with aminated benzyl ethers.

DETAILED DESCRIPTION OF THE INVENTION

Figure 1:
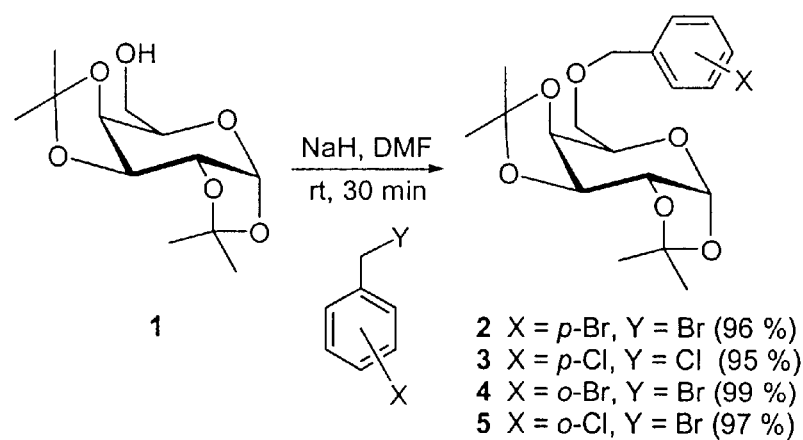
FIG. 1 depicts the preparation of four galactopyranosides bearing a protecting group of the present invention.

Substituted benzyl ether protecting groups which could be selectively and mildly removed in the presence of other substituted benzyl ethers would greatly enrich the synthetic arsenal. The synthesis of highly branched carbohydrates and combinatorial libraries of oligosaccharides would particularly benefit from such developments. The 4-methoxybenzyl group (PMB) has found frequent applications in carbohydrate chemistry because it can be removed oxidatively. However, the acid sensitivity of this group has restricted its synthetic utility. More recently, other 4-O-substituted benzyl ethers containing acetate and silyl substituents have been reported, but require treatment with base or fluoride respectively, followed by oxidative cleavage. Accordingly, these protocols are not compatible with ester, silyl, or PMB protecting groups.

Ideally, a set of substituted benzyl ethers that are equally or more stable than unsubstituted benzyl ethers and which may be removed selectively under mild conditions without affecting silyl ether and ester protecting groups is envisioned. Such benzyl ether based protecting groups would only minimally affect the reactivity of fully protected glycosylating agents therefore ensuring reproducibility of glycosylating reactions independent of the protecting group ensemble used. When contemplating the virtues of such novel protecting group concepts, we considered the stable halogenated benzyl ethers, which could be readily converted into aryl amines by palladium catalyzed amination. The resulting aryl amines in turn were expected to be receptive to cleavage by a variety of conditions.

The catalytic amination of aryl halides represents a mild alternative to the classical methods of C—N bond formation. Catalysts to affect the cross-coupling of amines with aryl halides have been developed and a wide range of compounds not previously accessible are now readily available. Yang, B. H.; Buchwald, S. L. *J. Organomet. Chem.* 1999, 576, 125–146; and Hartwig, J. F. *Angew. Chem. Int. Ed.* 1998, 37, 2046–2067. Here we describe the use of palladium catalyzed aminations to convert stable halogenated benzyl ethers into substituted aryl amines which can be cleaved by Lewis acids or under oxidative conditions. Selective removal of different substituted ethers in the presence of silyl ether, pivaloyl ester, and PMB ether groups was readily achieved. These novel protecting groups should find wide application in the synthesis of carbohydrates, natural products, and combinatorial libraries.

Halogenated benzyl ethers are protecting groups which are stable to a range of reaction conditions. The conversion of the aryl halide moiety of a halogenated benzyl ether into the corresponding aminobenzyl ether drastically changes the reactivity of the benzyl ether moiety. The resulting amino benzyl ethers are labile to cleavage by Lewis acids, while benzyl ethers are unreactive under these conditions. Selective conversion of halogenated benzyl ethers into compounds which may be cleaved under mild conditions holds enormous potential for many applications. Here, we describe a set of halogenated benzyl ether protecting groups for hydroxyl, amine, carboxylate and phosphate functionalities which may be selectively removed by a two-step method, comprising the steps of palladium catalyzed amination, followed by treatment with a Lewis acid or oxidation.

The benzyl ether based protecting groups described in this disclosure present an entire set of novel protective groups which may be selectively removed in the presence of other masking groups. Traditionally, benzyl ether groups have been used as permanent blocking groups that were removed only at the end of the synthesis. Now, halogenated benzyl ethers can be used as temporary protecting groups which may be selectively deprotected. These groups are of particular importance in carbohydrate chemistry where a multitude of hydroxyl and amine functionalities has to be distinguished in the assembly of branched structures. Currently available protecting groups limit the degree of orthogonality while the groups described here add several alternatives. Other areas of use will be found in the preparation of complex natural products and the preparation of combinatorial libraries, particularly carbohydrate libraries.

Protecting groups are commonly used in the preparation of a multitude of molecules of pharmaceutical importance. The new protecting groups may greatly facilitate the synthesis of multifunctional molecules, in particular complex carbohydrates. This disclosure will have impact on the synthesis of combinatorial carbohydrate libraries that will be used to identify ligands for a host of receptors of biomedical importance.

Protection of Hydroxyl Groups

Protection of hydroxyl functionalities with the different substituted benzyl ether protecting groups may be achieved using standard conditions, such as a benzyl halide and sodium hydride, or a benzyl trichloroacetimidate with activation by TMSOTf.

Scheme 1.
Method for Protecting Hydroxyl Moieties as Halogenated Benzyl Ethers

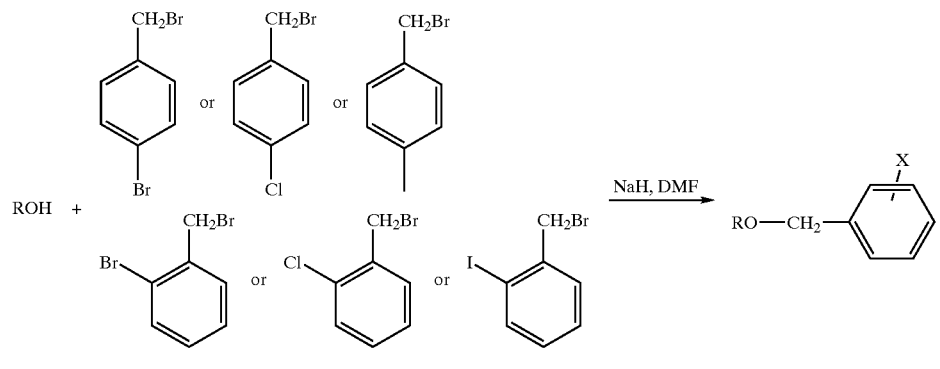

The reactivity of 4-bromo-, 4-chloro-, 2-bromo-, and 2-chlorobenzyl groups toward palladium catalyzed coupling with primary and secondary amines varies significantly. Thus, the selective formation of N-aryl amines which can in turn be cleaved in the presence of benzyl ethers is possible and allows for the development of an orthogonal set of benzyl ether protecting groups. Cleavage of these benzyl ethers is carried out by a two step process. First, coupling of the aryl bromide or chloride with a primary or secondary amine in the presence of palladium, a ligand (e.g. BINAP) and a base (sodium t-butoxide, potassium phosphate) will furnish a variety of aryl amines. Different amines, including benzylamine, aniline, N-methylaniline, and hexylamine have been used in this function and were explored for coupling efficiency and ease of the following cleavage step. Depending upon the amine employed, cleavage of the resulting aryl amine is achieved by reaction with Lewis acids including $ZnCl_2$, $MgBr_2$, TMSOTf, $SnCl_4$, and $TiCl_4$, or oxidative conditions (CAN, DDQ).

Scheme 2.
Two-Step Method for Removal of Halogenated Benzyl Ethers

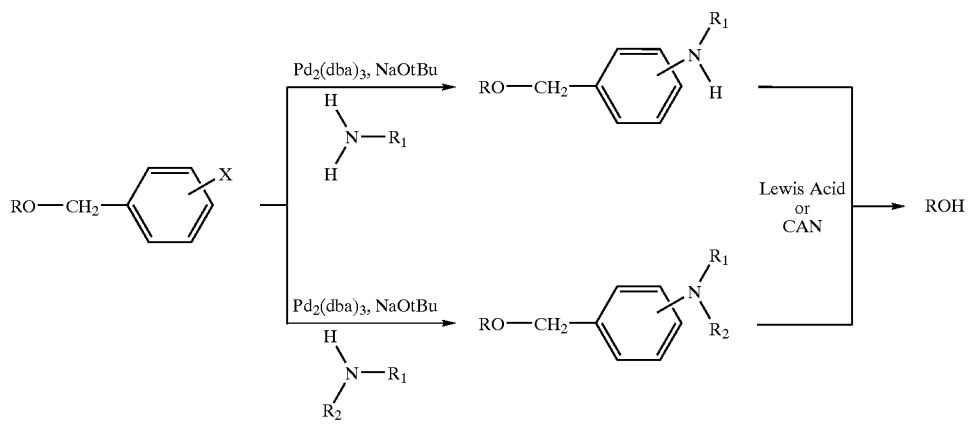

The differences in reactivity between aryl bromides and aryl chlorides (bromides are more reactive than chlorides), and between para and ortho substituted isomeric aryl halides (para is more reactive than ortho), allow for the selective removal of the halogenated benzyl ether protecting groups in the orders indicated in Scheme 3. The utility of differential protection reaches of course far beyond carbohydrate chemistry. These benzyl ether protecting groups may be used in solution as well as on the solid support.

Scheme 3.
Differentially-Protected Monosaccharides for Carbohydrate Synthesis

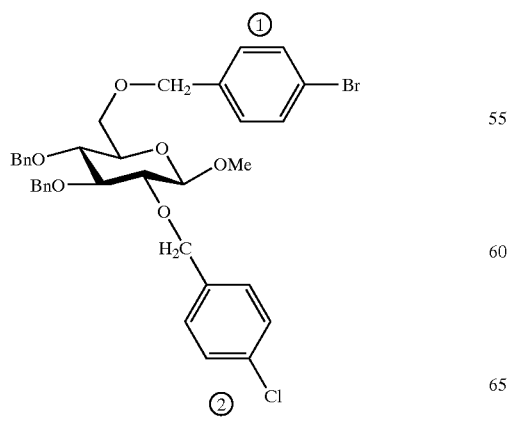

-continued

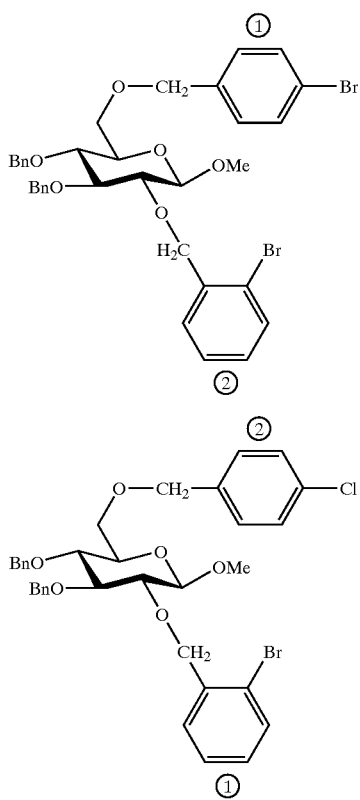

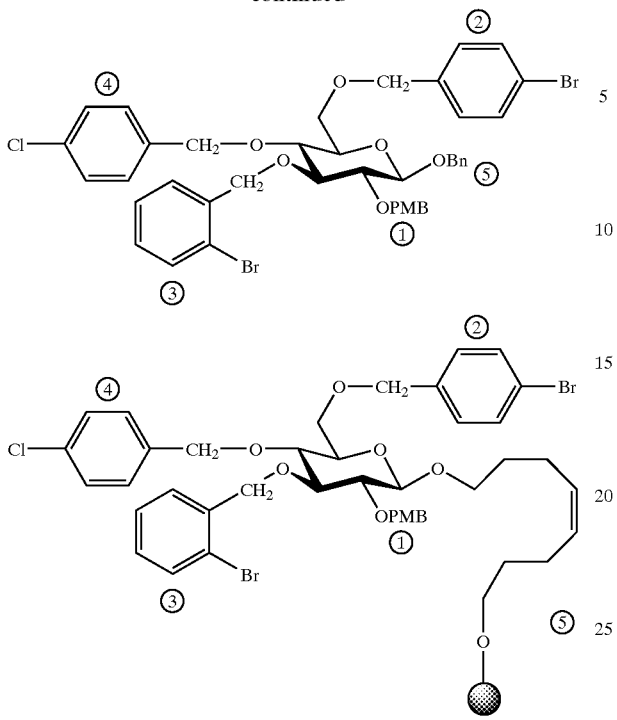

Protection of Amino Groups

Using a similar set of halogenated benzyl-based protecting groups, an orthogonal set of amine protecting groups has been developed. The carbyloxybenzoyl (Cbz) protecting group has been frequently used in the protection of amine functionalities since it is readily applied, stable to a wide range of reaction conditions and removed either with strong base or hydrogenation. Halogenated benzyl ether carbamate protecting groups are even more acid stable than the Cbz group. Installation of the novel amine protecting groups is very straightforward. Reaction of the halogenated benzyl alcohols with triphosgene results in formation of the corresponding chloroformates. These chloroformates react readily with amine functionalities to furnish the carbamates which are stable to a wide range of conditions but may be removed selectively using the Pd-catalyzed amination conditions outlined above.

Scheme 4.
Method for the Protection of Amines as Halogenated Benzyl Carbamates

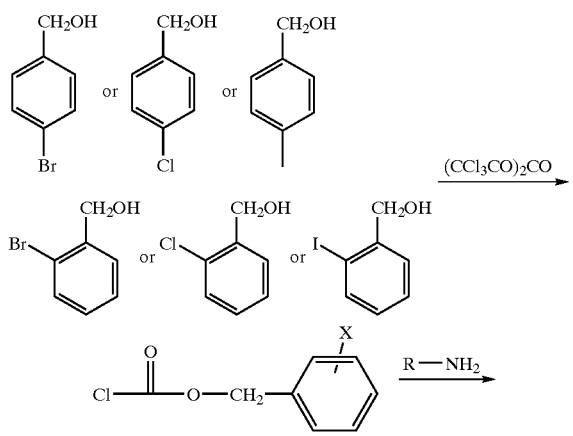

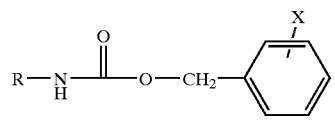

Cleavage of the halogen benzylcarbamate protecting groups was achieved as described for the benzyl ether protecting groups by palladium catalyzed amination followed by treatment with a Lewis acid or oxidative conditions. Selective cleavage of specific benzyl carbamates can also be achieved by exploiting the relative reactivities described above.

Alternatively, mono- and di-halobenzylamines may serve as the protected form of the amine functionality. Removal of these groups may be carried out as described for the carbamates and benzyl ether protecting groups.

Scheme 5.
Method for the Protection of Amines as Halogenated Benzyl Amines

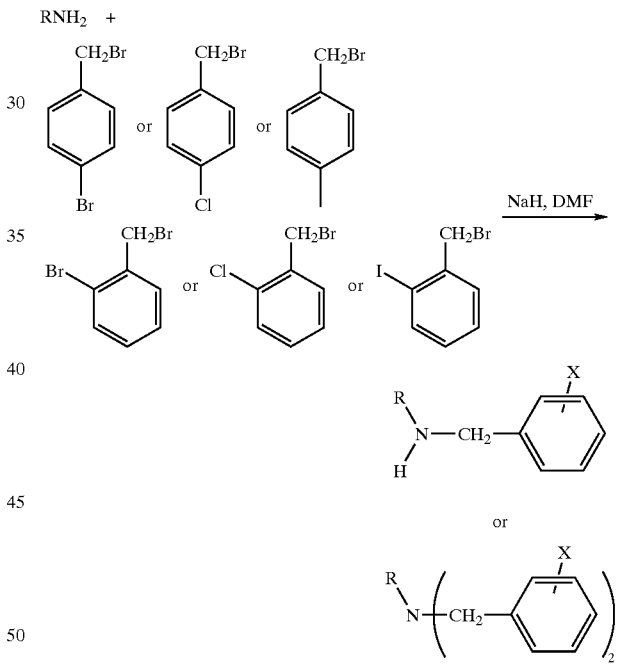

Protection of Carboxylate and Phosphate Groups

Halogenated benzyl ethers may also serve as protecting groups for the masking of carboxylates and phosphate esters. These novel groups hold particular potential for the synthesis of oligonucleotides and their analogs. Although chlorobenzyl phosphates esters have been used previously as phosphate protecting groups, they required hydrogenation for removal. Palladium catalyzed amination followed by treatment with Lewis acids provides now a more selective mode for cleavage of the carboxylate ester and phosphate ester protecting groups.

Scheme 6.
Method for the Deprotection of Halogenated Benzyl Phosphates

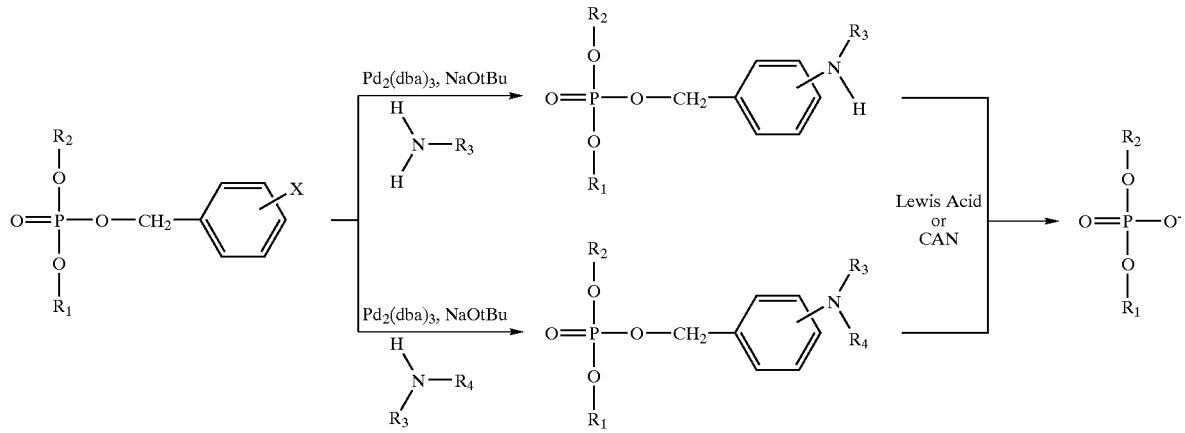

Overview of Experimental Results

Figure 2:
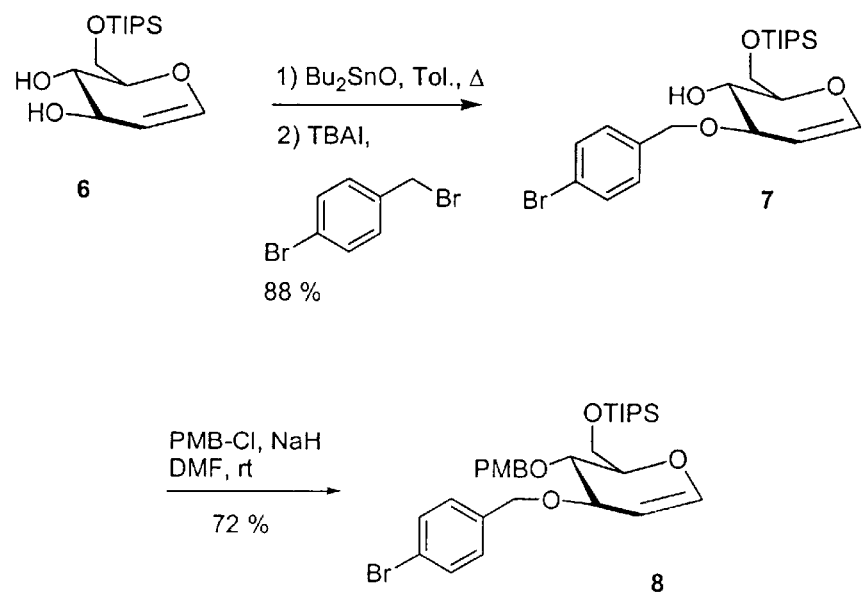
FIG. 2 depicts the preparation of an orthogonally-protected D-glucal, comprising a protecting group of the present invention.
Figure 3:
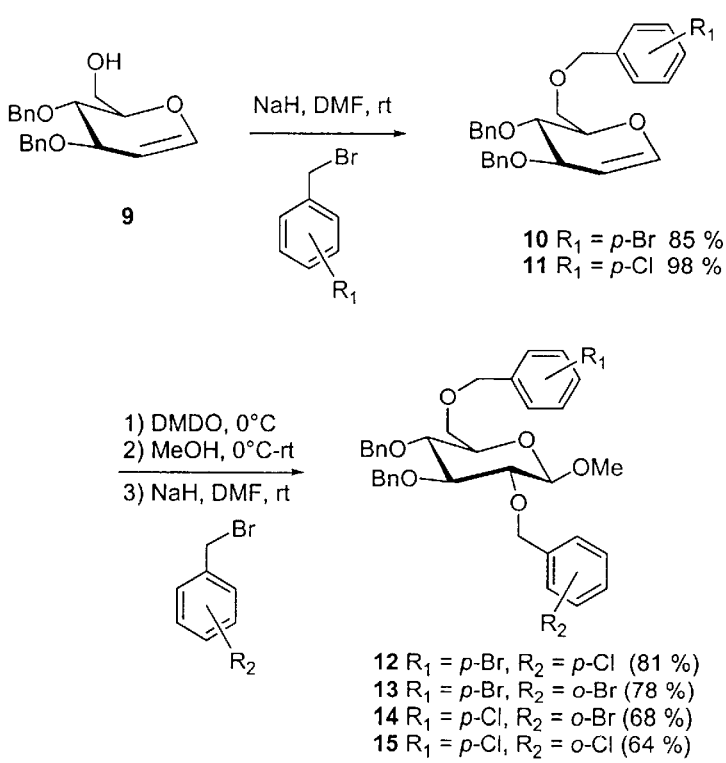
FIG. 3 depicts the use of the protecting groups of the present invention in the preparation of an orthogonally-protected D-glucal, and its use as a glycosylating agent.

The introduction of halogenated benzyl ether protecting groups is achieved by reaction of the hydroxyl group with the corresponding benzyl chloride or benzyl bromide in the presence of sodium hydride (FIG. 1). As expected, the protection reactions were straightforward and high yielding. Selective introduction of the 4-bromobenzyl ether protecting group in the C3 position of 6-TIPS glucal 6 was achieved via the stannyl ether to fashion glucal 7. Monosaccharide 7 was readily transformed into protected glucal 8 by reaction with PMB-chloride (FIG. 2). Furthermore, a series of methyl glucosides 12–15 containing different combinations of halogenated benzyl ether protecting groups in the C2 and C6 position was prepared from 3,4-dibenzyl glucal 9 (FIG. 3).

With a series of protected monosaccharide substrates in hand, palladium catalyzed amination reactions employing different amines were explored (FIG. 6). Following protocols for the efficient amination of aryl bromides developed by Buchwald et al. the PBB protected galactose 2 was coupled with benzylamine, N-methyl aniline and n-hexyl amine. One molpercent $Pd_2(dba)_3$ and a recently developed ligand (o-biphenyl)P(t-Bu)$_2$ (2 mol %) were used as the catalyst system in the presence of sodium tert-butoxide (1.4 equiv). The reactions were carried out at 80° C. for 3 hours or alternatively at room temperature for 16 hours. While both benzylamine and N-methyl aniline gave excellent yields, the coupling with n-hexylamine resulted in the formation of a significant amount of bisarylation product. The 4-chlorobenzyl moiety of galactose 3 could be efficiently N-arylated using the same coupling conditions with N-methylaniline or morpholine. 2-bromobenzyl protected 4 was reacted with benzylamine in good yield to fashion 20.

After protocols for the facile conversion of the stable halogenated benzyl ethers into a variety of aryl amines had been established, conditions to facilitate the cleavage of these amines were explored (FIG. 7). Secondary arylbenzylamine 16 proved surprisingly stable but succumbed readily to strong Lewis acids ($TiCl_4$, $SnCl_4$) and could be cleaved quantitatively in only five minutes. Zinc chloride, TMS triflate, and sodium methoxide failed to cleave 16. Under oxidative conditions cleavage was observed and treatment with cerium (IV) ammonium nitrate revealed 75% of the free alcohol after 30 minutes. The tertiary aryl amine 17 was more labile to cleavage by Lewis acids as it could be quantitatively converted with zinc chloride in 30 minutes. Secondary and tertiary aryl alkyl amines 18 and 19 required titanium tetrachloride for cleavage while other Lewis acids failed entirely to facilitate liberation of the hydroxyl functionality. Ortho substituted aryl benzyl amine 20 exhibited similar reactivity as it could also rapidly be cleaved by treatment with $TiCl_4$, while other Lewis acids did not facilitate the reaction.

Figure 5:
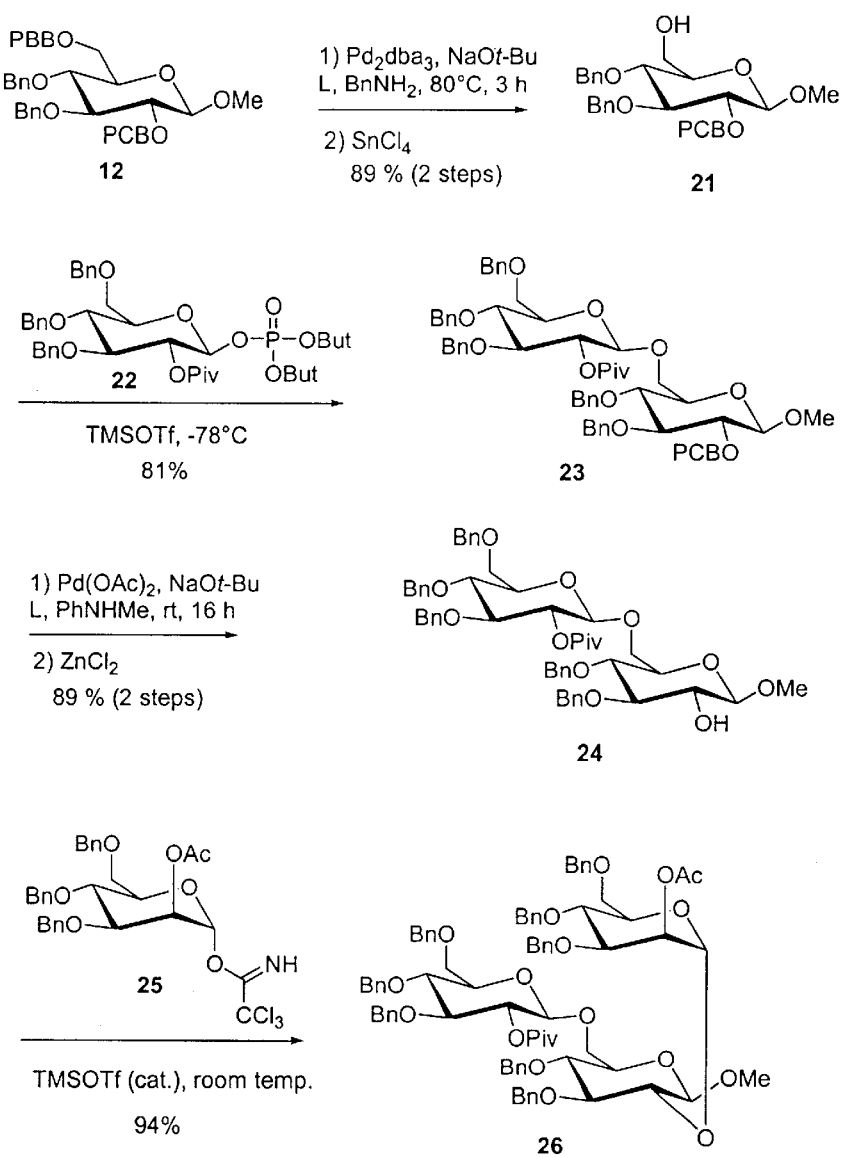
FIG. 5 depicts the synthesis of a trisaccharide using the methods and protecting groups of the present invention.

Orthogonality of benzyl ether protecting groups was a major driving force of our investigation. Due to the significant reactivity differences of aryl bromides and aryl chlorides and ortho- and para-substituted aryl ethers in palladium catalyzed amination reactions we anticipated that the selective amination and thus removal of a specific protecting group in the presence of other halogenated benzyl ethers would be possible. The orthogonality of 4-chlorobenzyl (PBC) and 4-bromobenzyl (PBB) protecting groups was utilized in the construction of a trisaccharide (FIG. 5). Starting from differentially protected monosaccharide 12, the PBB group was selectively removed in 89% yield to expose the C6 hydroxyl functionality without affecting the PCB group on C2. Glycosylation employing glucosyl phosphate 22 yielded 81% of the desired disaccharide 23. Removal of the PCB group by palladium catalyzed amination proceeded smoothly in the presence of the pivaloyl ester to fashion disaccharide glycosyl acceptor 24. Mannosylation using trichloroacetimidate donor 25 furnished trisaccharide 26 in 94% yield. We were also able to demonstrate that the PBB protecting group could be removed in the presence of the 2-bromobenzyl (OBB) masking group. Methyl glycoside 14 was subjected to palladium catalyzed amination with benzylamine and resulted in predominant removal of the PBB group although about 30% of material which had lost the OBB protecting group as well was isolated. Further optimization is expected to yield conditions which will allow for the selective removal of the PBB in the presence of the OBB groups.

To demonstrate the compatibility of the novel benzyl ether protecting groups with other commonly used modes of masking, the PBB group of differentially protected glucal 8 was selectively removed. Neither the silyl ether (TIPS), nor the PMB group were affected by the two step deprotection protocol described and allowed for the liberation of the C3 hydroxyl group in 96% yield.

The concept of halogenated benzyl ether protecting groups disclosed herein is currently being further extended to more highly substituted benzyl ethers thus providing a wide range of selectively removable protecting groups. Halogenated benzyl moieties in the form of carbamates are useful as amine protecting groups and will also serve well for the masking of phosphate and carboxylic acids.

Compounds and Methods of the Invention

One aspect of the present invention relates to optionally substituted halogenated benzyl halides and the like. These compounds have been and may be used as halogenated benzyl ether-based protecting groups for a variety of functional groups, e.g., alcohols, thiols, amines, carboxylic acids, and phosphoric acids. The corresponding protected functional groups are stable to a wide range of reaction conditions; however, they can be removed readily using methods of the present invention.

Certain methods of the present invention pertain to the selective removal of the benzyl ether-based protecting groups of the present invention. These methods comprise the steps of: replacing the halide moiety of the protecting group with a heteroatomic group, e.g., an alcohol, thiol, or amine, via transition metal catalysis to give a second benzyl ether-based protecting group (incorporating said heteroatomic group); and removing said second benzyl ether-based protecting group by treatment with a Lewis acid or oxidizing agent.

Another aspect of the present invention relates to use of the protecting groups and methods in concert to develop and exploit an orthogonal protecting group strategy for the synthesis of complex molecules, e.g., natural products, oligosaccharides, or combinatorial libraries of one or both, comprising a number of functional groups selected from the group comprising alcohols, thiols, amines, carboxylic acids, and phosphoric acids.

Another aspect of the present invention relates to mono- and oligo-saccharides bearing various arrays of protecting groups of the present invention. These compounds will be useful to synthetic, medicinal, and process chemists pursuing the synthesis of oligo- and poly-saccharides and glycoconjugates. Furthermore, another aspect of the present invention relates to a method of synthesizing an oligosaccharide or glycoconjugate, comprising the steps of: using a mono- or oligo-saccharide bearing at least one protecting group of the present invention to glycosylate a molecule to give a product comprising said mono- or oligo-saccharide; and removing at least one protecting group of the present invention from said product.

In certain embodiments, the present invention relates to a compound represented by general structure 50:

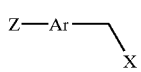

wherein

X represents Cl, Br, I, OTf, OTs, ONf, OMs;

Z represents Cl, Br, or I; and

Ar represents an optionally substituted monocyclic or polycyclic aryl or heteroaryl group, wherein CH$_2$X and Z are bonded to the same aromatic ring of Ar.

In certain embodiments, the compounds of the present invention are represented by 50 and the attendant definitions, wherein Ar represents optionally substituted phenyl.

In certain embodiments, the compounds of the present invention are represented by 50 and the attendant definitions, wherein X represents Cl or Br.

In certain embodiments, the compounds of the present invention are represented by 50 and the attendant definitions, wherein Z represents Cl or Br.

In certain embodiments, the compounds of the present invention are represented by 50 and the attendant definitions, wherein Ar represents optionally substituted phenyl; and X represents Cl or Br.

In certain embodiments, the compounds of the present invention are represented by 50 and the attendant definitions, wherein Ar represents optionally substituted phenyl; and Z represents Cl or Br.

In certain embodiments, the compounds of the present invention are represented by 50 and the attendant definitions, wherein Ar represents optionally substituted phenyl; X represents Cl or Br; and Z represents Cl or Br.

A method of protecting a functional group as depicted in Scheme 51:

Scheme 51

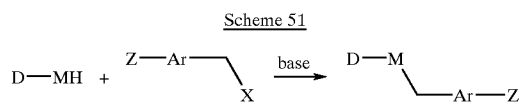

wherein

X represents Cl, Br, I, OTf, OTs, ONf, OMs;

Z represents Cl, Br, or I;

Ar represents an optionally substituted monocyclic or polycyclic aryl or heteroaryl group, wherein CH$_2$X and Z are bonded to the same aromatic ring of Ar;

M represents O, S, or NR;

R represents independently for each occurrence H, alkyl, aryl or heteroaryl;

D represents alkyl, aryl, heteroaryl, pyranosyl, furanosyl, acyl, or (RO)$_2$P(O)—; and base is absent or represents a carbonate, bicarbonate or hydride.

In certain embodiments, the method of the present invention is represented by Scheme 51 and the attendant definitions, wherein M represents O.

In certain embodiments, the method of the present invention is represented by Scheme 51 and the attendant definitions, wherein D represents pyranosyl, furanosyl, acyl, or (RO)$_2$P(O)—.

In certain embodiments, the method of the present invention is represented by Scheme 51 and the attendant definitions, wherein M represents O; and D represents pyranosyl, furanosyl, acyl, or (RO)$_2$P(O)—.

In certain embodiments, the method of the present invention is represented by Scheme 51 and the attendant definitions, wherein base represents a hydride.

In certain embodiments, the method of the present invention is represented by Scheme 51 and the attendant definitions, wherein Ar represents optionally substituted phenyl.

In certain embodiments, the method of the present invention is represented by Scheme 51 and the attendant definitions, wherein X represents Cl or Br.

In certain embodiments, the method of the present invention is represented by Scheme 51 and the attendant definitions, wherein Z represents Cl or Br.

In certain embodiments, the method of the present invention is represented by Scheme 51 and the attendant definitions, wherein Ar represents optionally substituted phenyl; and X represents Cl or Br.

In certain embodiments, the method of the present invention is represented by Scheme 51 and the attendant definitions, wherein Ar represents optionally substituted phenyl; and Z represents Cl or Br.

In certain embodiments, the method of the present invention is represented by Scheme 51 and the attendant definitions, wherein Ar represents optionally substituted phenyl; X represents Cl or Br; and Z represents Cl or Br.

In certain embodiments, the method of the present invention is represented by Scheme 51 and the attendant definitions, wherein Ar represents optionally substituted phenyl; X represents Cl or Br; Z represents Cl or Br; M represents O; and D represents pyranosyl, furanosyl, acyl, or $(RO)_2P(O)$—.

Scheme 52

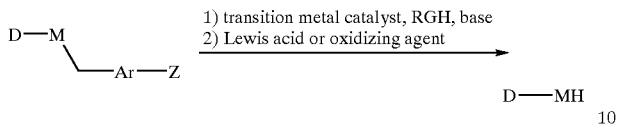

wherein
- Z represents Cl, Br, or I;
- Ar represents an optionally substituted monocyclic or polycyclic aryl or heteroaryl group, wherein $CH_2X$ and Z are bonded to the same aromatic ring of Ar;
- M represents O, S, or NR;
- G represents O, S, or NR;
- R represents independently for each occurrence H, alkyl, aryl or heteroaryl;
- D represents alkyl, aryl, heteroaryl, pyranosyl, furanosyl, acyl, or $(RO)_2P(O)$—; and
- base represents an alkoxide, amide, carbonate, or hydride.

In certain embodiments, the method of the present invention is represented by Scheme 52 and the attendant definitions, wherein G represents NR.

In certain embodiments, the method of the present invention is represented by Scheme 52 and the attendant definitions, wherein M represents O.

In certain embodiments, the method of the present invention is represented by Scheme 52 and the attendant definitions, wherein D represents pyranosyl, furanosyl, acyl, or $(RO)_2P(O)$—.

In certain embodiments, the method of the present invention is represented by Scheme 52 and the attendant definitions, wherein Lewis acid represents a silyl triflate, zinc(II) halide, tin(IV) halide, or Ti(IV) halide; and oxidizing agents is absent.

In certain embodiments, the method of the present invention is represented by Scheme 52 and the attendant definitions, wherein Lewis acid represents trimethylsilyl triflate, zinc(II) chloride, tin(I) chloride, or Ti(IV) chloride; and oxidizing agent is absent.

In certain embodiments, the method of the present invention is represented by Scheme 52 and the attendant definitions, wherein oxidizing agent represents DDQ or CAN; and Lewis acid is absent.

In certain embodiments, the method of the present invention is represented by Scheme 52 and the attendant definitions, wherein G represents NR; and M represents O.

In certain embodiments, the method of the present invention is represented by Scheme 52 and the attendant definitions, wherein G represents NR; M represents O; and D represents pyranosyl, furanosyl, acyl, or $(RO)_2P(O)$—.

In certain embodiments, the method of the present invention is represented by Scheme 52 and the attendant definitions, wherein G represents NR; M represents O; D represents pyranosyl, furanosyl, acyl, or $(RO)_2P(O)$—; Lewis acid represents a silyl triflate, zinc(II) halide, tin(IV) halide, or Ti(IV) halide; and oxidizing agents is absent.

In certain embodiments, the method of the present invention is represented by Scheme 52 and the attendant definitions, wherein G represents NR; M represents O; D represents pyranosyl, furanosyl, acyl, or $(RO)_2P(O)$—; Lewis acid represents trimethylsilyl triflate, zinc(II) chloride, tin(IV) chloride, or Ti(IV) chloride; and oxidizing agent is absent.

In certain embodiments, the method of the present invention is represented by Scheme 52 and the attendant definitions, wherein G represents NR; M represents O; D represents pyranosyl, furanosyl, acyl, or $(RO)_2P(O)$—; oxidizing agent represents DDQ or CAN; and Lewis acid is absent.

In certain embodiments, the present invention relates to a compound represented by general structure 53:

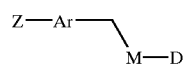

wherein
- D represents alkyl, aryl, heteroaryl, pyranosyl, furanosyl, acyl, or $(RO)_2P(O)$;
- M represents O, S, or NR;
- Z represents Cl, Br, or I; and
- Ar represents an optionally substituted monocyclic or polycyclic aryl or heteroaryl group, wherein $CH_2X$ and Z are bonded to the same aromatic ring of Ar.

In certain embodiments, the compounds of the present invention are represented by 53 and the attendant definitions, wherein Ar represents optionally substituted phenyl.

In certain embodiments, the compounds of the present invention are represented by 53 and the attendant definitions, wherein M represents O.

In certain embodiments, the compounds of the present invention are represented by 53 and the attendant definitions, wherein D represents pyranosyl, furanosyl, acyl, or $(RO)_2P(O)$—.

In certain embodiments, the compounds of the present invention are represented by 53 and the attendant definitions, wherein Z represents Cl or Br.

In certain embodiments, the compounds of the present invention are represented by 53 and the attendant definitions, wherein Ar represents optionally substituted phenyl; and Z represents Cl or Br.

In certain embodiments, the compounds of the present invention are represented by 53 and the attendant definitions, wherein Ar represents optionally substituted phenyl; and M represents O.

In certain embodiments, the compounds of the present invention are represented by 53 and the attendant definitions, wherein Ar represents optionally substituted phenyl; and D represents pyranosyl, furanosyl, acyl, or $(RO)_2P(O)$—.

In certain embodiments, the compounds of the present invention are represented by 53 and the attendant definitions, wherein Ar represents optionally substituted phenyl; Z represents Cl or Br; and M represents O.

In certain embodiments, the compounds of the present invention are represented by 53 and the attendant definitions, wherein Ar represents optionally substituted phenyl; Z represents Cl or Br; M represents O; and D represents pyranosyl, furanosyl, acyl, or $(RO)_2P(O)$—.

Definitions

For convenience, before further description of the present invention, certain terms employed in the specification, examples, and appended claims are collected here.

The term "dioxirane" is art-recognized and refers to a three-membered ring which consists of two oxygen atoms and one carbon atom, wherein the carbon atom bears two substituents that render it tetrahedral.

The terms "dimethyl dioxirane" and "DMDO" refer to the compound below.

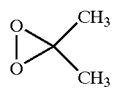

dimethyl dioxirane

The abbreviation "CAN" refers to ceric ammonium nitrate.

The abbreviation "DDQ" refers to 2,3-dichloro-5,6-dicyano-1,4-benzoquinone.

The abbreviations "OBB" and "PBB" refer to ortho-bromobenzyl and para-bromobenzyl, respectively.

The abbreviations "OCB" and "PCB" refer to ortho-chlorobenzyl and para-chlorobenzyl, respectively.

The abbreviation "TBAI" refers to tetra-n-butylammonium iodide.

The abbreviation "NR" means "no reaction."

The terms "purify" means to increase through deliberate action the homogeneity of a compound, composition, preparation or solution.

The term "purified" refers to a compound, composition, preparation or solution whose homogeneity has been increased by purification. Typically, a purified compound, composition, preparation or solution has less than about 10% impurities, preferably less than about 5% impurities, and most preferably less than about 2% impurities.

The term "Lewis acid" is art-recognized and refers to an atom, compound or complex capable of accepting a pair of electrons from another atom, compound or complex.

The term "nucleophile" is recognized in the art, and as used herein means a chemical moiety having a reactive pair of electrons.

The term "electrophile" is art-recognized and refers to chemical moieties which can accept a pair of electrons from a nucleophile as defined above, or from a Lewis base. Electrophilic moieties useful in the method of the present invention include halides and sulfonates.

The term "electron-withdrawing group" is recognized in the art, and denotes the tendency of a substituent to attract valence electrons from neighboring atoms, i.e., the substituent is electronegative with respect to neighboring atoms. A quantification of the level of electron-withdrawing capability is given by the Hammett sigma ($\sigma$) constant. This well known constant is described in many references, for instance, J. March, *Advanced Organic Chemistry*, McGraw Hill Book Company, New York, (1977 edition) pp. 251–259. The Hammett constant values are generally negative for electron donating groups ($\sigma[P]=-0.66$ for $NH_2$) and positive for electron withdrawing groups ($\sigma[P]=0.78$ for a nitro group), $\sigma[P]$ indicating para substitution. Exemplary electron-withdrawing groups include nitro, ketone, aldehyde, sulfonyl, trifluoromethyl, —CN, chloride, and the like. Exemplary electron-donating groups include amino, methoxy, and the like.

The term "catalytic amount" is recognized in the art and means a substoichiometric amount of a reagent relative to a reactant. As used herein, a catalytic amount means from 0.0001 to 90 mole percent reagent relative to a reactant, more preferably from 0.001 to 50 mole percent, still more preferably from 0.01 to 10 mole percent, and even more preferably from 0.1 to 5 mole percent reagent to reactant.

The term "alkyl" refers to the radical of saturated aliphatic groups, including straight-chain alkyl groups, branched-chain alkyl groups, cycloalkyl (alicyclic) groups, alkyl substituted cycloalkyl groups, and cycloalkyl substituted alkyl groups. In preferred embodiments, a straight chain or branched chain alkyl has 30 or fewer carbon atoms in its backbone (e.g., $C_1$–$C_{30}$ for straight chain, $C_3$–$C_{30}$ for branched chain), and more preferably 20 or fewer. Likewise, preferred cycloalkyls have from 3–10 carbon atoms in their ring structure, and more preferably have 5, 6 or 7 carbons in the ring structure.

Moreover, the term "alkyl" (or "lower alkyl") as used throughout the specification and claims is intended to include both "unsubstituted alkyls" and "substituted alkyls", the latter of which refers to alkyl moieties having substituents replacing a hydrogen on one or more carbons of the hydrocarbon backbone. Such substituents can include, for example, a halogen, a hydroxyl, a carbonyl (such as a carboxyl, an ester, a formyl, or a ketone), a thiocarbonyl (such as a thioester, a thioacetate, or a thioformate), an alkoxyl, a phosphoryl, a phosphonate, a phosphinate, an amino, an amido, an amidine, an imine, a cyano, a nitro, an azido, a sulhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate. For instance, the substituents of a substituted alkyl may include substituted and unsubstituted forms of amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —$CF_3$, —CN and the like. Exemplary substituted alkyls are described below. Cycloalkyls can be further substituted with alkyls, alkenyls, alkoxys, alkylthios, aminoalkyls, carbonyl-substituted alkyls, —$CF_3$, —CN, and the like.

The term "arylalkyl", as used herein, refers to an alkyl group substituted with an aryl group (e.g., an aromatic or heteroaromatic group).

The terms "alkenyl" and "alkynyl" refer to unsaturated aliphatic groups analogous in length and possible substitution to the alkyls described above, but that comprise a double or triple bond, respectively.

Unless the number of carbons is otherwise specified, "lower alkyl" as used herein means an alkyl group, as defined above, but having from one to ten carbons, more preferably from one to six carbon atoms in its backbone structure. Likewise, "lower alkenyl" and "lower alkynyl" have similar chain lengths. Preferred alkyl groups are lower alkyls. In preferred embodiments, a substituent designated herein as alkyl is a lower alkyl.

The term "aryl" as used herein includes 5-, 6- and 7-membered single-ring aromatic groups that may include from zero to four heteroatoms, for example, benzene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaromatics". The aromatic ring can be substituted at one or more ring positions with such substituents as described above, for example, halogen, azide, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, —CN, or the like. The term "aryl" also includes polycyclic ring systems having two or more rings in which two or more carbons are common to two adjoining rings (the rings are "fused") wherein at least one of the rings is aromatic, e.g., the other rings can be cycloalkyls, cycloalkenyls, cycloalkynyls, aryls and/or heterocyclyls.

The terms "heterocyclyl" or "heterocyclic group" refer to 3- to 10-membered ring structures, more preferably 3- to 7-membered rings, whose ring structures include one to four heteroatoms. Heterocycles can also be polycycles. Heterocyclyl groups include, for example, thiophene, thianthrene, furan, pyran, isobenzofuran, chromene, xanthene, phenoxathiin, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, perimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring can be substituted at one or more positions with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —CF$_3$, —CN, or the like.

The terms "polycyclyl" or "polycyclic group" refer to two or more rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle can be substituted with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —CF$_3$, —CN, or the like.

The term "carbocycle", as used herein, refers to an aromatic or non-aromatic ring in which each atom of the ring is carbon.

The term "heteroatom" as used herein means an atom of any element other than carbon or hydrogen. Preferred heteroatoms are nitrogen, oxygen, sulfur and phosphorous.

As used herein, the term "nitro" means —NO$_2$; the term "halogen" designates —F, —Cl, —Br or —I; the term "sulfhydryl" means —SH; the term "hydroxyl" means —OH; and the term "sulfonyl" means —SO$_2$—.

The terms "amine" and "amino" are art recognized and refer to both unsubstituted and substituted amines, e.g., a moiety that can be represented by the general formula:

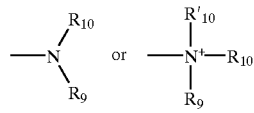

wherein $R_9$, $R_{10}$ and $R'_{10}$ each independently represent a hydrogen, an alkyl, an alkenyl, —(CB$_2$)$_m$—R$_8$, or $R_9$ and $R_{10}$ taken together with the N atom to which they are attached complete a heterocycle having from 4 to 8 atoms in the ring structure; $R_8$ represents an aryl, a cycloalkyl, a cycloalkenyl, a heterocycle or a polycycle; and m is zero or an integer in the range of 1 to 8. In preferred embodiments, only one of $R_9$ or $R_{10}$ can be a carbonyl, e.g., $R_9$, $R_{10}$ and the nitrogen together do not form an imide. In even more preferred embodiments, $R_9$ and $R_{10}$ (and optionally $R'_{10}$) each independently represent a hydrogen, an alkyl, an alkenyl, or —(CH$_2$)$_m$—R$_8$. Thus, the term "alkylamine" as used herein means an amine group, as defined above, having a substituted or unsubstituted alkyl attached thereto, i.e., at least one of $R_9$ and $R_{10}$ is an alkyl group.

The term "acylamino" is art-recognized and refers to a moiety that can be represented by the general formula:

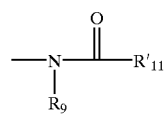

wherein $R_9$ is as defined above, and $R'_{11}$ represents a hydrogen, an alkyl, an alkenyl or —(CH$_2$)$_m$—R$_8$, where m and $R_8$ are as defined above.

The term "amido" is art recognized as an amino-substituted carbonyl and includes a moiety that can be represented by the general formula:

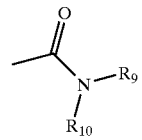

wherein $R_9$, $R_{10}$ are as defined above. Preferred embodiments of the amide will not include imides which may be unstable.

The term "alkylthio" refers to an alkyl group, as defined above, having a sulfur radical attached thereto. In preferred embodiments, the "alkylthio" moiety is represented by one of —S-alkyl, —S-alkenyl, —S-alkynyl, and —S—(CH$_2$)$_m$—R$_8$, wherein m and $R_8$ are defined above. Representative alkylthio groups include methylthio, ethylthio, and the like.

The term "carbonyl" is art recognized and includes such moieties as can be represented by the general formula:

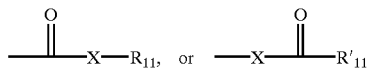

wherein X is a bond or represents an oxygen or a sulfur, and $R_{11}$ represents a hydrogen, an alkyl, an alkenyl, —(CH$_2$)$_m$—R$_8$ or a pharmaceutically acceptable salt, $R'_{11}$ represents a hydrogen, an alkyl, an alkenyl or —(CH$_2$)$_m$—R$_8$, where m and $R_8$ are as defined above. Where X is an oxygen and $R_{11}$ or $R'_{11}$ is not hydrogen, the formula represents an "ester". Where X is an oxygen, and $R_{11}$ is as defined above, the moiety is referred to herein as a carboxyl group, and particularly when $R_{11}$ is a hydrogen, the formula represents a "carboxylic acid". Where X is an oxygen, and $R'_{11}$ is hydrogen, the formula represents a "formate". In general, where the oxygen atom of the above formula is replaced by sulfur, the formula represents a "thiolcarbonyl" group. Where X is a sulfur and $R_{11}$, or $R'_{11}$ is not hydrogen, the formula represents a "thiolester." Where X is a sulfur and $R_{11}$ is hydrogen, the formula represents a "thiolcarboxylic acid." Where X is a sulfur and $R_{11}'$ is hydrogen, the formula represents a "thiolformate." On the other hand, where X is a bond, and $R_{11}$ is not hydrogen, the above formula represents a "ketone" group. Where X is a bond, and $R_{11}$ is hydrogen, the above formula represents an "aldehyde" group.

The terms "alkoxyl" or "alkoxy" as used herein refers to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as can be represented by one of —O-alkyl, —O-alkenyl, —O-alkynyl, —O—(CH$_2$)$_m$—R$_8$, where m and $R_8$ are described above.

The term "sulfonate" is art recognized and includes a moiety that can be represented by the general formula:

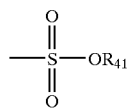

in which $R_{41}$ is an electron pair, hydrogen, alkyl, cycloalkyl, or aryl.

The term "sulfate" is art recognized and includes a moiety that can be represented by the general formula:

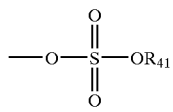

in which $R_{41}$ is as defined above.

The term "sulfonamido" is art recognized and includes a moiety that can be represented by the general formula:

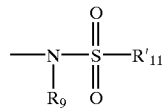

in which $R_9$ and $R'_{11}$ are as defined above.

The term "sulfamoyl" is art-recognized and includes a moiety that can be represented by the general formula:

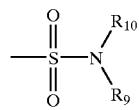

in which $R_9$ and $R_{10}$ are as defined above.

The terms "sulfoxido" or "sulfinyl", a s use d herein, refers to a moiety that can be represented by the general formula:

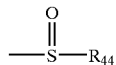

in which $R_{44}$ is selected from the group consisting of hydrogen, alkyl, alkenyl, alkynyl, cycloalkyl, heterocyclyl, aralkyl, or aryl.

A "phosphoryl" can in general be represented by the formula:

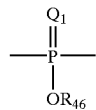

wherein $Q_1$ represented S or O, and $R_{46}$ represents hydrogen, a lower alkyl or an aryl. When used to substitute, e.g., an alkyl, the phosphoryl group of the phosphorylalkyl can be represented by the general formula:

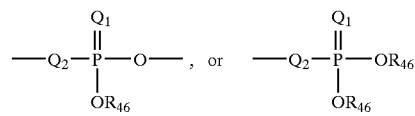

wherein $Q_1$ represented S or O, and each $R_{46}$ independently represents hydrogen, a lower alkyl or an aryl, $Q_2$ represents O, S or N. When $Q_1$ is an S, the phosphoryl moiety is a "phosphorothioate".

A "phosphoramidite" can be represented in the general formula:

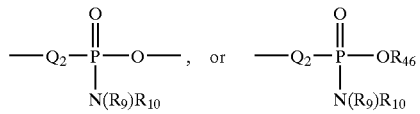

wherein $R_9$ and $R_{10}$ are as defined above, and $Q_2$ represents O, S or N.

A "phosphonamidite" can be represented in the general formula:

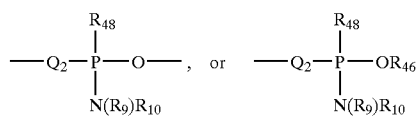

wherein $R_9$ and $R_{10}$ are as defined above, $Q_2$ represents O, S or N, and $R_{48}$ represents a lower alkyl or an aryl, $Q_2$ represents O, S or N.

A "selenoalkyl" refers to an alkyl group having a substituted seleno group attached thereto. Exemplary "selenoethers" which may be substituted on the alkyl are selected from one of —Se-alkyl, —Se-alkenyl, —Se-alkynyl, and —Se—$(CH_2)_m$—$R_7$, m and $R_7$ being defined above.

Analogous substitutions can be made to alkenyl and alkynyl groups to produce, for example, aminoalkenyls, aminoalkynyls, amidoalkenyls, amidoalkynyls, iminoalkenyls, iminoalkynyls, thioalkenyls, thioalkynyls, carbonyl-substituted alkenyls or alkynyls.

The abbreviations Me, Et, Ph, Tf, Nf, Ts, Ms, and dba represent methyl, ethyl, phenyl, trifluoromethanesulfonyl, nonafluorobutanesulfonyl, p-toluenesulfonyl, methanesulfonyl, and dibenzylideneacetone, respectively. A more comprehensive list of the abbreviations utilized by organic chemists of ordinary skill in the art appears in the first issue of each volume of the *Journal of Organic Chemistry*; this list is typically presented in a table entitled *Standard List of Abbreviations*. The abbreviations contained in said list, and all abbreviations utilized by organic chemists of ordinary skill in the art are hereby incorporated by reference.

The terms ortho, meta and para apply to 1,2-, 1,3- and 1,4-disubstituted benzenes, respectively. For example, the names 1,2-dimethylbenzene and ortho-dimethylbenzene are synonymous.

The phrase "protecting group" as used herein means temporary modifications of a potentially reactive functional group which protect it from undesired chemical transformations. Examples of such protecting groups include esters of carboxylic acids, silyl ethers of alcohols, and acetals and ketals of aldehydes and ketones, respectively. The field of protecting group chemistry has been reviewed (Greene, T. W.; Wuts, P. G. M. *Protective Groups in Organic Synthesis*, $2^{nd}$ ed.; Wiley: New York, 1991).

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc.

As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described hereinabove. The permissible substituents can be one or more and the same or different for appropriate organic compounds. For purposes of this invention, the heteroatoms such as nitrogen may have hydrogen substituents and/or any permissible substituents of organic compounds described herein which satisfy the valencies of the heteroatoms. This invention is not intended to be limited in any manner by the permissible substituents of organic compounds.

A "polar solvent" means a solvent which has a dielectric constant (68) of 2.9 or greater, such as DMF, THF, ethylene glycol dimethyl ether (DME), DMSO, acetone, acetonitrile, methanol, ethanol, isopropanol, n-propanol, t-butanol or 2-methoxyethyl ether. Preferred solvents are DMF, DME, NMP, and acetonitrile.

A "polar, aprotic solvent" means a polar solvent as defined above which has no available hydrogens to exchange with the compounds of this invention during reaction, for example DMF, acetonitrile, diglyme, DMSO, or THF.

An "aprotic solvent" means a non-nucleophilic solvent having a boiling point range above ambient temperature, preferably from about 25° C. to about 190° C., more preferably from about 80° C. to about 160° C., most preferably from about 80° C. to 150° C., at atmospheric pressure. Examples of such solvents are acetonitrile, toluene, DMF, diglyme, THF or DMSO.

For purposes of this invention, the chemical elements are identified in accordance with the Periodic Table of the Elements, CAS version, Handbook of Chemistry and Physics, 67th Ed., 1986–87, inside cover. Also for purposes of this invention, the term "hydrocarbon" is contemplated to include all permissible compounds having at least one hydrogen and one carbon atom. In a broad aspect, the permissible hydrocarbons include acyclic and cyclic, branched and unbranched, carbocyclic and heterocyclic, aromatic and nonaromatic organic compounds which can be substituted or unsubstituted.

Catalysts

The active form of the transition metal catalyst is not completely characterized. Therefore, it is contemplated that the "transition metal catalyst" of the present invention, as that term is used herein, shall include any catalytic transition metal and/or catalyst precursor as it is introduced into the reaction vessel and which is, if necessary, converted in situ into the active form, as well as the active form of the catalyst which participates in the reaction.

In preferred embodiments, the transition metal catalyst complex is provided in the reaction mixture is a catalytic amount. In certain embodiments, that amount is in the range of 0.0001 to 20 mol %, and preferably 0.05 to 5 mol %, and most preferably 1–3 mol %, with respect to the limiting reagent. In the instance where the molecular formula of the catalyst complex includes more than one metal, the amount of the catalyst complex used in the reaction may be adjusted accordingly. By way of example, $Pd_2(dba)_3$ has two metal centers; and thus the molar amount of $Pd_2(dba)_3$ used in the reaction may be halved without sacrificing catalytic activity.

Catalysts containing palladium and nickel are preferred. It is expected that these catalysts will perform similarly because they are known to undergo similar reactions, namely oxidative-addition reactions and reductive-elimination reactions, which are thought to be involved in the formation of the products of the present invention. The novel ligands are thought to modify the catalyst performance by, for example, modifying reactivity and preventing undesirable side reactions.

As suitable, the catalysts employed in the subject method involve the use of metals which can mediate cross-coupling of ArX and an amine, or ArX and a boronic acid. In general, any transition metal (e.g., having d electrons) may be used to form the catalyst, e.g., a metal selected from one of Groups 3–12 of the periodic table or from the lanthamide series. However, in preferred embodiments, the metal will be selected from the group of late transition metals, e.g. preferably from Groups 5–12 and even more preferably Groups 7–11. For example, suitable metals include platinum, palladium, iron, nickel, ruthenium and rhodium. The particular form of the metal to be used in the reaction is selected to provide, under the reaction conditions, metal centers which are coordinately unsaturated and not in their highest oxidation state. The metal core of the catalyst will preferably be a zero valent transition metal, such as Pd or Ni with the ability to undergo oxidative addition to Ar—X bond. The zero-valent state, M(0), may be generated in situ, e.g., from M(II).

To further illustrate, suitable transition metal catalysts include soluble or insoluble complexes of platinum, palladium and nickel. Nickel and palladium are particularly preferred and palladium is most preferred. A zero-valent metal center is presumed to participate in the catalytic carbon-heteroatom or carbon-carbon bond forming sequence. Thus, the metal center is desirably in the zero-valent state or is capable of being reduced to metal(0). Suitable soluble palladium complexes include, but are not limited to, tris(dibenzylideneacetone)dipalladium [$Pd_2(dba)_3$], bis(dibenzylideneacetone)palladium [$Pd(dba)_2$] and palladium acetate. Alternatively, particularly for nickel catalysts, the active species for the oxidative-addition step may be in the metal (+1) oxidation state.

Catalysts containing palladium and nickel are preferred. It is expected that these catalysts will perform comparably because they are known in the art to undergo similar reactions, namely cross-coupling reactions, which may be involved in the formation of the products of the present invention.

The coupling can be catalyzed by a palladium catalyst which palladium may be provided in the form of, for illustrative purposes only, Pd/C, $PdCl_2$, $Pd(OAc)_2$, $(CH_3CN)_2 PdCl_2$, $Pd[P(C_6H_5)_3]_4$, and polymer supported Pd(0). In other embodiments, the reaction can be catalyzed by a nickel catalyst which nickel may be provided in the form of, for illustrative purposes only, $Ni(acac)_2$, $NiCl_2[P(C_6H_5)]_2$, $Ni(1,5$-cyclooctadiene$)_2$, $Ni(1,10$-phenanthroline$)_2$, $Ni(dppf)_2$, $NiCl_2(dppf)$, $NiCl_2(1,10$-phenanthroline), Raney nickel and the like, wherein "acac" represents acetylacetonate.

The catalyst will preferably be provided in the reaction mixture as metal-ligand complex comprising a bound supporting ligand, that is, a metal-supporting ligand complex. The ligand effects can be key to favoring, inter alia, the reductive elimination pathway or the like which produces the products, rather than side reactions such as β-hydride elimination. In preferred embodiments, the subject reaction employs bidentate ligands such as bisphosphines or aminophosphines. The ligand, if chiral can be provided as a racemic mixture or a purified stereoisomer. In certain instances, e.g. the improved method for the synthesis of aryl amines, the use of a racemic, chelating ligand is preferred.

The ligand, as described in greater detail below, may be a chelating ligand, such as by way of example only, alkyl and aryl derivatives of phosphines and bisphosphines, amines, diamines, imines, arsines, and hybrids thereof, including hybrids of phosphines with amines. Weakly or non-nucleophilic stabilizing ions are preferred to avoid undesired side reactions involving the counter ion. The catalyst complex may include additional ligands as required to obtain a stable complex. Moreover, the ligand can be added to the reaction mixture in the form of a metal complex, or added as a separate reagent relative to the addition of the metal.

The supporting ligand may be added to the reaction solution as a separate compound or it may be complexed to the metal center to form a metal-supporting ligand complex prior to its introduction into the reaction solution. Supporting ligands are compounds added to the reaction solution which are capable of binding to the catalytic metal center. In some preferred embodiments, the supporting ligand is a chelating ligand. Although not bound by any theory of operation, it is hypothesized that the supporting ligands suppress unwanted side reactions as well as enhance the rate and efficiency of the desired processes. Additionally, they typically prevent precipitation of the catalytic transition metal. Although the present invention does not require the formation of a metal-supporting ligand complex, such complexes have been shown to be consistent with the postulate that they are intermediates in these reactions and it has been observed the selection of the supporting ligand has an affect on the course of the reaction.

The supporting ligand is present in the range of 0.0001 to 40 mol % relative to the limiting reagent, i.e., amine, boronic acid, ketone or the like, or aromatic compound. The ratio of the supporting ligand to catalyst complex is typically in the range of about 1 to 20, and preferably in the range of about 1 to 4 and most preferably 2. These ratios are based upon a single metal complex and a single binding site ligand. In instances where the ligand contains additional binding sites (i.e., a chelating ligand) or the catalyst contains more than one metal, the ratio is adjusted accordingly. By way of example only, the supporting ligand BINAP contains two coordinating phosphorus atoms and thus the ratio of BINAP to catalyst is adjusted downward to about 1 to 10, preferably about 1 to 2 and most preferably 1. Conversely, $Pd_2(dba)_3$ contains two palladium metal centers and the ratio of a non-chelating ligand to $Pd_2(dba)_3$ is adjusted upward to 1 to 40, preferably 1 to 8 and most preferably 4.

In certain embodiments of the subject method, the transition metal catalyst includes one or more phosphine or aminophosphine ligands, e.g., as a Lewis basic ligand that controls the stability and electron transfer properties of the transition metal catalyst, and/or stabilizes the metal intermediates. Phosphine ligands are commercially available or can be prepared by methods similar to known processes. The phosphines can be monodentate phosphine ligands, such as trimethylphosphine, triethylphosphine, tripropylphosphine, triisopropylphosphine, tributylphosphine, tricyclohexylphosphine, trimethyl phosphite, triethyl phosphite, tripropyl phosphite, triisopropyl phosphite, tributyl phosphite and tricyclohexyl phosphite, in particular triphenylphosphine, tri(o-tolyl)phosphine, triisopropylphosphine or tricyclohexylphosphine; or a bidentate phosphine ligand such as 2,2'-bis(diphenylphosphino)-1,1'-binaphthyl (BINAP), 1,2-bis(dimethylphosphino)ethane, 1,2-bis(diethylphosphino)ethane, 1,2-bis(dipropylphosphino)ethane, 1,2-bis(diisopropylphosphino)ethane, 1,2-bis(dibutylphosphino)ethane, 1,2-bis(dicyclohexylphosphino)ethane, 1,3-bis(dicyclohexylphosphino)propane, 1,3-bis(diiso-propylphosphino)propane, 1,4-bis(diisopropylphosphino)-butane and 2,4-bis(dicyclohexylphosphino)pentane. The aminophosphines may be monodentate, e.g. each molecule of aminophosphine donates to the catalytic metal atom only a Lewis basic nitrogen atom or a Lewis basic phosphorus atom. Alternatively, the aminophosphine may be a chelating ligand, e.g. capable of donating to the catalytic metal atom both a Lewis basic nitrogen atom and a Lewis basic phosphorus atom.

In some instances, it may be necessary to include additional reagents in the reaction mixture to promote reactivity of either the transition metal catalyst or activated aryl nucleus. In particular, it may be advantageous to include a suitable base. In general, a variety of bases may be used in practice of the present invention. It has not been determined at which point(s) in the mechanisms of the subject transformations the base participates. The base may optionally be sterically hindered to discourage metal coordination of the base in those circumstances where such coordination is possible, i.e., alkali metal alkoxides. Exemplary bases include such as, by way of example only: alkoxides such as sodium tert-butoxide; alkali metal amides such as sodium amide, lithium diisopropylamide, and alkali metal bis(trialkylsilyl)amide, e.g., such as lithium bis(trimethylsilyl) amide (LiHMDS) or sodium bis(trimethylsilyl)amide (NaHMDS); tertiary amines (e.g. triethylamine, trimethylamine, 4-(dimethylamino)pyridine (DMAP), 1,5-diazabicycl[4.3.0]non-5-ene (DBN), 1,5-diazabicyclo[5.4.0] undec-5-ene (DBU); alkali or alkaline earth carbonate, bicarbonate or hydroxide (e.g. sodium, magnesium, calcium, barium, potassium carbonate, phosphate, hydroxide and bicarbonate). By way of example only, suitable bases include NaH, LiH, KH, $K_2CO_3$, $Na_2CO_3$, $Tl_2CO_3$, $Cs_2CO_3$, K(OtBu), Li(OtBu), Na(OtBu) K(OAr), Na(OAr), and triethylamine, or mixtures thereof. Preferred bases include CsF, $K_3PO_4$, DBU, NaOt-Bu, KOt-Bu, LiN(i-Pr)$_2$ (LDA), KN(SiMe$_3$)$_2$, NaN(SiMe$_3$)$_2$, and LiN(SiMe$_3$)$_2$.

Base is used in approximately stoichiometric proportions in the subject methods. The present invention has demonstrated that there is no need for large excesses of base in order to obtain good yields of the desired products under mild reaction conditions. No more than four equivalents of base, and preferably no more than two equivalents, are needed. Furthermore, in reactions using the corresponding salt of an amine, boronic acid, ketone or the like, additional base may not be required.

Reaction Conditions

The reactions of the present invention may be performed under a wide range of conditions, though it will be understood that the solvents and temperature ranges recited herein are not limitative and only correspond to a preferred mode of the process of the invention.

In general, it will be desirable that reactions are run using mild conditions which will not adversely affect the reactants, the catalyst, or the product. For example, the reaction temperature influences the speed of the reaction, as well as the stability of the reactants, products and catalyst.

In general, the subject reactions are carried out in a liquid reaction medium. The reactions may be run without addition of solvent. Alternatively, the reactions may be run in an inert solvent, preferably one in which the reaction ingredients, including the catalyst, are substantially soluble. Suitable solvents include ethers such as diethyl ether, 1,2-dimethoxyethane, diglyme, t-butyl methyl ether, tetrahydrofuran and the like; halogenated solvents such as chloroform, dichloromethane, dichloroethane, chlorobenzene, and the like; aliphatic or aromatic hydrocarbon solvents such as benzene, xylene, toluene, hexane, pentane and the like; esters and ketones such as ethyl acetate, acetone, and 2-butanone; polar aprotic solvents such as acetonitrile, dimethylsulfoxide, dimethylformamide and the like; or combinations of two or more solvents.

The invention also contemplates reaction in a biphasic mixture of solvents, in an emulsion or suspension, or reaction in a lipid vesicle or bilayer. In certain embodiments, it may be preferred to perform the catalyzed reactions in the solid phase with one of the reactants anchored to a solid support.

In certain embodiments it is preferable to perform the reactions under an inert atmosphere of a gas such as nitrogen or argon.

The reaction processes of the present invention can be conducted in continuous, semi-continuous or batch fashion and may involve a liquid recycle operation as desired. The processes of this invention are preferably conducted in batch fashion. Likewise, the manner or order of addition of the reaction ingredients, catalyst and solvent are also not generally critical to the success of the reaction, and may be accomplished in any conventional fashion.

The reaction can be conducted in a single reaction zone or in a plurality of reaction zones, in series or in parallel or it may be conducted batchwise or continuously in an elongated tubular zone or series of such zones. The materials of construction employed should be inert to the starting materials during the reaction and the fabrication of the equipment should be able to withstand the reaction temperatures and pressures. Means to introduce and/or adjust the quantity of starting materials or ingredients introduced batchwise or continuously into the reaction zone during the course of the reaction can be conveniently utilized in the processes especially to maintain the desired molar ratio of the starting materials. The reaction steps may be effected by the incremental addition of one of the starting materials to the other. Also, the reaction steps can be combined by the joint addition of the starting materials to the metal catalyst. When complete conversion is not desired or not obtainable, the starting materials can be separated from the product and then recycled back into the reaction zone.

The processes may be conducted in either glass lined, stainless steel or similar type reaction equipment. The reaction zone may be fitted with one or more internal and/or external heat exchanger(s) in order to control undue temperature fluctuations, or to prevent any possible "runaway" reaction temperatures.

Furthermore, one or more of the reactants can be immobilized or incorporated into a polymer or other insoluble matrix by, for example, derivativation with one or more of substituents of the aryl group.

Subsequent Transformations

A product synthesized by a method of the present invention may be either an end-product or an intermediate in a synthesis scheme. In cases where the product synthesized by a method of the present invention is an intermediate, the product may be subjected to one or more additional transformations to yield the desired end-product. The set of additional transformations contemplated comprises isomerizations, hydrolyses, oxidations, reductions, additions, eliminations, olefinations, functional group interconversions, transition metal-mediated reactions, transition metal-catalyzed reactions, bond-forming reactions, cleavage reactions, fragmentation reactions, thermal reactions, photochemical reactions, cycloadditions, sigmatropic rearrangements, electrocyclic reactions, chemoselective reactions, regioselective reactions, stereoselective reactions, diastereoselective reactions, enantioselective reactions, and kinetic resolutions. The invention expressly comprises use of a method of the present invention as a step—either initial, intermediate or final—in the synthesis of known or new pharmaceuticals, e.g., antivirals, antibiotics, and analgesics.

Overview of Strategies and Methods of Combinatorial Chemistry

The subject complexes, and the reactions they catalyze, lend themselves to the creation of combinatorial libraries of compounds, including for the screening of pharmaceutical, agrochemical or other biological or medically-related activity or material-related qualities. A combinatorial library for the purposes of the present invention is a mixture of chemically related compounds which may be screened together for a desired property; said libraries may be in solution or covalently linked to a solid support. The preparation of many related compounds in a single reaction greatly reduces and simplifies the number of screening processes which need to be carried out. Screening for the appropriate biological, pharmaceutical, agrochemical or physical property may be done by conventional methods.

The art of combinatorial chemistry may be applied to the subject invention in a number of senses, including, but not limited to: the combinatorial synthesis of variegated libraries of metal-containing complexes that may be screened for the redox properties noted above; and the use of novel metal-containing complexes of the present invention as reagents in redox reactions carried out on combinatorial libraries of organic molecules.

A variety of techniques are available in the art for generating combinatorial libraries of small organic molecules. See, for example, Blondelle et al. (1995) *Trends Anal. Chem.* 14:83; the Affymax U.S. Pat. Nos. 5,359,115 and 5,362,899: the Ellman U.S. Pat. No. 5,288,514: the Still et al. PCT publication WO 94/08051; Chen et al. (1994) *JACS* 116:2661: Kerr et al. (1993) *JACS* 115:252; PCT publications WO92/10092, WO93/09668 and WO91/07087; and the Lemer et al. PCT publication WO93/20242). Accordingly, a variety of libraries on the order of about 16 to 1,000,000 or more diversomers can be synthesized and screened for a particular activity or property.

In an exemplary embodiment, a library of substituted diversomers can be synthesized using the subject reactions adapted to the techniques described in the Still et al. PCT publication WO 94/08051, e.g., being linked to a polymer bead by a hydrolyzable or photolyzable group, e.g., located at one of the positions of substrate. According to the Still et al. technique, the library is synthesized on a set of beads, each bead including a set of tags identifying the particular diversomer on that bead. In one embodiment, which is particularly suitable for discovering enzyme inhibitors, the beads can be dispersed on the surface of a permeable membrane, and the diversomers released from the beads by lysis of the bead linker. The diversomer from each bead will diffuse across the membrane to an assay zone, where it will interact with an enzyme assay. Detailed descriptions of a number of combinatorial methodologies are provided below.

Direct Characterization

A growing trend in the field of combinatorial chemistry is to exploit the sensitivity of techniques such as mass spectrometry (MS), e.g., which can be used to characterize sub-femtomolar amounts of a compound, and to directly determine the chemical constitution of a compound selected from a combinatorial library. For instance, where the library is provided on an insoluble support matrix, discrete populations of compounds can be first released from the support and characterized by MS. In other embodiments, as part of the MS sample preparation technique, such MS techniques as MALDI can be used to release a compound from the matrix, particularly where a labile bond is used originally to tether the compound to the matrix. For instance, a bead selected from a library can be irradiated in a MALDI step in order to release the diversomer from the matrix, and ionize the diversomer for MS analysis.

B) Multipin Synthesis

The libraries of the subject method can take the multipin library format. Briefly, Geysen and co-workers (Geysen et al. (1984) *PNAS* 81:3998–4002) introduced a method for generating compound libraries by a parallel synthesis on polyacrylic acid-grated polyethylene pins arrayed in the microtitre plate format. The Geysen technique can be used to synthesize and screen thousands of compounds per week using the multipin method, and the tethered compounds may be reused in many assays. Appropriate linker moieties can also been appended to the pins so that the compounds may be cleaved from the supports after synthesis for assessment of purity and further evaluation (c.f., Bray et al. (1990) *Tetrahedron Lett* 31:5811–5814; Valerio et al. (1991) *Anal Biochem* 197:168–177; Bray et al. (1991) *Tetrahedron Lett* 32:6163–6166).

C) Divide-Couple-Recombine

In yet another embodiment, a variegated library of compounds can be provided on a set of beads utilizing the strategy of divide-couple-recombine (see, e.g., Houghten (1985) *PNAS* 82:5131–5135; and U.S. Pat. Nos. 4,631,211; 5,440,016; 5,480,971). Briefly, as the name implies, at each synthesis step where degeneracy is introduced into the library, the beads are divided into separate groups equal to the number of different substituents to be added at a particular position in the library, the different substituents coupled in separate reactions, and the beads recombined into one pool for the next iteration.

In one embodiment, the divide-couple-recombine strategy can be carried out using an analogous approach to the so-called "tea bag" method first developed by Houghten, where compound synthesis occurs on resin sealed inside porous polypropylene bags (Houghten et al. (1986) *PNAS* 82:5131–5135). Substituents are coupled to the compound-bearing resins by placing the bags in appropriate reaction solutions, while all common steps such as resin washing and deprotection are performed simultaneously in one reaction vessel. At the end of the synthesis, each bag contains a single compound.

D) Combinatorial Libraries by Light-Directed, Spatially Addressable Parallel Chemical Synthesis A scheme of combinatorial synthesis in which the identity of a compound is given by its locations on a synthesis substrate is termed a spatially-addressable synthesis. In one embodiment, the combinatorial process is carried out by controlling the addition of a chemical reagent to specific locations on a solid support (Dower et al. (1991) *Annu Rep Med Chem* 26:271–280; Fodor, S. P. A. (1991) *Science* 251:767; Pirrung et al. (1992) U.S. Pat. No. 5,143,854; Jacobs et al. (1994) *Trends Biotechnol* 12:19–26). The spatial resolution of photolithography affords miniaturization. This technique can be carried out through the use protection/deprotection reactions with photolabile protecting groups.

The key points of this technology are illustrated in Gallop et al. (1994) *J Med Chem* 37:1233–1251. A synthesis substrate is prepared for coupling through the covalent attachment of photolabile nitroveratryloxycarbonyl (NVOC) protected amino linkers or other photolabile linkers. Light is used to selectively activate a specified region of the synthesis support for coupling. Removal of the photolabile protecting groups by light (deprotection) results in activation of selected areas. After activation, the first of a set of amino acid analogs, each bearing a photolabile protecting group on the amino terminus, is exposed to the entire surface. Coupling only occurs in regions that were addressed by light in the preceding step. The reaction is stopped, the plates washed, and the substrate is again illuminated through a second mask, activating a different region for reaction with a second protected building block. The pattern of masks and the sequence of reactants define the products and their locations. Since this process utilizes photolithography techniques, the number of compounds that can be synthesized is limited only by the number of synthesis sites that can be addressed with appropriate resolution. The position of each compound is precisely known; hence, its interactions with other molecules can be directly assessed.

In a light-directed chemical synthesis, the products depend on the pattern of illumination and on the order of addition of reactants. By varying the lithographic patterns, many different sets of test compounds can be synthesized simultaneously; this characteristic leads to the generation of many different masking strategies.

E) Encoded Combinatorial Libraries

In yet another embodiment, the subject method utilizes a compound library provided with an encoded tagging system. A recent improvement in the identification of active compounds from combinatorial libraries employs chemical indexing systems using tags that uniquely encode the reaction steps a given bead has undergone and, by inference, the structure it carries. Conceptually, this approach mimics phage display libraries, where activity derives from expressed peptides, but the structures of the active peptides are deduced from the corresponding genomic DNA sequence. The first encoding of synthetic combinatorial libraries employed DNA as the code. A variety of other forms of encoding have been reported, including encoding with sequenceable bio-oligomers (e.g., oligonucleotides and peptides), and binary encoding with additional non-sequenceable tags.

1) Tagging with Sequenceable Bio-Oligomers

The principle of using oligonucleotides to encode combinatorial synthetic libraries was described in 1992 (Brenner et al. (1992) PNAS 89:5381–5383), and an example of such a library appeared the following year (Needles et al. (1993) *PNAS* 90:10700–10704). A combinatorial library of nominally $7^7$ (=823,543) peptides composed of all combinations of Arg, Gln, Phe, Lys, Val, D-Val and Thr (three-letter amino acid code), each of which was encoded by a specific dinucleotide (TA, TC, CT, AT, TT, CA and AC, respectively), was prepared by a series of alternating rounds of peptide and oligonucleotide synthesis on solid support. In this work, the amine linking functionality on the bead was specifically differentiated toward peptide or oligonucleotide synthesis by simultaneously preincubating the beads with reagents that generate protected OH groups for oligonucleotide synthesis and protected $NH_2$ groups for peptide synthesis (here, in a ratio of 1:20). When complete, the tags each consisted of 69-mers, 14 units of which carried the code. The bead-bound library was incubated with a fluorescently labeled antibody, and beads containing bound antibody that fluoresced strongly were harvested by fluorescence-activated cell sorting (FACS). The DNA tags were amplified by PCR and sequenced, and the predicted peptides were synthesized. Following such techniques, compound libraries can be derived for use in the subject method, where the oligonucleotide sequence of the tag identifies the sequential combinatorial reactions that a particular bead underwent, and therefore provides the identity of the compound on the bead.

The use of oligonucleotide tags permits exquisitely sensitive tag analysis. Even so, the method requires careful choice of orthogonal sets of protecting groups required for alternating co-synthesis of the tag and the library member. Furthermore, the chemical lability of the tag, particularly the phosphate and sugar anomeric linkages, may limit the choice of reagents and conditions that can be employed for the synthesis of non-oligomeric libraries. In preferred embodiments, the libraries employ linkers permitting selective detachment of the test compound library member for assay.

Peptides have also been employed as tagging molecules for combinatorial libraries. Two exemplary approaches are described in the art, both of which employ branched linkers to solid phase upon which coding and ligand strands are alternately elaborated. In the first approach (Kerr J M et al. (1993) *J Am Chem Soc* 115:2529–2531), orthogonality in synthesis is achieved by employing acid-labile protection for the coding strand and base-labile protection for the compound strand.

In an alternative approach (Nikolaiev et al. (1993) *Pept Res* 6:161–170), branched linkers are employed so that the coding unit and the test compound can both be attached to the same functional group on the resin. In one embodiment, a cleavable linker can be placed between the branch point and the bead so that cleavage releases a molecule containing both code and the compound (Ptek et al. (1991) *Tetrahedron Lett* 32:3891–3894). In another embodiment, the cleavable linker can be placed so that the test compound can be selectively separated from the bead, leaving the code behind. This last construct is particularly valuable because it permits screening of the test compound without potential interference of the coding groups. Examples in the art of independent cleavage and sequencing of peptide library members and their corresponding tags has confirmed that the tags can accurately predict the peptide structure.

2) Non-Sequenceable Tagging: Binary Encoding

An alternative form of encoding the test compound library employs a set of non-sequencable electrophoric tagging molecules that are used as a binary code (Ohlmeyer et al. (1993) *PNAS* 90:10922–10926). Exemplary tags are haloaromatic alkyl ethers that are detectable as their trimethylsilyl ethers at less than femtomolar levels by electron capture gas chromatography (ECGC). Variations in the length of the alkyl chain, as well as the nature and position of the aromatic halide substituents, permit the synthesis of at least 40 such tags, which in principle can encode $2^{40}$ (e.g., upwards of $10^{12}$) different molecules. In the original report (Ohlmeyer et al., supra) the tags were bound to about 1% of the available amine groups of a peptide library via a photocleavable o-nitrobenzyl linker. This approach is convenient when preparing combinatorial libraries of peptide-like or other amine-containing molecules. A more versatile system has, however, been developed that permits encoding of essentially any combinatorial library. Here, the compound would be attached to the solid support via the photocleavable linker and the tag is attached through a catechol ether linker via carbene insertion into the bead matrix (Nestler et al. (1994) *J Org Chem* 59:4723–4724). This orthogonal attachment strategy permits the selective detachment of library members for assay in solution and subsequent decoding by ECGC after oxidative detachment of the tag sets.

Although several amide-linked libraries in the art employ binary encoding with the electrophoric tags attached to amine groups, attaching these tags directly to the bead matrix provides far greater versatility in the structures that can be prepared in encoded combinatorial libraries. Attached in this way, the tags and their linker are nearly as unreactive as the bead matrix itself. Two binary-encoded combinatorial libraries have been reported where the electrophoric tags are attached directly to the solid phase (Ohlmeyer et al. (1995) *PNAS* 92:6027–6031) and provide guidance for generating the subject compound library. Both libraries were constructed using an orthogonal attachment strategy in which the library member was linked to the solid support by a photolabile linker and the tags were attached through a linker cleavable only by vigorous oxidation. Because the library members can be repetitively partially photoeluted from the solid support, library members can be utilized in multiple assays. Successive photoelution also permits a very high throughput iterative screening strategy: first, multiple beads are placed in 96-well microtiter plates; second, compounds are partially detached and transferred to assay plates; third, a metal binding assay identifies the active wells; fourth, the corresponding beads are rearrayed singly into new microtiter plates; fifth, single active compounds are identified; and sixth, the structures are decoded.

Exemplification

The invention now being generally described, it will be more readily understood by reference to the following examples, which are included merely for purposes of illustration of certain aspects and embodiments of the present invention, and are not intended to limit the invention.

General Methods for the Examples

All chemicals used were reagent grade and used as supplied except where noted. Dichloromethane ($CH_2Cl_2$) was distilled from calcium hydride under $N_2$. Tetrahydrofuran (THF) was distilled from Na/benzophenone under $N_2$. Toluene was distilled under nitrogen from molten sodium. Benzylamine, n-hexylamine, morpholine and N-methylaniline were obtained from Aldrich Chemical Co. and passed through basic alumina before use. Palladium acetate, tris(dibenzylideneacetone)dipalladium(0), racemic BINAP and (o-biphenyl)P(t-Bu)$_2$ were obtained from Strem Chemical company. Sodium t-butoxide was purchased from Aldrich Chemical Company; the bulk of this material was stored under nitrogen in a Vacuum Atmospheres glovebox. Small portions (1–2 g) were removed from the glovebox in glass vials, stored in the air in desiccators filled with anhydrous sodium sulfate, and weighed in the air. Analytical thin-layer chromatography was performed on E. Merck silica gel 60 $F_{254}$ plates (0.25 mm). Compounds were visualized by dipping the plates in a cerium sulfate-ammonium molybdate solution followed by heating. Liquid column chromatography was performed using forced flow of the indicated solvent on Sigma H-type silica (10–40 $\mu$m). $^1$H NMR spectra were obtained on a Varian VXR-500 spectrometer (500 MHz) and are reported in parts per million ($\delta$) relative to CHCl$_3$ (7.27 ppm). Coupling constants (J) are reported in Hertz. $^{13}$C NMR spectra were obtained on a Varian VXR-500 spectrometer (125 MHz) and are reported in 6 relative to CDCl$_3$ (77.23 ppm) as an internal reference. Abbreviations: TMSOTf=trimethysilyl triflate, DDQ=2,3-dichloro-5,6-dicyanoquinone, CAN=cerium(IV) ammonium nitrate, DMAP=4-N,N-dimethylaminopyridine, BINAP=2,2'-bis(diphenylphosphino)-1,1'-binapthyl.

EXAMPLE 1

General Procedure for Benzylation of Alcohols

A flask containing the alcohol (1.0 equiv) was purged with nitrogen and charged with N,N-dimethylformamide (10 mL/mmol OH). A nitrogen purge was installed and NaH (1.1 equiv) and the substituted benzyl bromide (1.1 equiv) were added. The reaction was stirred at room temperature for 30 min then quenched by dropwise addition of water, diluted with EtOAc and washed with water and brine. The organics were dried over Na$_2$SO$_4$, filtered, concentrated and purified by flash silica column chromatography.

EXAMPLE 2

General Procedure for the Catalytic Amination of Aryl Bromides

A round-bottom flask was charged with aryl bromide (1 equiv) and co-evaporated with 3×3 mL toluene. The flask was purged with argon, the amine (1.2 equiv) was added and the residue dissolved in toluene (2 mL/mmol halide). An oven-dried resealable Schlenk flask was evacuated and backfilled with argon. The flask was charged with Pd$_2$(dba)$_3$ (1.0 mol % Pd), (o-biphenyl)P(t-Bu)$_2$ (2 mol %), NaOtBu (1.4 equiv), evacuated and backfilled with argon. A rubber septum was installed and the aryl bromide/amine solution was added via cannula. A teflon screwcap was installed and the reaction was heated to 80° C. with vigorous stirring. After 5 h, the reaction was cooled to room temperature, diluted with diethyl ether, filtered through a silica plug and concentrated. The crude product was either purified by flash silica column chromatography or cleaved directly with a Lewis acid.

EXAMPLE 3

General Procedure for the Catalytic Amination of Aryl Chlorides

A round-bottom flask was charged with aryl chloride (1 equiv) and co-evaporated with 3×3 mL toluene. The flask was purged with argon, the amine (1.2 equiv) was added and the residue dissolved in toluene (2 mL/mmol halide). An oven-dried resealable Schlenk flask was evacuated and backfilled with argon. The flask was charged with Pd(OAc)$_2$ (2.0 mol % Pd), (o-biphenyl)P(t-Bu)$_2$ (4.0 mol %), NaOtBu (1.4 equiv), evacuated and backfilled with argon. A rubber septum was installed and the aryl chloride/amine solution was added via cannula. A teflon screwcap was installed and the reaction was stirred at room temperature. After 16 h, the reaction was diluted with diethyl ether, filtered through a silica plug and concentrated. The crude product was either purified by flash silica column chromatography or cleaved directly with a Lewis acid.

EXAMPLE 4
General Procedure for the Deprotection of Amino Substituted Benzyl Ethers A solution of aminobenzyl ether (1 equiv) in CH$_2$Cl$_2$ was reacted with the appropriate Lewis acid (1 equiv). After stirring at room temperature for 30 min the reaction was diluted with CH$_2$Cl$_2$ and washed with H$_2$O, NaHCO$_3$ and brine. The organics were dried over Na$_2$SO$_4$, filtered through celite and concentrated. The crude product was purified by flash silica column chromatography.

EXAMPLE 5
Cleavage of Various Amino Substituted Benzyl Ethers (See FIG. 7)

A solution of 16 (0.010 mmol) in 0.5 mL CH$_2$Cl$_2$ was reacted with 0.010 mmol each: TiCl$_4$, SnCl$_4$, ZnCl$_2$, TMSOTf, and NaOMe. A 9:1 CH$_3$CN:H$_2$O solution was used for reaction with DDQ and CAN. All reactions were carried out at room temperature for 16 h unless observed to be complete by TLC. Reaction of 16 with TiCl$_4$ and SnCl$_4$ resulted in complete conversion within 5 min whereas ZnCl$_2$ proved ineffective. Reaction with TMSOTf led to degradation products and strongly basic conditions such as NaOMe had no effect even upon prolonged reflux at 50° C. Oxidative conditions proved successful with DDQ affording 25% conversion after 30 min and CAN affording 75% conversion in the same time.

On the same scale, 17 was reacted with TiCl$_4$, SnCl$_4$, and ZnCl$_2$. Reaction with TiCl$_4$ and SnCl$_4$ resulted in complete conversion within 5 min while ZnCl$_2$ provided deprotected product in quantitative yield in 30 min.

Similarly, 18 was reacted with TiCl$_4$ and ZnCl$_2$. Reaction with TiCl$_4$ resulted in complete conversion within 5 min while ZnCl$_2$ was ineffective.

Reaction of 19 with TiCl$_4$ provided deprotected product in 75% in 5 min.

Ortho aniline derivative 20 was reacted with TiCl$_4$, SnCl$_4$, and ZnCl$_2$. Reaction with TiCl$_4$ resulted in complete conversion within 5 min while SnCl$_4$ and ZnCl$_2$ were ineffective.

Overall, TiCl$_4$ was effective for the deprotection of all p-aminobenzyl ethers examined. (p-N-Methyl-N-phenyl) aminobenzyl ethers are readily cleaved with the mild Lewis acid ZnCl$_2$.

EXAMPLE 6
6-O-(4-Bromobenzyl)-1,2:3,4-di-O-isopropylidene-α-D-galactopyranoside (2) (See FIG. 1).

The general procedure outlined in Example 1, using 1 (3.12 g, 12.0 mmol) and 4-bromobenzylbromide (3.30 g, 13.2 mmol) gave 4.96 g (96%) of 2 as a colorless oil after purification by flash silica column chromatography (20% EtOAc/Hexanes). [α]$^{24}_D$: −49.6° (c 1.62, CH$_2$Cl$_2$); IR (thin film) 2987, 2933, 1478, 1070 cm$^{-1}$; $^1$H-NMR (CDCl$_3$) δ 7.43 (d, J=8.24 Hz, 2H), 7.20 (d, J=8.54 Hz, 2H), 5.53 (d, J=4.88 Hz, 1H), 4.58 (dd, J=2.44, 7.93 Hz, 1H), 4.55 (d, J=12.50 Hz, 1H), 4.47 (d, J=12.20 Hz, 1H), 4.30 (dd, J=2.24, 5.19 Hz, 1H), 4.24 (dd, J=1.83, 7.93 Hz, 1H), 3.98 (dt, J=1.83, 7.02 Hz, 1H), 3.68–3.58 (m, 2H), 1.52 (s, 3H), 1.42 (s, 3H), 1.32 (s, 3H), 1.31 (s, 3H); $^{13}$C-NMR (CDCl$_3$) δ 137.5, 131.5, 129.4, 121.5, 109.3, 108.6, 96.5, 72.6, 71.3, 70.8, 70.6, 69.2, 67.1, 26.2, 25.1, 24.6; FAB MS m/z (M+Na)$^+$: calcd 451.0732, obsd 451.0722.

EXAMPLE 7
6-O-(4-Chlorobenzyl)-1,2:3,4-di-O-isopropylidene-α-D-galactopyranoside (3) (See FIG. 1)

The general procedure outlined in Example 1, using 1 (2.60 g, 10.0 mmol) and 4-chlorobenzylchloride (1.93 g, 12.0 mmol) and tetrabutylammonium iodide (26 mg, 0.07 mmol) gave 3.65 g (95%) of 3 as a colorless oil after purification by flash silica column chromatography (20% EtOAc/Hexanes). [α]$^{24}_D$: −59.6° (c 1.73, CH$_2$Cl$_2$); IR (thin film) 2987, 2934, 1382, 1070 cm$^{-1}$; $^1$H-NMR (CDCl$_3$) δ 7.31–7.26 (m, 4H), 5.54 (d, J=4.88 Hz, 1H), 4.61–4.56 (m, 2H), 4.50 (d, J=12.20 Hz, 1H), 4.30 (dd, J=2.44, 5.19 Hz, 1H), 4.25 (dd, J=1.83, 7.93 Hz, 1H), 3.69–3.58 (m, 2H), 1.53 (s, 3H), 1.43 (s, 3H), 1.33 (s, 3H), 1.32 (s, 3H); $^{13}$C-NMR (CDCl$_3$) δ 137.0, 133.3, 129.1, 128.6, 109.3, 108.7, 96.5, 72.6, 71.3, 70.6 (2 lines), 69.1, 67.0, 26.2, 26.1, 25.1, 24.6; FAB MS m/z (M+Na)$^+$: calcd 407.1237, obsd 407.1232.

EXAMPLE 8
6-O-(2-Bromobenzyl)-1,2:3,4-di-O-isopropylidene-α-D-galactopyranoside (4). (See FIG. 1)

The general procedure outlined in Example 1, using 1 (3.12 g, 12.0 mmol) and 2-bromobenzylbromide (3.30 g, 13.2 mmol) gave 4.96 g (99%) of 4 as a colorless oil after purification by flash silica column chromatography (20% EtOAc/Hexanes). [α]$^{24}_D$: −48.6° (c 1.39, CH$_2$Cl$_2$); IR (thin film) 2987, 2933, 1381, 1070 cm$^{-1}$; $^1$H-NMR (CDCl$_3$) δ 7.51–7.49 (m, 2H), 7.29 (dt, J=1.22, 7.02 Hz, 1H), 7.11 (dt, J=1.83, 7.63 Hz, 1H), 5.55 (d, J=5.19 Hz, 1H), 4.67–4.59 (m, 3H), 4.32–4.29 (m, 2H), 4.06 (dt, J=1.83, 6.41 Hz, 1H), 3.78–3.68 (m, 2H), 1.55 (s, 3H), 1.44 (s, 3H), 1.33 (s, 3H), 1.32 (s, 3H); $^{13}$C-(CDCl$_3$) δ 137.7, 132.5, 129.1, 128.9, 127.4, 122.6, 109.3, 108.7, 96.5, 72.6, 71.3, 70.8, 70.7, 69.5, 66.8, 26.3, 26.1, 25.1, 24.6; FAB MS m/z (M+Na)$^+$: calcd 451.0732, obsd 451.0726.

EXAMPLE 9
6-O-(2-Chlorobenzyl)-1,2:3,4-di-O-isopropylidene-α-D-galactopyranoside (5). (See FIG. 1)

General procedure A using 1 (3.12 g, 12.0 mmol) and 2-chlorobenzylbromide (1.71 mL, 13.2 mmol) gave 4.46 g (97%) of 5 as a colorless oil after purification by flash silica column chromatography (20% EtOAc/Hexanes). [α]$^{24}_D$: −57.2° (c 1.62, CH$_2$Cl$_2$); IR (thin film) 2987, 2934, 1382, 1070 cm$^{-1}$; $^1$H-NMR (CDCl$_3$) δ 7.51 (dd, J=1.83, 7.63 Hz, 1H), 7.31 (dd, J=1.52, 7.93 Hz, 1H), 7.24 (dt, J=1.54, 7.63 Hz, 1H), 7.19 (dt, J=1.86, 7.63, 1H), 5.55 (d, J=4.88 Hz, 1H), 4.79 (d, J=13.10 Hz, 1H), 4.65 (d, J=13.10 Hz, 1H), 4.60 (dd, J=2.44, 7.93 Hz, 1H), 4.32–4.27 (m, 2H), 4.06 (dt, J=1.52, 6.20 Hz, 1H), 3.78–3.69 (m, 2H), 1.54 (s, 3H), 1.44 (s, 3H), 1.33 (s, 3H), 1.32 (s, 3H); $^{13}$C-NMR (CDCl$_3$) δ 136.2, 132.8, 129.3, 129.1, 128.6, 126.8, 109.3, 108.7, 96.5, 71.3, 70.8, 70.7, 70.3, 69.5, 66.8, 26.2, 26.1, 25.1, 24.6; FAB MS m/z (M+Na)$^+$: calcd 407.1237, obsd 407.1228.

EXAMPLE 10
3-O-(4-Bromobenzyl)-6-O-triisopropylsilyl-D-arabino-hex-1-enitol 7. (See FIG. 2)

To a solution of 6-O-triisopropylsilylglucal 6 (3.01 g, 10.0 mmol) in toluene (250 mL) was added Bu$_2$SnO (2.49 g, 10.0 mmol). A Dean-Stark trap equipped with a reflux condenser was installed and the reaction was heated to reflux and all solids dissolved in 20 min. After 16 h at reflux, the reaction was concentrated to 100 mL by distilling off the solvent.

Upon cooling to room temperature, 4-bromobenzyl bromide (5.00 g, 20.0 mmol) and tetrabutylammonium iodide (3.69 g, 10.0 mmol) were added. The reaction was heated to reflux for 5 h, cooled to room temperature and concentrated in vacuo to afford a red oil. Purification by flash silica column chromatography (2–5–10% EtOAc/Hexanes) gave 4.14 g (88%) of 7 as a colorless oil. $[\alpha]^{24}_D$: −27.3° (c 1.82, $CH_2Cl_2$); IR (thin film) 3464, 2941, 2865, 1645, 1463 cm$^{-1}$; $^1$H-NMR (CDCl$_3$) δ 7.46 (d, J=8.54 Hz, 2H), 7.26 (d, J=8.54 Hz, 2H), 6.34 (dd, J=1.53, 6.10 Hz, 1H), 4.78 (dd, J=2.14, 6.10 Hz, 1H), 4.62 (s, 2H), 4.13–3.96 (m, 5H), 3.85–3.82 (m, 1H), 3.23 (d, J=2.75 Hz, 1H), 1.13–1.06 (m, 21H); $^{13}$C-NMR (CDCl$_3$) δ 144.7, 137.8, 131.6, 129.5, 121.6, 100.4, 76.9, 76.6, 71.0, 70.5, 64.5, 18.1, 12.0; FAB MS m/z (M+Na)$^+$ calcd 493.1386, obsd 493.1394.

4-O-Acetyl-3-O-(4-bromobenzyl)-6-O-triisopropylsilyl-D-arabino-hex-1-enitol 7a.

Unambiguous assignment of the regioselective benzylation of 6 was provided by acetylation of 7. A solution of 7 (0.296 g, 0.623 mmol) in $CH_2Cl_2$ (4 mL) was reacted with acetic anhydride (200 μL), pyridine (200 μL) and catalytic DMAP (5 mg). The reaction was stirred at room temperature for 2 h, diluted with $CH_2Cl_2$, washed with saturated aqueous NaHCO$_3$, H$_2$O and brine, dried over Na$_2$SO$_4$, filtered and concentrated. Purification by flash silica column chromatography gave 0.287 g (94%) of 7a as a colorless oil. $[\alpha]^{24}_D$: −19.0° (c 0.40, $CH_2Cl_2$); IR (thin film) 2941, 2865, 1741, 1648,1229 cm$^{-1}$; $^1$H-NMR (CDCl$_3$) δ 7.44 (d, J=8.23 Hz, 2H), 7.20 (d, J=8.23 Hz, 2H), 6.46 (d, J=6.10 Hz, 1H), 5.35 (dd, J=4.27, 4.88 Hz, 1H), 4.86–4.84 (m, 1H), 4.58 (d, J=11.90 Hz, 1H), 4.55 (d, J=11.90 Hz, 1H), 4.17 (dd, J=5.49, 10.70 Hz, 1H), 3.93–3.88 (m, 3H), 2.07 (s, 3H), 1.11–0.99 (m, 21H); $^{13}$C-NMR (CDCl$_3$) δ 169.9, 145.1, 137.5, 131.6, 129.5, 121.6, 98.9, 77.0, 70.4, 69.0, 67.5, 61.6, 21.2, 18.1, 12.1; FAB MS m/z (M+Na)$^+$ calcd 535.1491, obsd 535.1502.

EXAMPLE 11

3-O-(4-Bromobenzyl)-4-O-(4-methoxybenzyl)-6-O-triisopropylsilyl-D-arabinohex-1-enitol 8. (See FIG. 2)

The procedure outlined in Example 1, using 7 (0.48 g, 1.02 mmol) and 4-methoxybenzyl chloride (0.17 mL, 1.22 mmol) gave 0.430 g (72%) of 8 as a colorless oil. $[\alpha]^{24}_D$: −13.5° (c 1.80, $CH_2Cl_2$); IR (thin film) 2941, 2846, 1647, 1513, 1247 cm$^{-1}$; $^1$H-NMR (CDCl$_3$) δ 7.45 (d, J=8.24 Hz, 2H), 7.25 (d, J=8.24 Hz, 2H), 7.21 (d, J=8.24 Hz, 2H), 6.86 (d, J=8.54 Hz, 2H), 6.40 (dd, J=1.22, 6.10 Hz, 1H), 4.81 (dd, J=2.75, 6.10 Hz, 1H), 4.76 (d, J=11.00 Hz, 1H), 4.71 (d, J=11.00 Hz, 1H), 4.58 (d, J=11.90 Hz, 1H), 4.53–4.48 (m, 2H), 4.17–4.15 (m, 1H), 4.02–3.98 (m, 2H), 3.92–3.90 (m, 2H), 3.81 (s, 3H), 1.13–1.06 (m, 21H); $^{13}$C-NMR (CDCl$_3$) δ 159.5, 145.1, 137.8, 131.7 (2 lines), 130.7, 129.8, 129.6 (2 lines), 129.5, 121.6, 114.0, 99.6, 78.3, 76.0, 73.8, 73.7, 72.1, 71.2, 70.0, 62.1, 55.5, 18.2 (2 lines), 12.2; FAB MS m/z (M+Na)$^+$: calcd 613.1961, obsd 613.1946.

EXAMPLE 12

4-O-(4-Methoxybenzyl)-3-O-(4-(N-methyl-N-phenylamino)benzyl)-6-O-triisopropylsilyl-D-arabino-hex-1-enitol 8a.

The general procedure outlined in Example 2, using 8 (0.15 g, 0.250 mmol), Pd$_2$(dba)$_3$ (2.4 mg, 0.0026 mmol), (o-biphenyl)P(t-Bu)$_2$ (3.0 mg, 0.010 mmol), NaOtBu (34.0 mg, 0.350 mmol) gave 0.152 g (99%) of 8a as a yellow oil. $[\alpha]^{24}_D$: −11.8° (c 0.76, $CH_2Cl_2$); IR (thin film) 2938, 1595, 1513, 1065 cm$^{-1}$; $^1$H-NMR (CDCl$_3$) δ 7.30–7.25 (m, 6H), 7.03 (d, J=7.61 Hz, 2H), 7.00–6.97 (m, 3H), 6.87 (d, J=8.54 Hz, 2H), 6.39 (dd, J=1.22, 6.10 Hz, 1H), 4.84 (dd, J=2.44, 6.10 Hz, 1H), 4.81 (d, J=11.0 Hz, 1H), 4.70 (d, J=11.0 Hz, 1H), 4.58 (d, J=11.3 Hz, 1H), 4.53 (d, J=11.3 Hz, 1H), 4.20–4.18 (m, 1H), 4.05–3.98 (m, 2H), 3.93–3.91 (m, 2H), 3.80 (s, 3H), 3.32 (s, 3H), 1.13–1.06 (m, 21H); $^{13}$C-NMR (CDCl$_3$) δ 159.4, 149.1, 148.8, 144.9, 131.2, 130.9, 129.8, 129.4, 129.3, 121.6, 120.8, 120.3, 114.0, 100.0, 78.4, 75.7, 73.9, 73.7, 70.7, 62.2, 55.5, 40.5, 18.2 (2 lines), 12.2; FAB MS m/z (M)$^+$: calcd 617.3567, obsd 617.3540.

EXAMPLE 13

Figure 4:
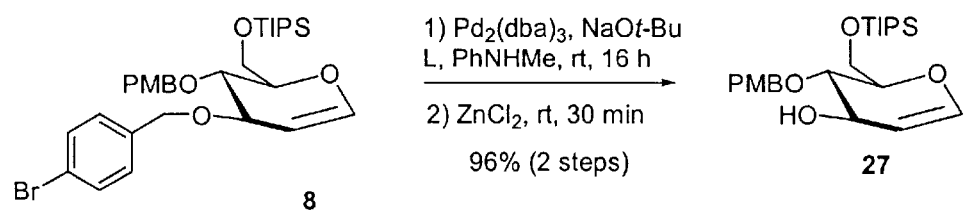
FIG. 4 depicts the selective removal of a protecting group of the present invention from an orthogonally-protected D-glucal.

4-O-(4-Methoxybenzyl)-6-O-triisopropylsilyl-D-arabino-hex-1-enitol 27. (See FIG. 4)

The general procedure outlined in Example 4, using 8a (54.8 mg, 0.080 mmol) and ZnCl$_2$ (80 μL 1.0 M in Et$_2$O, 0.080 mmol) gave 34.6 mg (97%) of 27 as a colorless oil. $[\alpha]^{24}_D$: +11.4° (c 0.59, $CH_2Cl_2$); IR (thin film) 3372, 2940, 2865, 1649, 1514 cm$^{-1}$; $^1$H-NMR (CDCl$_3$) δ 7.31 (d, J=8.54 Hz, 2H), 6.89 (d, J=8.54 Hz, 2H), 6.36 (dd, J=1.22, 6.10 Hz, 1H), 4.76–4.70 (m, 3H), 4.20–4.27 (m, 1H), 4.05 (d, J=2.44 Hz, 2H), 3.86–3.84 (m, 2H), 3.81 (s, 3H), 3.73–3.70 (m, 2H), 2.17 (d, J=5.80 Hz, 1H), 1.13–1.06 (m, 21H); $^{13}$C-NMR (CDCl$_3$) δ 159.6, 144.8, 130.8, 129.8, 114.2, 102.2, 77.9, 76.9, 73.6, 68.4, 62.7, 55.5, 18.2, 18.1, 12.2; FAB MS m/z (M+Na)$^+$: calcd 445.2386, obsd 445.2396.

EXAMPLE 14

3,4-Di-O-benzyl-6-O-(4-bromobenzyl)-D-arabino-hex-1-enitol 10. (See FIG. 3)

The general procedure outlined in Example 1, using 9 (3.54 g, 10.8 mmol) and 4-bromobenzyl bromide (2.98 g, 11.9 mmol) gave 4.67 g (85%) of 10 as a colorless oil. $[\alpha]^{24}_D$: +8.6° (c 0.58, $CH_2Cl_2$); IR (thin film) 2862, 1647, 1453, 1238, 1069 cm$^{-1}$; $^1$H-NMR (CDCl$_3$) δ 7.47 (d, J=8.24 Hz, 2H), 7.37–7.26 (m, 10H), 7.22 (d, J=7.93 Hz, 2H), 6.46 (dd, J=0.92, 6.10 Hz, 1H). 4.92 (dd, J=2.75, 6.41 Hz, 1H), 4.88 (d, J=11.6 Hz, 1H). 4.68 (d, J=11.60 Hz, 1H), 4.67 (d, J=11.30 Hz, 1H), 4.58 (d, J=11.60 Hz, 1H), 4.56 (d, J=12.20 Hz, 1H), 4.52 (d, J=12.20 Hz, 1H), 4.26–4.23 (m, 1H), 4.11–4.07 (m, 1H), 3.88–3.86 (m, 1H), 3.83 (dd, J=5.19, 10.70 Hz, 1H), 3.77 (dd, J=2.44, 10.70 Hz, 1H); $^{13}$C-NMR (CDCl$_3$) δ 144.8, 138.4, 138.3, 138.2, 131.6, 129.5, 128.6, 128.0 (2 lines), 127.8, 121.7, 100.1, 76.8, 75.8, 74.5, 73.9, 72.8, 70.6, 68.8; FAB MS m/z (M+Na)$^+$: calcd 517.0990, obsd 517.0993.

EXAMPLE 15

Methyl 3,4-di-O-benzyl-6-O-(4-bromobenzyl)-β-D-glucopyranoside 10a.

A solution of 10 (4.67 g, 9.20 mmol) in $CH_2Cl_2$ (5 mL) was cooled to 0° C. and dimethyldioxirane (115 mL 0.08 M in acetone, 9.20 mmol) was added. After 10 min, the solvent was removed in vacuo and 10 mL MeOH/5 mL $CH_2Cl_2$ were added. The reaction was warmed to room temperature over 4 h. The solvent was removed in vacuo to afford 4.37 g (94%) of 10a as a white solid. $[\alpha]^{24}_D$: +9.7° (c 2.29, $CH_2Cl_2$); IR (thin film) 3444, 2865, 1452, 1357, 1061 cm$^{-1}$; $^1$H-NMR (CDCl$_3$) δ 7.47 (d, J=8.24 Hz, 2H), 7.41–7.31 (m, 8H), 7.24–7.19 (m, 4H), 4.96 (d, J=11.30 Hz, 1H), 4.88 (d, J=11.60 Hz, 2H), 4.60–4.49 (m, 3H), 4.21 (d, J=7.63 Hz, 1H), 3.77–3.69 (m, 2H), 3.64–3.50 (m, 7H), 2.55 (d, J=1.83 Hz, 1H); $^{13}$C-NMR (CDCl$_3$) δ 138.7, 138.1, 137.3, 131.6, 129.5, 128.7, 128.6, 128.1, 128.0 (2 lines), 127.9, 121.6, 103.8, 84.6, 77.7, 75.3, 75.2 (2 lines), 74.8, 72.8, 69.0, 57.3; FAB MS m/z (M+Na)$^+$: calcd 565.1202, obsd 565.1210.

EXAMPLE 16

Methyl 3,4-di-O-benzyl-6-O-(4-bromobenzyl)-2-O-(4-chlorobenzyl)-β-D-glucopyranoside 12. (See FIG. 3)

The general procedure outlined in Example 1, using 10a (0.795 g, 1.46 mmol) and 4-chlorobenzylbromide (0.331 g, 1.61 mmol) gave 0.825 g (85%) of 12 as a white solid. $[\alpha]^{24}_D$: +24.0° (c 0.94, $CH_2Cl_2$); IR (thin film) 2862, 1490, 1358, 1070 cm$^{-1}$; $^1$H-NMR (CDCl$_3$) δ 7.45 (d, J=8.54 Hz, 2H), 7.33–7.26 (m, 12H), 7.22 (d, J=8.24 Hz, 2H), 7.18–7.15 (m, 2H), 4.90–4.80 (m, 4H), 4.67 (d, J=11.30 Hz, 1H), 4.58–4.48 (m, 3H), 4.30 (d, J=7.63 Hz, 1H), 3.73 (dd, J=2.14, 11.00 Hz, 1H), 3.70–3.59 (m, 3H), 3.58 (s, 3H), 3.48–3.45 (m, 1H), 3.41 (dd, J=7.93, 8.85, 1H); $^{13}$C-NMR (CDCl$_3$) δ 138.6, 138.2, 137.3, 137.2, 133.6, 131.7, 129.6 (2 lines), 128.7 (2 lines), 128.6, 128.1 (2 lines), 127.9 (2 lines), 121.7, 104.8, 84.8, 82.3, 78.0, 75.9, 75.2, 75.0, 74.0, 72.9, 69.1, 57.3; FAB MS m/z (M+Na)$^+$: calcd 689.1281, obsd 689.1267.

EXAMPLE 17

Methyl 3,4-di-O-benzyl-2-O-(2-bromobenzyl)-6-O-(4-bromobenzyl)-β-D-glucopyranoside 13. (See FIG. 3)

The general procedure outlined in Example 1, using 10a (4.67 g, 9.20 mmol) and 2-bromobenzylbromide (2.53 g, 10.1 mmol) gave 5.63 g (86%) of 13 as a white solid. [α]$^{24}_D$: +8.0° (c 0.56, CH$_2$Cl$_2$); IR (thin film) 2861, 1453, 1358, 1070 cm$^{-1}$; $^1$H-NMR (CDCl$_3$) δ 7.56–7.52 (m, 2H), 7.46 (d, J=8.24 Hz, 2H), 7.32–7.14 (m, 14H), 5.04 (d, J=12.50 Hz, 1H), 4.94 (d, J=11.00 Hz, 1H), 4.87–4.79 (m, 3H), 4.60–4.50 (m, 3H), 4.35 (d, J=7.63 Hz, 1H), 3.77–3.68 (m, 3H), 3.64–3.58 (m, 4H), 3.51–3.48 (m, 2H), $^{13}$C-NMR (CDCl$_3$) δ 138.6, 138.2, 137.4, 132.7, 131.6, 129.8, 129.5, 129.1, 128.6 (2 lines), 128.1 (2 lines), 128.0, 127.9, 127.8, 127.5, 122., 121.6. 104.8, 84.7, 82.6, 78.0, 75.9, 75.2, 75.0, 73.8, 72.8, 69.1, 57.4; FAB MS m/z (M+Na)$^+$: calcd 733.0776, obsd 733.0765.

EXAMPLE 18

3,4-Di-Obenzyl-6-O-(4-chlorobenzyl)-D-arabino-hex-1-enitol 11. (See FIG. 3)

The general procedure outlined in Example 1, using 9 (1.66 g, 5.09 mmol) and 4-chlorobenzyl bromide (1.15 g, 5.60 mmol) gave 2.34 g (98%) of 11 as a colorless oil. [α]$^{24}_D$: +3.6° (c 1.08, CH$_2$Cl$_2$); IR (thin film) 2865, 1648, 1492, 1238, 1090 cm$^{-1}$; $^1$H-NMR (CDCl$_3$) δ 7.36–7.30 (m, 10H), 7.28–7.26 (m, 4H), 6.45 (dd, J=0.92, 6.10 Hz, 1H), 4.91 (dd, J=2.75, 6.10 Hz, 1H), 4.87 (d, J=11.30 Hz, 1H), 4.67 (d, J=11.90 Hz, 1H), 4.66 (d, J=11.30 Hz, 1H), 4.58 (d, J=11.60 Hz, 1H), 4.56 (d, J=12.20 Hz, 1H), 4.53 (d, J=12.20 Hz, 1H), 4.25–4.23 (m, 1H), 4.10–4.07 (m, 1H), 3.89–3.87 (m, 1H), 3.82 (dd, J=5.18, 10.70 Hz, 1H), 3.76 (dd, J=2.75, 10.70 Hz, 1H); $^{13}$C-NMR (CDCl$_3$) δ 144.8, 138.4, 138.3, 136.7, 133.5, 129.2, 128.7, 128.6, 128.0 (2 lines), 127.9 (2 lines), 100.2, 76.8, 75.9, 74.5, 73.9, 72.8, 70.7, 68.8; FAB MS m/z (M+Na)$^+$: calcd 473.1496, obsd 473.1485.

EXAMPLE 19

Methyl 3,4-di-O-benzyl-6-O-(4-chlorobenzyl)-β-D-glucopyranoside 11a.

A solution of 11 (1.95 g, 4.30 mmol) in CH$_2$Cl$_2$ (5 mL) was cooled to 0° C. and dimethyldioxirane (54.0 mL 0.08 M in acetone, 4.33 mmol) was added. After 10 min, the solvent was removed in vacuo and 10 mL MeOH/5 mL CH$_2$Cl$_2$ were added. The reaction was warmed to room temperature over 4 h. The solvent was removed in vacuo to afford 2.08 g (96%) of 11a as a white solid. [α]$^{24}_D$: +5.7° (c 0.79, CH$_2$Cl$_2$); IR (thin film) 3443, 2866, 1491, 1453, 1060 cm$^{-1}$; $^1$H-NMR (CDCl$_3$) δ 7.39–7.26 (m, 12H), 7.19–7.18 (m, 2H), 4.93 (d, J=11.00 Hz, 1H), 4.88–4.84 (m, 2H), 4.58 (d, J=12.20 Hz, 1H), 4.54 (d, J=11.00 Hz, 1H), 4.51 (d, J=12.50 Hz, 1H), 4.19 (d, J=7.63 Hz, 1H), 3.76–3.68 (m, 2H), 3.64–3.58 (m, 2H), 3.57 (s, 3H), 3.56–3.48 (m, 2H), 2.37 (d, J=2.14 Hz, 1H); $^{13}$C-NMR (CDCl$_3$) δ 138.7, 138.1, 137.8, 133.6, 129.3 (2 lines), 128.7 (2 lines), 128.6, 128.1, 128.0 (2 lines), 103.9, 84.6, 77.8, 75.4, 75.3, 75.2, 74.8, 72.9, 57.4; FAB MS m/z (M+Na)$^+$: calcd 521.1707, obsd 521.1696.

EXAMPLE 20

Methyl 3.4-di-O-benzyl-2-O-(2-bromobenzyl)-6-O-(4-chlorobenzyl)-β-D-glucopyranoside 14. (See FIG. 3)

The general procedure outlined in Example 1, using 11a (1.03 g, 2.06 mmol) and 2-bromobenzylbromide (0.567 g, 2.27 mmol) gave 1.10 g (80%) of 14 as a white solid. [α]$^{24}_D$: +7.2° (c 0.71, CH$_2$Cl$_2$); IR (thin film) 2904, 1491, 1453, 1353, 1358, 1071 cm$^{-1}$; $^1$H-NMR (CDCl$_3$) δ 7.55–7.52 (m, 2H), 7.32–7.26 (m, 13H), 7.19–7.13 (m, 3H), 5.04 (d, J=12.50 Hz, 1H), 4.93 (d, J=11.00 Hz, 1H), 4.86–4.78 (m, 3H), 4.61–4.51 (m, 3H), 4.35 (d, J=7.63 Hz, 1H), 3.76–3.60 (m, 4H), 3.58 (s, 3H), 3.51–3.47 (m, 2H); $^{13}$C-NMR (CDCl$_3$) δ 138.6, 138.2, 136.9, 133.5, 132.7, 129.8, 129.2, 129.1, 128.7, 128.6, 128.5, 128.1 (2 lines), 128.0, 127.8, 127.5, 122.9, 104.8, 84.8, 82.6, 78.0, 75.9, 75.2, 75.0, 73.9, 72.8, 69.1, 57.4; FAB MS m/z (M+Na)$^+$: calcd 689.1281, obsd 689.1274.

EXAMPLE 21

Methyl 3.4-di-O-benzyl-2-O-(2-chlorobenzyl)-6-O-(4-chlorobenzyl)-β-D-glucopyranoside 15. (See FIG. 3)

The general procedure outlined in Example 1, using 11a (1.03 g, 2.06 mmol) and 2-chlorobenzylbromide (0.295 mL, 2.27 mmol) gave 1.10 g (86%) of 15 as a white solid. [α]$^{24}_D$: +10.4° (c 0.46, CH$_2$Cl$_2$); IR (thin film) 2861, 1453, 1071, 751 cm$^{-1}$; $^1$H-NMR (CDCl$_3$) δ 7.53–7.51 (m, 1H), 7.36–7.26 (m, 13H), 7.24–7.12 (m, 2H), 5.06 (d, J=12.20 Hz, 1H), 4.92 (d, J=11.00 Hz, 1H), 4.84 (d, J=11.60 Hz, 2H), 4.78 (d, J=11.00 Hz, 1H), 4.58 (d, J=12.50 Hz, 1H), 4.53 (d, J=11.00 Hz, 1H), 4.52 (d, J=12.20 Hz, 1H), 4.33 (d, J=7.62 Hz, 1H), 3.76–3.59 (m, 4H), 3.58 (s, 3H), 3.50–3.46 (m, 2H); $^{13}$C-NMR (CDCl$_3$) δ 138.7, 138.2, 136.9, 136.5, 133.5, 133.2, 129.8, 129.5, 129.2, 128.9, 128.7, 128.6, 128.5, 128.1 (2 lines), 128.0, 127.8, 126.9, 104.8, 84.7, 82.6, 78.0, 75.9, 75.2, 75.0, 72.9, 71.6, 69.2, 57.4; FAB MS m/z (M+Na)$^+$: calcd 645.1787, obsd 645.1771.

EXAMPLE 22

6-O-(4-(N-Benzylamino)benzyl)-1,2:3,4-di-O-isopropylidene-α-D-galactopyranoside 16. (See FIG. 6)

The general procedure outlined in Example 2, using 2 (0.214 g, 0.50 mmol), Pd$_2$(dba)$_3$ (2.4 mg, 0.0026 mmol), (o-biphenyl)P(t-Bu)$_2$ (3.0 mg, 0.010 mmol), NaOtBu (68.0 mg, 0.70 mmol) gave 0.206 g (91%) of 16 as a yellow oil. [α]$^{24}_D$: −24.3° (c 1.35, CH$_2$Cl$_2$); IR (thin film) 3405, 2985, 2933, 1615, 1523 cm$^{-1}$; $^1$H-NMR (CDCl$_3$) δ 7.39–7.34 (m, 3H), 7.30–7.26 (m, 1H), 7.17 (d, J=8.54 Hz, 2H), 6.61 (d, J=8.54 Hz, 2H), 5.56 (d, J=4.88 Hz, 1H), 4.60 (dd, J=2.44, 7.93, 1H), 4.50 (d, J=11.30 Hz, 1H), 4.44 (d, J=11.60 Hz, 1H), 4.34 (s, 2H), 4.31 (dd, J=2.44, 5.19 Hz, 1H), 4.28 (dd, J=2.14, 7.93 Hz, 1H), 4.10 (s, 3H), 3.99 (dt, J=1.83, 6.41 Hz, 1H), 3.68–3.59 (m, 2H), 1.54 (s, 3H), 1.46 (s, 3H), 1.35 (s, 3H), 1.34 (s, 3H); $^{13}$C-NMR (CDCl$_3$) δ 147.9, 139.5, 128.7, 128.8, 127.6, 127.4, 127.3, 112.8, 109.3, 108.6, 96.5, 73.5, 71.3, 70.8, 68.4, 67.0, 48.4, 26.3, 26.2, 25.1, 24.6; FAB MS m/z (M)$^+$: calcd 455.2308, obsd 455.2303.

EXAMPLE 23

6-O-(4-(N-Methyl-N-phenylamino)benzyl)-1,2:3,4-di-O-isopropylidene-α-D-galactopyranoside 17. (See FIG. 6)

The general procedure outlined in Example 2, using 2 (0.214 g, 0.50 mmol), Pd$_2$(dba)$_3$ (2.4 mg, 0.0026 mmol), (o-biphenyl)P(t-Bu)$_2$ (3.0 mg, 0.010 mmol), NaOtBu (68.0 mg, 0.70 mmol) gave 0.219 g (96%) of 17 as a yellow oil. [α]$^{24}_D$: −52.4° (c 2.04, CH$_2$Cl$_2$); IR (thin film) 2985, 2933, 1594, 1497, 1069 cm$^{-1}$; $^1$H-NMR (CDCl$_3$) δ 7.30–7.26 (m, 4H), 7.04–6.95 (m, 5H), 5.57 (d, J=5.19 Hz, 1H), 4.62 (dd, J=2.44, 7.93 Hz, 1H), 4.58 (d, J=11.60 Hz, 1H), 4.52 (d, J=11.90 Hz, 1H), 4.34–4.30 (m, 2H), 4.04–4.01 (m, 1H), 3.73–3.63 (m, 2H), 3.32 (s, 3H), 1.56 (s, 3H), 1.48 (s, 3H), 1.37 (s, 3H), 1.35 (s, 3H); $^{13}$C-NMR (CDCl$_3$) δ 149.1, 148.7, 131.1, 129.3, 129.2, 121.4, 120.5, 120.4, 109.3, 108.7, 96.5, 73.2, 71.3, 70.8 (2 lines), 68.7, 67.0, 40.4, 26.3, 26.2, 25.1, 24.6; FAB MS m/z (M)$^+$: calcd 455.2308, obsd 455.2299.

EXAMPLE 24

6-O-(4-(N-Hexylamino)benzyl)-1,2:3,4-di-O-isopropylidene-α-D-galactopyranoside 18. (See FIG. 6)

The general procedure outlined in Example 2, using 2 (0.214 g, 0.50 mmol), Pd$_2$(dba)$_3$ (4.6 mg, 0.005 mmol), (o-biphenyl)P(t-Bu)$_2$ (6.0 mg, 0.020 mmol), NaOtBu (68.0 mg, 0.70 mmol) gave 0.174 g (78%) as a 2:1 mixture of mono-arylated (18) and diarylated (18a) hexylamines. 18: [α]$^{24}_D$: −50.6° (c 1.17, CH$_2$Cl$_2$); IR (thin film) 3392, 2929, 1615, 1523, 1069 cm$^{-1}$; $^1$H-NMR (CDCl$_3$) δ 7.16 (d, J=8.54 Hz, 2H), 6.56 (d, J=8.54 Hz, 2H), 5.54 (d, J=4.88 Hz, 1H), 4.59 (dd, J=2.44, 7.93 Hz, 1H), 4.48 (d, J=11.30 Hz, 1H), 4.43 (d, J=11.30 Hz, 1H), 4.30 (dd, J=2.44, 4.88 Hz, 1H), 4.27 (dd, J=1.83, 7.93 Hz, 1H), 3.99–3.95 (m, 1H), 3.67–3.57 (m, 3H), 3.10 (t, J=7.32 Hz, 2H), 1.64–1.54 (m, 2H), 1.53 (s, 3H), 1.45 (s, 3H), 1.43–1.29 (m, 12H), 0.92–0.89 (m, 3H); $^{13}$C-NMR (CDCl$_3$) δ 148.4, 129.7, 126.7, 112.6, 109.3, 108.6, 96.5, 73.5, 71.3, 70.8, 68.3, 67.0, 44.2, 31.8, 29.7, 27.0, 26.3, 26.2, 25.1, 24.6, 22.8, 14.2; FAB MS m/z (M+Na)$^+$: calcd 472.2675, obsd 472.2679. 18a: [α]$^{24}_D$: −49.9° (c 1.69, CH$_2$Cl$_2$); IR (thin film) 2930, 1606, 1510, 1371, 1070 cm$^{-1}$; $^1$H-NMR (CDCl$_3$) δ 7.23 (d, J=8.54 Hz, 4H), 6.94 (d, J=8.54 Hz, 4H), 5.55 (d, J=5.19 Hz, 2H), 4.60 (dd, J=2.44, 7.93 Hz, 2H), 4.55 (d, J=11.90 Hz, 2H), 4.49 (d, J=11.60 Hz, 2H), 4.32–4.28 (m, 4H), 4.01 (dt, J=(1.53, 6.10 Hz, 2H), 3.71–3.61 (m, 6H), 1.65–1.62 (m, 2H), 1.55 (s, 6H), 1.46 (s, 6H), 1.35 (s, 6H), 1.34 (s, 6H), 1.34–1.25 (m, 8H), 0.88 (t, J=6.67 Hz, 3H); $^{13}$C-NMR (CDCl$_3$) δ 147.7, 130.9, 129.3, 120.8, 109.4, 108.7, 96.6, 73.3, 71.3, 70.8 (2 lines), 68.7, 67.0, 52.6, 31.8, 27.5, 26.9, 26.3, 26.2, 25.1, 24.6, 22.9, 14.2; FAB MS m/z (M)$^+$: calcd 797.4350, obsd 797.4356.

EXAMPLE 25

6-O-(4-(N-Morpholino)benzyl)-1,2:3,4-di-O-isopropylidene-α-D-galactopyranoside 19. (See FIG. 6)

The general procedure outlined in Example 3, using 3 (0.192 g, 0.50 mmol), Pd(OAc)$_2$ (2.2 mg, 0.001 mmol), (o-biphenyl)P(t-Bu)$_2$ (6.0 mg, 0.020 mmol), NaOtBu (68.0 mg, 0.70 mmol) gave 0.206 g (95%) of 19 as a yellow oil. [α]$^{24}_D$: −44.5° (c 1.31, CH$_2$Cl$_2$); IR (thin film) 2984, 1724, 1681, 1517, 1069 cm$^{-1}$; $^1$H-NMR (CDCl$_3$) δ 7.26 (d, J=8.55 Hz, 2H), 6.87 (d, J=8.55 Hz, 2H), 5.44 (d, J=5.17 Hz, 1H), 4.58 (dd, J=2.14, 7.93 Hz, 1H), 4.53 (d, J=11.60 Hz, 1H), 4.47 (d, J=11.60 Hz, 1H), 4.30 (dd, J=1.83, 4.88 Hz, 1H), 4.26 (dd, J=1.53, 7.93 Hz, 1H), 3.99–3.95 (m, 1H), 3.85 (t, J=4.88 Hz, 4H), 3.67–3.57 (m, 2H), 3.14 (t, J=4.88 Hz, 4H), 1.52 (s, 3H), 1.44 (s, 3H), 1.33 (s, 3H), 1.32 (s, 3H); $^{13}$C-NMR (CDCl$_3$) δ 151.1, 129.8, 129.3, 115.7, 109.3, 108.6, 96.5, 73.1, 71.3, 70.7 (2 lines), 68.6, 67.0 (2 lines), 49.5, 26.2, 26.1, 25.1, 24.6; FAB MS m/z (M)$^+$: calcd 435.2257, obsd 435.2247.

EXAMPLE 26

6-O-(2-(N-benzylamino)benzyl)-1,2:3,4-di-O-isopropylidene-α-D-galactopyranoside 20. (See FIG. 6)

The general procedure outlined in Example 2, using 4 (0.214 g, 0.50 mmol), Pd$_2$(dba)$_3$ (4.6 mg, 0.005 mmol), (o-biphenyl)P(t-Bu)$_2$ (6.0 mg, 0.020 mmol), NaOtBu (68.0 mg, 0.70 mmol) gave 0.162 g (76%) of 20 as a yellow oil. [α]$^{24}_D$: −45.0° (c 0.18, CH$_2$Cl$_2$); IR (thin film) 3397, 2987, 2931, 1610, 1518 cm$^{-1}$; $^1$H-NMR (CDCl$_3$) δ 7.39 (d, J=7.63 Hz, 2H), 7.33 (t, J=7.32 Hz, 1H), 7.27–7.24 (m, 1H), 7.15 (dt, J=1.53, 7.93 Hz, 1H), 7.11 (dd, J=1.53, 7.32 Hz, 1H), 6.66 (dt, J=0.92, 7.32 Hz, 1H), 6.58 (d, J=7.93 Hz, 1H), 5.53–5.48 (m, 2H), 4.66 (d, J=11.30 Hz, 1H), 4.62 (d, J=11.00 Hz, 1H), 4.59 (dd, J=2.44, 7.93 Hz, 1H), 4.45 (d, J=4.88 Hz, 2H), 4.32 (dd, J=2.44, 5.19 Hz, 1H), 4.22 (dd, J=1.83, 7.93 Hz, 1H), 4.03–3.99 (m, 1H), 3.73–3.65 (m, 2H), 1.47 (s, 3H), 1.46 (s, 3H), 1.32 (s, 3H), 1.29 (s, 3H); $^{13}$C-NMR (CDCl$_3$) δ 147.8, 140.1, 130.1, 129.8, 128.6, 127.1, 126.9, 121.7, 116.4, 111.0, 109.5, 108.7, 96.5, 73.2, 71.3, 70.8, 70.6, 68.5, 66.8, 47.5, 26.2 (2 lines), 25.1, 24.7; FAB MS m/z (M)$^+$: calcd 455.2308, obsd 455.2294.

EXAMPLE 27

Dibutyl 2-O-pivaloyl-3,4,6-tri-O-benzyl-β-D-glucopyranoside phosphate 22. (See FIG. 5, and Plante, O. J.; Andrade, R. B.; Seeberger, P. H. *Organic Lett.* 1999, 1, 211).

3,4,6-Tri-O-benzylglucal (1.12 g, 2.70 mmol) was dissolved in CH$_2$Cl$_2$ (5 mL) and cooled to 0° C. A 0.08 M solution of dimethyldioxirane in acetone (51 mL, 4.06 mmol) was added and the reaction was stirred for 15 min. After the solvent was removed in a stream of N$_2$ and the remaining residue dried in vacuo for 15 min at 0° C., 20 mL CH$_2$Cl$_2$ were added. The solution was cooled to −78° C. for 15 min. Dibutylphosphate (0.563 mL, 1.06 mmol) was added dropwise over 5 min. After complete addition, the reaction was warmed to 0° C. and DMAP (1.32 g, 10.8 mmol) and pivaloyl chloride (0.665 mL, 5.40 mmol) were added. The solution was warmed to room temperature over 1 h. The solvent was removed in vacuo and the residue was purified by flash silica column chromatography to afford 1.74 g (89%) of 22 as a colorless oil. [α]$^{24}_D$: −1.9° (c 1.50, CH$_2$Cl$_2$); IR (thin film) 2946, 1740, 1454, 1282, 1016 cm$^1$; $^1$H-NMR (CDCl$_3$) δ 7.33–7.25 (m, 13H), 7.16–7.14 (m, 2H), 5.24 (dd, J=7.25, 7.25 Hz, 1H), 5.17 (dd, J=8.50, 8.50 Hz, 1H), 4.80–4.75 (m, 2H), 4.70 (d, J=11.00 Hz, 1H), 4.69–4.54 (m, 2H), 4.51 (d, J=11.00 Hz, 1H), 4.08–4.00 (m, 4H), 3.82 (dd, J=9.50, 9.50 Hz, 1H), 3.78–3.70 (m, 3H), 3.64–3.61 (m, 1H), 1.64–1.59 (m, 4H), 1.40–1.34 (m, 4H), 1.20 (s, 9H), 0.96–0.88 (m, 6H); $^{13}$C-NMR (CDCl$_3$) δ 177.2, 138.2, 138.1, 128.7, 128.3, 128.2, 128.1, 128.0, 127.6, 97.0, 96.5, 83.1, 76.2, 75.9, 73.9, 73.3, 68.4, 68.2, 68.1, 39.2, 32.7, 26.9, 19.1, 14.0; $^{31}$P-NMR (CDCl$_3$) δ −2.2; FAB MS m/z (M$^+$) calcd 726.3532, obsd 726.3537.

EXAMPLE 28

Methyl 3,4-di-O-benzyl-6-O-(4-(N-benzylamino)benzyl)-2-O-(4-chlorobenzyl)-β-D-glucopyranoside 12a. (See FIG. 5)

The general procedure outlined in Example 2, using 12 (0.167 g, 0.25 mmol), Pd$_2$(dba)$_3$ (1.2 mg, 0.0013 mmol), (o-biphenyl)P(t-Bu)$_2$ (1.5 mg, 0.005 mmol), NaOtBu (34.0 mg, 0.70 mmol) at 80° C. for 5 h gave 0.154 g (92%) as 16:1 mixture of monoaminated (12a) and diaminated (12b) products. 12a: [α]$^{24}_D$: +16.8° (c 1.46, CH$_2$Cl$_2$); IR (thin film) 2866, 1616, 1522, 1071 cm$^{-1}$; $^1$H-NMR (CDCl$_3$) δ 7.37–7.26 (m, 17H), 7.18–7.14 (m, 4H), 6.60 (d, J=8.54 Hz, 2H), 4.89–4.78 (m, 2H), 4.67 (d, J=11.30 Hz, 1H), 4.59–4.49 (m, 3H), 4.43 (d, J=11.60 Hz, 1H), 4.33–4.28 (m, 3H), 4.06 (br s, 1H), 3.73–3.57 (m, 8H), 3.46–3.40 (m, 2H); $^{13}$C-NMR (CDCl$_3$) δ 148.1, 139.5, 138.8, 138.3, 137.3, 133.5, 129.9, 129.6, 129.0, 128.8 (2 lines), 128.7, 128.6, 128.3, 128.2 (2 lines), 127.9 (2 lines), 127.8, 127.6, 127.4, 127.0, 112.8, 104.8, 84.8, 82.3, 78.1, 75.8, 75.2, 75.1, 74.0, 73.7, 68.2, 57.3, 48.5; FAB MS m/z (M)$^+$: calcd 693.2857, obsd 693.2866. 12b: [α]$^{24}_D$: +23.6° (c 1.47, CH$_2$Cl$_2$); IR (thin film) 3404, 2866, 1615, 1522, 1066 cm$^{-1}$; $^1$H-NMR (CDCl$_3$) δ 7.40–7.27 (m, 18H), 7.21–7.16 (m, 6H), 6.62–6.58 (m, 4H), 4.97 (d, J=11.00 Hz, 1H), 4.82–4.77 (m, 2H), 4.61 (d, J=10.40 Hz, 1H), 4.56–4.43 (m, 3H), 4.34–4.30 (m, 4H), 4.08 (br s, 2H), 3.72–3.58 (m, 7H), 3.46–3.44 (m, 2H); $^{13}$C-NMR (CDCl$_3$) δ 148.1 (2 lines), 139.6, 139.5, 139.0, 138.4, 130.2, 130.0, 129.0, 128.9, 128.8, 128.7, 128.6 (2 lines), 128.3, 128.2, 128.1, 127.9, 127.7 (3 lines), 127.6, 127.5, 127.4, 112.9, 112.8, 105.0, 84.8, 82.1, 78.1, 75.8, 75.2, 75.0, 73.7, 68.4, 57.4, 48.5, 47.5; FAB MS m/z (M+Na)$^+$: calcd 787.3223, obsd 787.3714.

EXAMPLE 29

Methyl 3,4-di-O-benzyl-2-O-(4-chlorobenzyl)-β-D-glucopyranoside 21. (See FIG. 5)

The general procedure outlined in Example 4, using 12a (0.167 g, 0.25 mmol) and SnCl$_4$ (0.25 mL 1.0 M in heptane, 0.25 mmol) gave 0.112 g (89%) of 21 as a white solid. $[\alpha]^{24}_D$: +13.9° (c 3.00, CH$_2$Cl$_2$); IR (thin film) 3355, 2909, 1492, 1452, 1070 cm$^{-1}$; $^1$H-NMR (CDCl$_3$) δ 7.38–7.29 (m, 14H), 4.94–4.86 (m, 4H), 4.71 (d, J=11.60 Hz, 1H), 4.70 (d, J=10.70 Hz, 1H), 4.39 (d, J=7.63 Hz, 1H), 3.95–3.91 (m, 1H), 3.80–3.75 (m, 1H), 3.72–3.60 (m, 5H), 3.44–3.40 (m, 2H), 2.12 (dd, J=5.80, 7.63 Hz, 1H); $^{13}$C-NMR (CDCl$_3$) δ 138.6, 138.1, 137.1, 133.5, 129.5, 128.7, 128.6 (2 lines), 128.2, 128.1, 127.9, 127.8, 104.8, 84.5, 82.4, 77.6, 75.8, 75.2 (2 lines), 74.0, 62.0, 57.4; FAB MS m/z (M+Na)$^+$: calcd 521.1707, obsd 521.1713.

EXAMPLE 30

Methyl 2-O-pivaloyl-3,4,6-tri-O-benzyl-β-D-glucopyranoside-(1→6)-3,4-di-O-benzyl-2-O-(4-chlorobenzyl)-β-D-glucopyranoside 23. (See FIG. 5)

Glycosyl donor 22 (0.322 g, 0.429 mmol) and glycosyl acceptor 21 (0.179 g, 0.358 mmol) were combined and azeotropically dried with toluene (3×5 mL) followed by 1 h under vacuum. The mixture was dissolved in CH$_2$Cl$_2$ and cooled to −78° C. for 15 min. TMSOTf (79 μL, 0.43 mmol) was added dropwise. After stirring for 10 min at −78° C., triethylamine (100 μL) was added. The solution was warmed to room temperature and the solvent was removed in a stream of N$_2$. The resulting crude product was purified by flash silica column chromatography (20% EtOAc/Hexanes) to afford 0.296 g (82%) of 23 as a colorless oil. $[\alpha]^{24}_D$: +° (c, CH$_2$Cl$_2$); IR (thin film) 2909, 1740, 1452, 1070 cm$^{-1}$; $^1$H-NMR (CDCl$_3$) δ 7.33–7.23 (m, 27H), 7.16–7.13 (m, 2H), 5.10 (dd, J=7.93, 9.46 Hz, 1H), 4.88–4.74 (m, 7H), 4.69–4.49 (m, 9H), 4.26 (d, J=7.93 Hz, 1H), 4.03 (dd, J=1.53, 11.6 Hz, 1H), 3.77–3.50 (m, 14H), 3.37–3.33 (m, 2H), 1.12 (s, 9H); $^{13}$C-NMR (CDCl$_3$) δ; FAB MS m/z (M$^+$+H) calcd 1037.4219, obsd 1037.4188.

EXAMPLE 31

Methyl 2-O-pivaloyl-3,4,6-tri-O-benzyl-β-D-glucopyranoside-(1→6)-3,4-di-O-benzyl-2-O-(4-(N-methyl-N-phenylamino)benzyl)-β-D-glucopyranoside 23a.

The general procedure outlined in Example 3, using 23 (0.202 g, 0.20 mmol), Pd(OAc)$_2$ (0.9 mg, 0.004 mmol, (o-biphenyl)P(t-Bu)$_2$ (2.4 mg, 0.008 mmol), NaOtBu (27 mg, 0.280 mmol) gave 0.193 g (89%) of 23a as a yellow oil along with 17 mg (9%) of the corresponding depivalated product 23b. 23a: $[\alpha]^{24}_D$: +6.7° (c 0.70, CH$_2$Cl$_2$); IR (thin film) 2870, 1740, 1594, 1496, 1067 cm$^{-1}$; $^1$H-NMR (CDCl$_3$) δ 7.36–7.25 (m, 27H), 7.18–7.16 (m, 2H), 7.05 (d, J=7.63 Hz, 2H), 7.00–6.97 (m, 3H), 5.12 (dd, J=8.24, 9.15 Hz, 1H), 4.97 (d, J=11.00 Hz, 1H), 4.87–4.52 (m, 13H), 4.31 (d, J=7.63 Hz, 1H), 4.06 (d, J=10.40 Hz, 1H), 3.80–3.64 (m, 7H), 3.61 (s, 3H), 3.55–3.52 (m, 2H), 3.43–3.33 (m, 3H), 3.32 (s, 3H), 1.22 (s, 9H); $^{13}$C-NMR (CDCl$_3$) δ 176.9, 149.1, 148.8, 138.8, 138.3 (2 lines), 138.1 (2 lines), 129.7, 129.4, 128.6 (2 lines), 128.5, 128.3, 128.1, 128.0 (4 lines), 127.8 (2 lines), 127.5, 121.6, 120.9, 120.2, 104.5, 101.1, 99.5, 84.7, 83.6, 82.2, 78.4, 78.0, 75.9, 75.7, 75.4, 75.2 (2 lines), 75.1, 74.8, 73.7, 73.1, 68.9, 67.6, 57.3, 40.4, 40.0, 27.4; FAB MS m/z (M+Na)$^+$: calcd 1108.5187, obsd 1108.5158. 23b: $[\alpha]^{24}_D$: +9.3° (c 0.73, CH$_2$Cl$_2$); IR (thin film) 3397, 2867, 1497, 1356, 1067 cm$^{-1}$; $^1$H-NMR (CDCl$_3$) δ 7.39–7.24 (m, 24H), 7.18–7.16 (m, 2H), 7.04–7.02 (m, 2H), 6.97–6.95 (m, 3H), 4.96 (d, J=11.00 Hz, 1H), 4.95 (d, J=11.00 Hz, 1H), 4.88–4.78 (m, 5H), 4.66–4.61 (m, 3H), 4.55–4.51 (m, 2H), 4.36–4.33 (m, 2H), 4.20 (dd, J=4.04, 11.60 Hz, 1H), 3.74–3.41 (m, 14H), 3.31 (s, 3H), 2.77 (br s, 1H); $^{13}$C-NMR (CDCl$_3$) δ 149.1, 148.8, 138.9, 138.7, 138.3, 138.1, 131.1, 129.7, 129.4, 128.7, 128.6 (2 lines), 128.2 (2 lines), 128.1, 128.0 (2 lines), 127.9, 127.8, 121.6, 120.9, 120.2, 104.9, 103.6, 84.7, 84.5, 82.2, 78.5, 75.9, 75.4, 75.3, 74.9, 74.6, 74.5, 73.7, 69.0, 68.5, 57.6, 40.5; FAB MS m/z (M+Na)$^+$: calcd 1024.4612, obsd 1024.4582.

EXAMPLE 32

Methyl 2-O-pivaloyl-3,4,6-tri-O-benzyl-β-D-glucopyranoside-(1→6)-3,4-di-O-benzyl-β-D-glucopyranoside 24. (See FIG. 5)

The general procedure outlined in Example 4, using 23a (0.138 g, 0.127 mmol) and SnCl$_4$ (0.13 mL 1.0 M in heptane, 0.13 mmol) gave 0.112 g (99%) of 24 as a white solid. $[\alpha]^{24}_D$: −3.5° (c 0.40, CH$_2$Cl$_2$); IR (thin film) 3454, 2870, 1739, 1453, 1061 cm$^{-1}$; $^1$H-NMR (CDCl$_3$) δ 7.40–7.26 (m, 23H), 7.18–7.16 (m, 2H), 5.13 (dd, J=8.23, 9.15 Hz, 1H), 4.93 (d, J=11.60 Hz, 1H), 4.86 (d, J=10.40 Hz, 2H), 4.78 (d, J=11.00 Hz, 1H), 4.77 (d, J=10.70 Hz, 1H), 4.70 (d, J=11.00 Hz, 1H), 4.63–4.61 (m, 3H), 4.55 (d, J=10.70 Hz, 1H), 4.52 (d, J=11.90 Hz, 1H), 4.17 (d, J=7.63 Hz, 1H), 4.06 (dd, J=1.53, 11.60 Hz, 1H), 3.79–3.75 (m, 4H), 3.69 (dd, J=9.16, 9.16 Hz, 1H), 3.61–3.50 (m, 7H), 3.43–3.39 (m, 1H), 2.40 (d, J=2.14 Hz, 1H), 1.22 (s, 9H); $^{13}$C-NMR (CDCl$_3$) δ 176.8, 138.7, 138.3, 138.2, 138.1, 138.0, 128.7, 128.6 (2 lines), 128.5 (2 lines), 128.2, 128.1, 128.0 (2 lines), 127.9, 127.8 (2 lines), 127.5, 103.4, 101.1, 84.5, 83.5, 78.1, 77.9, 75.8, 75.4, 75.3, 75.2, 75.1, 75.0, 74.7, 73.7, 73.0, 68.9, 67.5, 57.3, 39.0, 27.3; FAB MS m/z (M+Na)$^+$: calcd 913.4139, obsd 913.4118.

EXAMPLE 33

Methyl 2-O-pivaloyl-3,4,6-tri-O-benzyl-β-D-Glucopyranoside-(1→6) [2-O-acetyl-3,4,6-tri-O-benzyl-α-D-mannopyranoside-(1→2)]-3,4-di-O-benzyl-β-D-glucopyranoside 26. (See FIG. 5)

Glycosyl donor 25 (56.8 mg, 0.089 mmol) and glycosyl acceptor 24 (72.3 mg, 0.081 mmol) were combined and azeotropically dried with toluene (3×5 mL) followed by 1 h under vacuum. The mixture was dissolved in CH$_2$Cl$_2$ and trimethylsilyltriflate (0.7 μL, 0.004 mmol) was added. After stirring for 10 min at room temperature the solvent was removed under vacuum. The resulting crude product was purified by flash silica column chromatography (30% EtOAc/Hexanes) to afford 0.103 g (94%) of 26 as a white solid. $[\alpha]^{24}_D$: +8.6° (c 1.17, CH$_2$Cl$_2$); IR (thin film) 2868, 1741, 1453, 1363, 1062 cm$^{-1}$; $^1$H-NMR (CDCl$_3$) δ 7.37–7.25 (m, 37H), 7.20–7.16 (m, 3H), 7.13–7.11 (m, 2H), 7.09–7.06 (m, 2H), 5.46–5.44 (m, 2H), 5.13 (dd, J=8.24, 8.54 Hz, 1H), 4.87 (d, J=11.00 Hz, 1H), 4.81–4.58 (m, 13H), 4.56 (d, J=11.00 Hz, 1H), 4.51 (d, J=12.20 Hz, 1H), 4.46 (d, J=10.70 Hz, 1H), 4.33 (d, J=12.20 Hz, 1H), 4.24 (d, J=7.63 Hz, 1H), 4.04–4.00 (m, 4H), 3.80–3.62 (m, 7H), 3.55–3.51 (m, 2H), 2.19 (s, 3H), 1.23 (s, 9H); $^{13}$C-NMR (CDCl$_3$) δ 176.9, 170.7, 139.0, 138.5, 138.3, 138.1, 137.9, 128.6 (2 lines), 128.5, 128.4 (2 lines), 128.3, 128.2 (2 lines), 128.1 (2 lines), 128.0 (3 lines), 127.9 (3 lines), 127.7 (2 lines), 127.6, 127.5, 104.3, 101.1, 97.2, 83.5, 78.8, 77.9 (2 lines), 76.4, 76.2, 75.6, 75.4, 75.2, 75.1, 75.0, 74.3, 73.7, 73.4, 73.0, 71.7, 71.6, 68.9, 68.8, 68.5, 67.3, 57.1, 39.0, 27.3, 21.4; FAB MS m/z (M+Na)$^+$: calcd 1387.6181, obsd 1387.6136.

EXAMPLE 34
Ortho/Para Selectivity in Palladium Catalyzed Aminations of Aryl Bromides The general procedure outlined in Example 2, using 13 (FIG. 3, 0.178 g, 0.25 mmol), morpholine (24 µL, 0.275 mmol), Pd$_2$(dba)$_3$ (2.3 mg, 0.0025 mmol Pd$_2$(dba)$_3$), BINAP (4.6 mg, 0.0075 mmol), and NaOtBu (33.6 mg, 0.35 mmol) for 3 h gave 31.4 mg (18%) ortho-morpholino product 13a, 88.3 mg (50%) para-morpholino product 13b and 67.6 mg (38%) ortho,para-dimorpholino product 13c. Attempts to increase the 2.8:1 ratio of para:ortho substitution described here, by conducting the reaction at room temperature, 40° C. or 60° C., proved unsuccessful. Notably, when (o-biphenyl)P(t-Bu)$_2$ was used as a ligand, no selectivity was observed (i.e., para:ortho, ~1:1).

Methyl 3,4-di-O-benzyl-6-O-(4-bromobenzyl)-2-O-(2-(N-morpholino)benzyl)-β-D-glucopyranoside 13a:

$[\alpha]^{24}_D$: +17.7° (c 0.73, CH$_2$Cl$_2$); IR (thin film) 2851, 1490, 1451, 1068 cm$^{-1}$; $^1$H-NMR (CDCl$_3$) δ 7.52 (dd, J=1.83, 7.93 Hz, 1H), 7.47–7.46 (m, 2H), 7.33–7.26 (m, 8H), 7.23 (d, J=8.54 Hz, 2H), 7.19–7.16 (m, 2H), 7.09–7.05 (m, 2H), 5.08 (d, J=11.30 Hz, 1H), 4.93 (d, J=11.00 Hz, 1H), 4.87–4.82 (m, 3H), 4.60–4.49 (m, 3H), 4.32 (d, J=7.63 Hz, 1H), 3.83–3.62 (m, 8H), 3.57 (s, 3H), 3.52–3.47 (m, 2H), 3.01–2.96 (m, 2H), 2.87–2.82 (m, 2H); $^{13}$C-NMR (CDCl$_3$) δ 150.9, 138.6, 138.2, 137.4, 131.6, 130.0, 129.5, 128.6 (2 lines), 128.5, 128.1, 128.0, 127.9, 127.8, 123.9, 121.6, 119.3, 104.7, 85.0, 82.7, 78.1, 75.8, 75.2, 75.0, 72.9, 70.5, 69.1, 67.6, 57.2, 53.3; FAB MS m/z (M+Na)$^+$: calcd 740.2199, obsd 740.2210.

Methyl 3,4-di-O-benzyl-6-O-(4-(N-morpholino)benzyl)-2-O-(2-bromobenzyl)-β-D-glucopyranoside 13b:

$[\alpha]^{24}_D$: +6.4° (c 1.83, CH$_2$Cl$_2$); IR (thin film) 2856, 1612, 1517, 1451, 1071 cm$^{-1}$; $^1$H-NMR (CDCl$_3$) δ 7.57–7.55 (m, 2H), 7.35–7.28 (m, 11H), 7.21–7.14 (m, 3H), 6.90 (d, J=8.54 Hz, 2H), 5.07 (d, J=12.50 Hz, 1H), 4.96 (d, J=11.00 Hz, 1H), 4.88–4.82 (m, 3H), 4.63 (d, J=11.60 Hz, 1H), 4.54 (d, J=10.70 Hz, 1H), 4.51 (d, J=11.90 Hz, 1H), 4.37 (d, J=7.63 Hz, 1H), 3.89 (t, J=4.88 Hz, 4H), 3.80–3.63 (m, 4H), 3.61 (s, 3H), 3.55–3.50 (m, 2H), 3.17–3.14 (m, 4H); $^{13}$C-NMR (CDCl$_3$) δ 151.1, 138.7, 138.3, 138.2, 132.6, 129.7, 129.5, 129.4, 129.0, 128.5, 128.4, 128.1, 12.80, 127.9, 127.7, 127.6, 127.4, 122.8, 115.6, 104.7, 84.7, 82.5, 77.9, 75.8, 75.1, 75.0 (2 lines), 73.7, 73.3, 68.4, 67.0, 57.3, 49.4; FAB MS m/z (M+Na)$^+$: calcd 740.2199, obsd 740.2217.

Methyl 3,4-di-O-benzyl-6-O-(4-(N-morpholino)benzyl)-2-O-(2-(N-morpholino)benzyl)-β-D-glucopyranoside 13c:

$[\alpha]^{24}_D$: +15.8° (c 0.90, CH$_2$Cl$_2$); IR (thin film) 2853, 1752, 1612, 1451, 1068 cm$^{-1}$; $^1$H-NMR (CDCl$_3$) δ 7.54–7.52 (m, 1H), 7.32–7.26 (m, 11H), 7.18–7.15 (m, 2H), 7.09–7.06 (m, 2H), 6.88 (d, J=8.54 Hz, 2H), 5.08 (d, J=11.30 Hz, 1H), 4.92 (d, J=11.00 Hz, 1H), 4.85–4.80 (m, 3H), 4.61 (d, J=11.60 Hz, 1H), 4.53 (d, J=10.70 Hz, 1H), 4.49 (d, J=11.60 Hz, 1H), 4.32 (d, J=7.93 Hz, 1H), 3.87 (t, J=4.88 Hz, 4H), 3.83–3.66 (m, 8H), 3.58 (s, 3H), 3.53–3.47 (m, 2H), 3.15–3.13 (m, 4H), 3.02–2.97 (m, 2H), 2.87–2.83 (m, 2H); $^{13}$C-NMR (CDCl$_3$) δ 151.1, 151.0, 138.7, 138.3, 133.6, 130.1, 129.5, 128.6, 128.5 (2 lines), 128.2, 128.0, 127.9 (2 lines), 127.8, 123.9, 119.3, 115.7, 104.7, 85.0, 82.7, 78.2, 75.8, 75.2, 75.1, 73.4, 70.5, 68.5, 67.6, 67.1, 57.2, 53.3, 49.5; FAB MS m/z (M+Na)$^+$: calcd 747.3621, obsd 747.3605.

EXAMPLE 35
Halobenzyl Ethers as Protecting Groups in Organic Syntheses

The differential protection of functional groups of similar reactivity is a major challenge for the synthesis of complex natural products. The task of distinguishing specific hydroxyl and amino groups becomes particularly daunting in oligosaccharide assembly when highly branched structures necessitate several selectively removable blocking groups. Over the years a host of protecting groups have been introduced, each making use of the unique reactivity of the particular masking moiety.[1] Traditionally, benzyl ethers have been employed for 'permanent' protection and are removed during the late stages of a synthesis. Esters and silyl ethers, on the other hand, are used to 'temporarily' protect hydroxyl groups to be unveiled during the synthesis. Orthogonality of protecting groups is a key issue for the planning and experimental execution of a given synthesis.

In order to increase the scope of available hydroxyl protecting groups, substituted benzyl ethers that can be selectively removed in the presence of unsubstituted benzyl ethers have been developed. These substituted benzyl ethers are generally less stable to different reaction conditions than unsubstituted benzyl ethers.[1] The 4-O-methoxy benzyl group (PMB) has found frequent application in natural product synthesis since it can be cleaved oxidatively in a selective manner.[1] The acid sensitivity of this group, while restricting its synthetic utility, has also been exploited for its removal.[2] More recently, other 4-O-substituted benzyl ethers containing acetate and trialkylsilyl substituents have been reported.[3] Although the removal of these benzyl ethers does not require catalytic hydrogenation, the necessity of treatment with base or fluoride, followed by oxidative cleavage renders them incompatible with ester, silyl, or PMB protecting groups.

A set of protecting groups that are equally or more stable than unsubstituted benzyl ethers and which may be removed selectively under mild conditions without affecting other commonly used protecting groups would be ideal. We anticipated that stable, readily accessible halogenated benzyl ethers[4] fulfill all of the aforementioned requirements and could be converted into labile aryl amines by Pd-catalyzed amination.

The catalytic amination of aryl halides represents a mild alternative to the classical methods of aromatic C—N bond formation.[5] Here we describe the use of Pd-catalyzed aminations to convert stable halogenated benzyl ethers into substituted aryl amines which can be cleaved by brief exposure to Lewis acids, protic acids or oxidants (Scheme 1). Selective removal of substituted benzyl ethers in the presence of silyl ethers, alkyl and aryl esters, PMB ethers, acetals, or a glycal double bond was readily achieved.

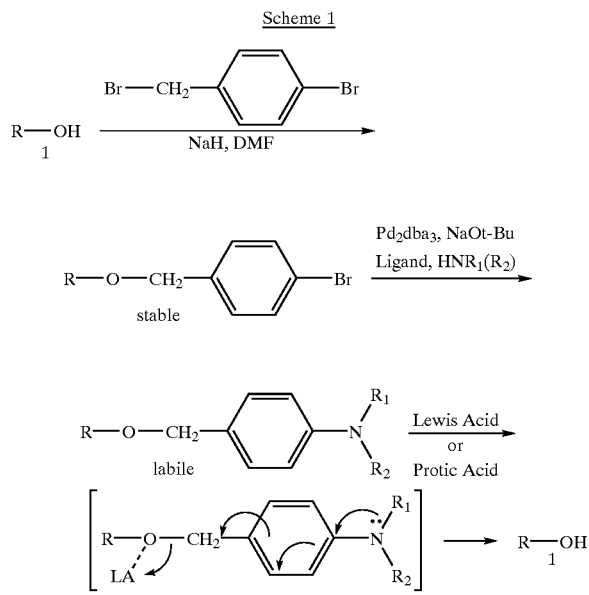

Scheme 1

The introduction of halogenated benzyl ether protecting groups was accomplished in a straightforward manner by nation of PIB (4-iodobenzyl) functionalized galactoside 4 was accomplished in high yield (96%) at room temperature.

TABLE 1

Pd-catalyzed amination of halogenated benzyl ethers[a]

| Halide | Amine | Product | Yield (%) |
|---|---|---|---|
| 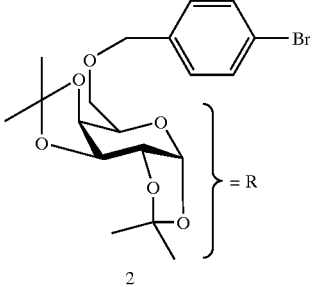 2 | $H_2N$—Bn | 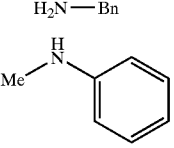 6 | 91 |
| | 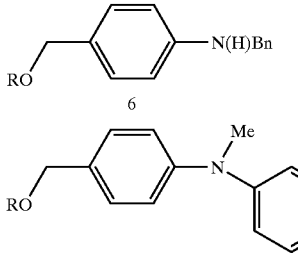 | 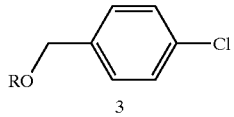 | 96 |
| | 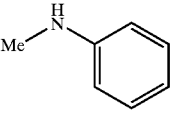 | 7 | 89[b,c] |
| 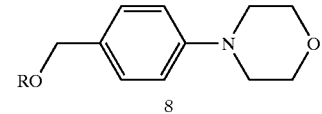 3 | 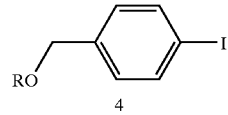 |  8 | 95[b] |
| 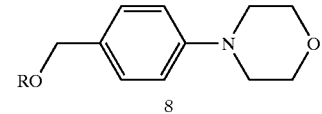 4 | 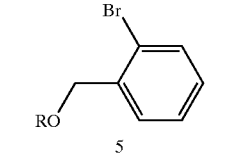 | 7 | 96[c,d] |
| 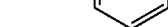 5 | $H_2N$—Bn | 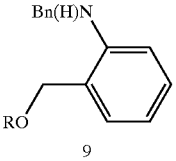 9 | 85 |

[a]Reaction conditions: 1.0 equiv aryl halide, 1.2 equiv amine, 1.4 equiv NaOtBu, cat. $Pd_2dba_3$, (o-biphenyl)P(tBu)$_2$ (2L/Pd), toluene (2 mL/mmol halide), 80° C.
[b]Pd(OAc)$_2$ used in place of $Pd_2dba_3$.
[c]The reaction was conducted at room temperature.
[d]1-(N,N-dimethylamino)-1'-(dicyclohexylphosphino) biphenyl used in place of (o-biphenyl)P(tBu)$_2$ (1L/Pd). 1.05 equiv amine were used.

reaction of the hydroxyl group with the corresponding benzyl chloride or benzyl bromide in the presence of sodium hydride.[1,6] With a series of protected monosaccharides 2–5 in hand, Pd-catalyzed amination reactions employing different amines were explored (Table 1). Following recently developed protocols, the 4-bromobenzyl (PBB) protected galactose 2 was coupled with benzylamine or N-methyl aniline using $Pd_2(dba)_3$ (1 mol % Pd), and (o-biphenyl)P(t-Bu)$_2$ (2 mol %) as the catalyst system in the presence of sodium tert-butoxide.[7,8] The reactions were carried out at 80° C. for 5 h or alternatively at room temperature for 16 h. The 4-chlorobenzyl (PCB) moiety of galactose 3 could be efficiently N-arylated with N-methylaniline or morpholine. 2-Bromobenzyl ethers (OBB) could also be employed as demonstrated by the reaction of 2-bromobenzyl ether 5 with benzylamine to provide 9 in good yield. Additionally, ami- After protocols for the facile conversion of the stable halogenated benzyl ethers into a variety of aryl amines had been established, conditions to facilitate the cleavage of these amines were explored (Table 2). Benzylamine 6 was quantitatively cleaved with strong Lewis acids ($TiCl_4$, $SnCl_4$) in only five minutes. Similarly, treatment of 6 with 1% dichloroacetic acid (DCA) gave deprotected product in a matter of minutes. Reaction with cerium (IV) ammonium nitrate yielded the free alcohol in modest yield after 30 minutes. Tertiary aryl amine 7 was more labile to Lewis acids as it could be quantitatively cleaved by $ZnCl_2$. Aryl morpholino substrate 8 as well as ortho-substituted aryl benzyl amine 9 required $TiCl_4$ for efficient cleavage.

TABLE 2

Cleavage of Aminated Benzyl Ether Protecting Groups[a]

| Amine | Reagent | Time | Yield |
|---|---|---|---|
| 6 | SnCl$_4$ | 5 min | >95 |
| 6 | 1% DCA | 5 min | >95 |
| 6 | CAN | 30 min | 75[b] |
| 7 | 1% DCA | 5 min | >95 |
| 7 | ZnCl$_2$ | 30 min | >95 |
| 8 | TiCl$_4$ | 5 min | >95 |
| 8 | 1% TFA | 5 min | >95 |
| 9 | TiCl$_4$ | 5 min | >95 |

[a]The reactions were carried out in CH$_2$Cl$_2$ at room temperature. Yields are reported based on TLC analysis.
[b]The reaction was carried out in 9:1 CH$_3$CN:H$_2$O.

With effective cleavage protocols in hand we exploited the differences in the rates of reaction between aryl chlorides, bromides and iodides in Pd-catalyzed amination reactions.[7] A demonstration of our orthogonal protecting group strategy based on halogenated benzyl ethers is shown in the construction of a model trisaccharide (Scheme 2). Starting with differentially protected monosaccharide 10,[9] the PIB group was selectively removed while no cleavage of the PBB and PCB groups occurred. Glycosylation employing mannosyl trichloroacetimidate 12 yielded 88% of the desired disaccharide 13.[10] Removal of the PBB group proceeded smoothly in the presence of the C4 PCB group to fashion deprotected 14. Alkylation with propyl iodide followed by cleavage of the PCB moiety gave 16 in 91% yield over 2 steps. Glycosylation with glucosyl phosphate 17 furnished trisaccharide 18 in 85% yield.[11] Differentially protected monosaccharides such as 10 are expected to provide facile entry into the construction of branched oligosaccharides and combinatorial carbohydrate libraries.

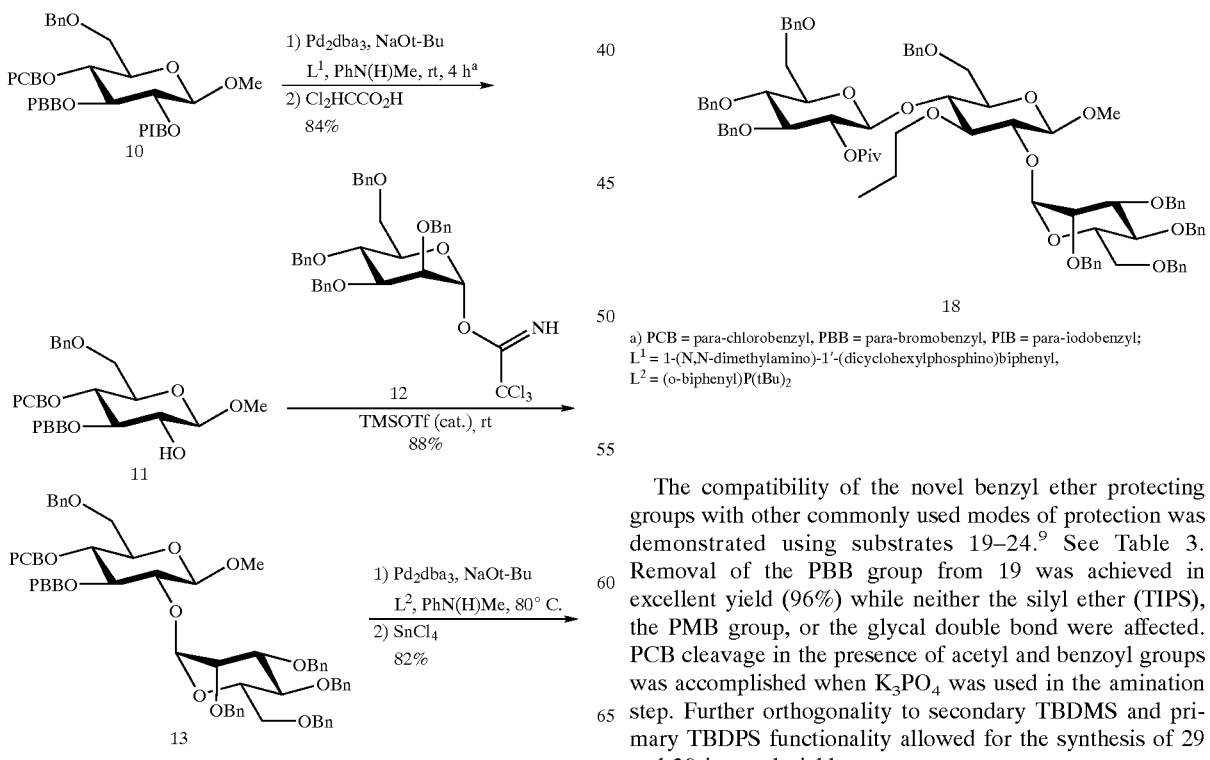

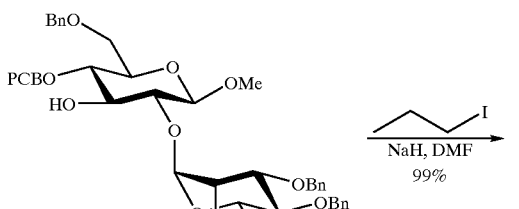

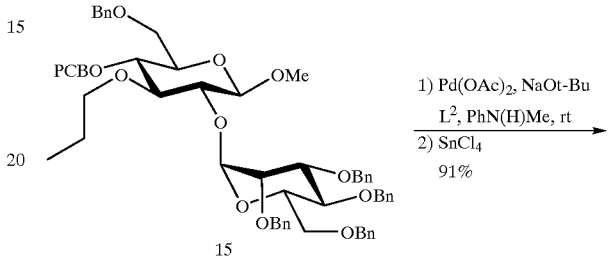

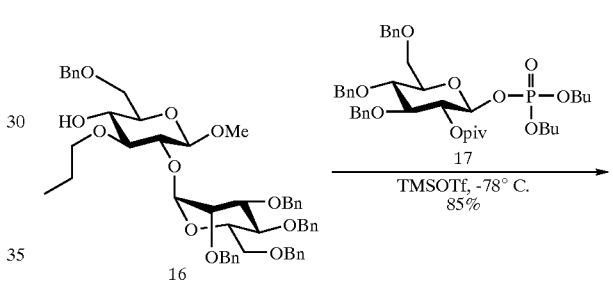

a) PCB = para-chlorobenzyl, PBB = para-bromobenzyl, PIB = para-iodobenzyl; L$^1$ = 1-(N,N-dimethylamino)-1'-(dicyclohexylphosphino)biphenyl, L$^2$ = (o-biphenyl)P(tBu)$_2$ The compatibility of the novel benzyl ether protecting groups with other commonly used modes of protection was demonstrated using substrates 19–24.[9] See Table 3. Removal of the PBB group from 19 was achieved in excellent yield (96%) while neither the silyl ether (TIPS), the PMB group, or the glycal double bond were affected. PCB cleavage in the presence of acetyl and benzoyl groups was accomplished when K$_3$PO$_4$ was used in the amination step. Further orthogonality to secondary TBDMS and primary TBDPS functionality allowed for the synthesis of 29 and 30 in good yield.

TABLE 3

Functional Group Compatability

| Substrate | Product | Method | Yield |
|---|---|---|---|
| 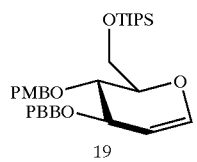 19 | 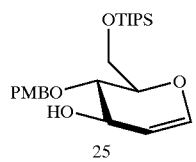 25 | A[a] | 96 |
| 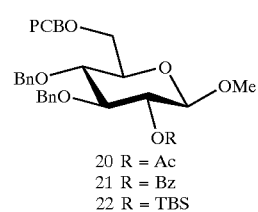 20 R = Ac; 21 R = Bz; 22 R = TBS | 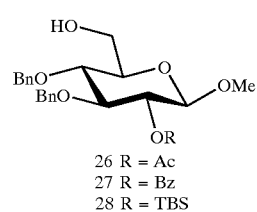 26 R = Ac; 27 R = Bz; 28 R = TBS | B[b]; B[b]; A[a] | 87; 79; 70 |
| 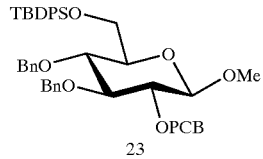 23 | 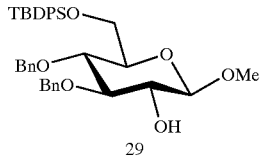 29 | A[b] | 81 |
| 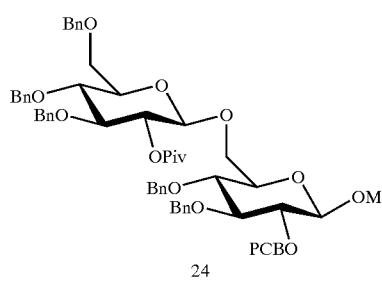 24 | 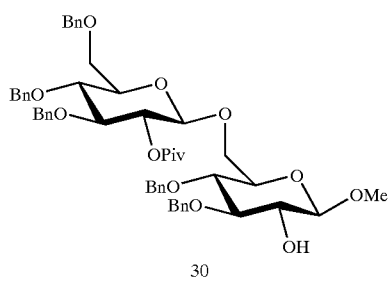 30 | A[a,c] | 89 |

A: 1.0 equiv halide, 1.2 equiv N-methylaniline, 1.4 equiv NaOtBu, cat. $Pd_2dba_3$, (o-biphenyl)P(tBu)$_2$ (2L/Pd), toluene (2 mL/mmol halide). Room temperature, 12 h.
B: 1.0 equiv halide, 1.2 equiv morpholine, 1.4 equiv $K_3PO_4$, cat. Pd(OAc)$_2$, 1-(N,N-dimethylamino)-1'-(dicyclohexylphosphino) biphenyl (1L/Pd), DME (2 mL/mmol halide). 100° C., 12 h.
[a]Cleaved with $ZnCl_2$.
[b]Cleaved with $SnCl_4$.
[c]Pd(OAc)$_2$ used in place of $Pd_2dba_3$.

In conclusion, a new concept for the protection of hydroxyl groups is reported. Halobenzyl ethers of comparable chemical inertness to unsubstituted benzyl ethers were efficiently differentiated in an iterative deprotection scheme by Pd-catalyzed amination followed by treatment with a Lewis or protic acid. The results disclosed here provide the basis for the design of a host of different halobenzyl ether protecting groups containing different substitution patterns. These halobenzyl ethers will be useful for the protection of hydroxyl as well as other functional groups. Furthermore, they should find wide application in the synthesis of natural products, complex carbohydrates, and in the preparation of combinatorial carbohydrate libraries.

Notes & References for Example 35

(1) Greene, T. W.; Wuts, P. G. M. *Protective Groups in Organic Synthesis*; John Wiley & Sons; New York, 1999.
(2) Yan, L.; Kahne, D. E. *Synlett* 1995, 523–524.
(3) Jobron, L.; Hindsgaul, O. *J. Am. Chem. Soc.* 1999,121, 5835–5836.
(4) Initial studies with PBB, PCB in peptide synthesis: Yamashiro, D. *J. Org. Chem.* 1977, 42, 523–525; PCB in oligosaccharide synthesis: Pohl, N. L.; Kiessling, L. L. *Tetrahedron Lett.* 1997, 38, 6985–6988.
(5) (a) Yang, B. H.; Buchwald, S. L. *J Organomet. Chem.* 1999, 576, 125–146; (b) Wolfe, J. P.; Wagaw, S.; Marcoux, J.-F.; Buchwald, S. L. *Acc. Chem. Res.* 1998, 31, 805–818; (c) Hartwig, J. F. *Angew. Chem. Int. Ed.* 1998, 37, 2046–2067.
(6) Cost analysis of substituted benzyl halides: 4-chlorobenzyl chloride ($0.10/g), 4-bromobenzyl bromide ($0.70/g), 4-iodobenzyl bromide ($10/g).
(7) Wolfe, J. P.; Tomori, H.; Yin, J.; Sadighi, J.; Buchwald, S. L. *J. Org. Chem.* 2000, 65, 1158–1174.
(8) The coupling with n-hexylamine resulted in the formation of a significant amount of the bis-arylation product.
(9) Please see subsequent Examples for details of the preparation 10, and 19–24.
(10) Mayer, T. G.; Kratzer, B.; Schmidt, R. R. *Angew. Chem. Int.* Ed. 1994, 33, 2177–2180.
(11) Plante, O. J.; Andrade, R. B.; Seeberger, P. H. *Org. Lett.* 1999, 1, 211–214.

EXAMPLE 36

Figure 8:
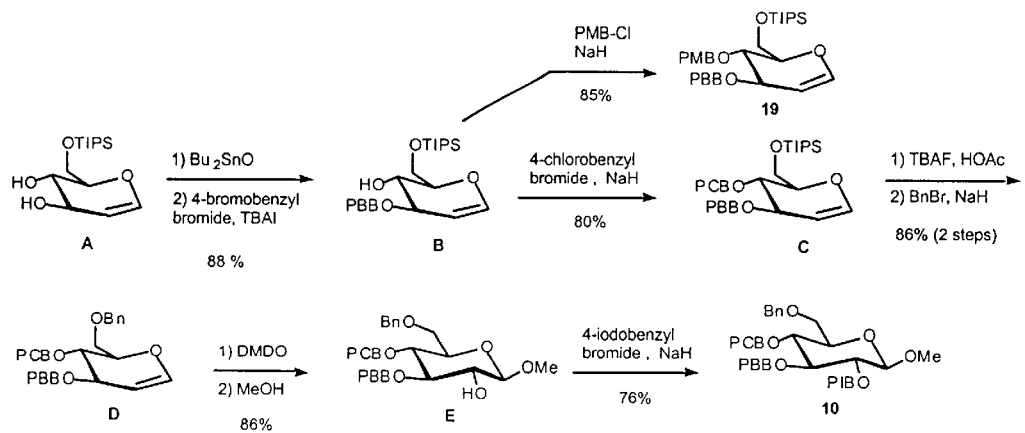
FIG. 8 depicts schematically the synthesis of various compounds disclosed in Example 36.
Figure 8:
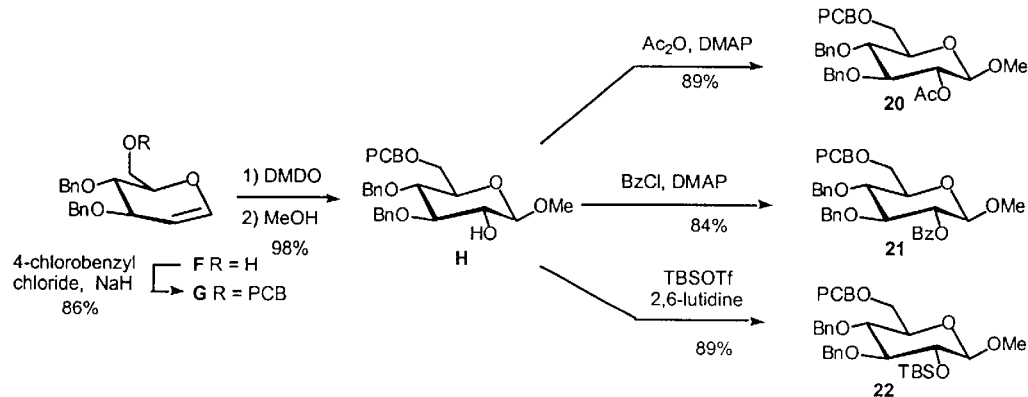
Figure 9:
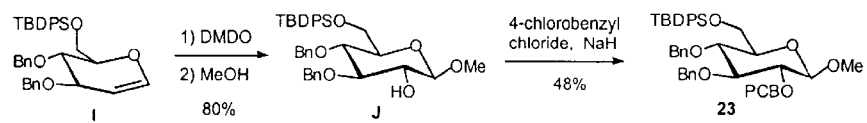
FIG. 9 depicts schematically the synthesis of various compounds disclosed in Example 36.
Figure 9:
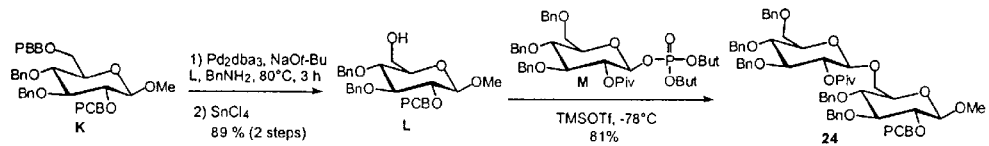

Halobenzyl Ethers as Protecting Groups in Organic Syntheses—General Experimental Procedures and Specific Applications Thereof (See also FIGS. 8 and 9)

General Methods.

All chemicals used were reagent grade and used as supplied except where noted. Dichloromethane ($CH_2Cl_2$) was distilled from calcium hydride under $N_2$. Tetrahydrofuran (THF) was distilled from Na/benzophenone under $N_2$. Toluene was distilled under nitrogen from molten sodium. N,N-Dimethylformamide (DMF), and ethylene glycol dimethyl ether (DME) were obtained from Aldrich Chemical Co. (Sure-Seal Grade) and used without further purification. Benzylamine, morpholine and N-methylaniline were obtained from Aldrich Chemical Co. and passed through basic alumina before use. Palladium acetate, tris (dibenzylideneacetone)dipalladium(0), and (o-biphenyl)P(t-Bu)$_2$ were obtained from Strem Chemical company. 1-(N,N-dimethylamino)-1'-(dicyclohexylphosphino)biphenyl was prepared as described previously. See Old, D. W.; Wolfe, J. P.; Buchwald, S. L. *J. Am. Chem. Soc.* 1998, 120, 9722. Sodium t-butoxide was purchased from Aldrich Chemical Company; the bulk of this material was stored under nitrogen in a Vacuum Atmospheres glovebox. Small portions (1–2 g) were removed from the glovebox in glass vials, stored in the air in desiccators filled with anhydrous sodium sulfate, and weighed in the air. Analytical thin-layer chromatography was performed on E. Merck silica gel 60 $F_{254}$ plates (0.25 mm). Compounds were visualized by dipping the plates in a cerium sulfate-ammonium molybdate solution followed by heating. Liquid column chromatography was performed using forced flow of the indicated solvent on Silicycle 230–400 mesh (60 Å pore diameter) silica gel. $^1$H NMR spectra were obtained on a Varian VXR-500 spectrometer (500 MHz) and are reported in parts per million (δ) relative to $CHCl_3$ (7.27 ppm). Coupling constants (J) are reported in Hertz. $^{13}$C NMR spectra were obtained on a Varian VXR-500 spectrometer (125 MHz) and are reported in δ relative to $CDCl_3$ (77.23 ppm) as an internal reference. Abbreviations: TMSOTf =trimethysilyl triflate, DDQ=2,3-dichloro-5,6-dicyanoquinone, CAN= cerium(IV) ammonium nitrate, DMAP=4-N,N-dimethylaminopyridine, TFA=trifluoroacetic acid, DCA= dichloroacetic acid.

General Procedure A: Benzylation of Alcohols.

A flask containing the alcohol (1.0 equiv) was purged with nitrogen and charged with DMF (10 mL/mmol OH). A nitrogen purge was installed and NaH (1.1 equiv, 60% in mineral oil) and the substituted benzyl bromide (1.1 equiv) were added. The reaction was stirred at room temperature for 30 min then quenched by dropwise addition of water, diluted with EtOAc and washed with water and brine. The organic layer was dried over $Na_2SO_4$, filtered, concentrated in vacuo and purified by flash column chromatography on silica gel.

General Procedure B: Catalytic Amination of Aryl Bromides.

The aryl bromide (1 equiv) was loaded into a round-bottom flask and azeotropically dried with toluene (3×3 mL) followed by additional drying for 1 h under vacuum. The flask was purged with argon, the amine (1.2 equiv) was added and the residue dissolved in toluene (2 mL/mmol halide). An oven-dried resealable Schlenk flask was evacuated and backfilled with argon. The flask was charged with $Pd_2(dba)_3$ (1.0 mol % Pd), (o-biphenyl)P(t-Bu)$_2$ (2 mol %), NaOtBu (1.4 equiv), evacuated and backfilled with argon. A rubber septum was installed and the aryl bromide/amine solution was added via cannula. The flask was sealed using a teflon screwcap and the reaction mixture was heated to 80° C. with vigorous stirring. After 5 h, the reaction solution was cooled to room temperature, diluted with diethyl ether, filtered through a pad of celite and concentrated in vacuo. The crude product was either purified by flash column chromatography on silica gel or treated directly with a Lewis acid.

General Procedure C: Catalytic Amination of Aryl Chlorides.

The aryl chloride (1 equiv) was loaded into a round-bottom flask and azeotropically dried with toluene (3×3 mL) followed by additional drying for 1 h under vacuum. The flask was purged with argon, the amine (1.2 equiv) was added and the residue dissolved in toluene (2 mmol halide). An oven-dried resealable Schlenk flask was evacuated and backfilled with argon. The flask was charged with Pd(OAc)$_2$ (2.0 mol % Pd), (o-biphenyl)P(t-Bu)$_2$ (4.0 mol %), NaOtBu (1.4 equiv), evacuated and backfilled with argon. A rubber septum was installed and the aryl chloride/amine solution was added via cannula. The flask was sealed using a teflon screwcap and the reaction mixture was stirred at room temperature. After 16 h, the reaction solution was diluted with diethyl ether, filtered through a pad of celite and concentrated in vacuo. The crude product was either purified by flash column chromatography on silica gel or treated directly with a Lewis acid.

General Procedure D: Deprotection of Amino Substituted Benzyl Ethers.

A solution of aminobenzyl ether (1 equiv) in $CH_2Cl_2$ was treated with the appropriate Lewis (1 equiv) or protic acid. After stirring at room temperature for 30 min, the reaction mixture was diluted with $CH_2Cl_2$ and washed with $H_2O$, $NaHCO_3$ and brine. The organic fractions were dried over $Na_2SO_4$, filtered through celite and concentrated in vacuo. The crude product was purified by flash column chromatography on silica gel.

Cleavage of Amino Substituted Benzyl Ethers:

A solution of 6 (0.010 mmol) in $CH_2Cl_2$ (0.5 mL) was reacted with 0.010 mmol each: $TiCl_4$, $SnCl_4$, $ZnCl_2$, TMSOTf, and NaOMe. A 9:1 $CH_3CN:H_2O$ solution was used for reaction with DDQ and CAN. Protic acids employed include: 10% TFA/$CH_2Cl_2$, 1% TFA/$CH_2Cl_2$, 10% DCA/$CH_2Cl_2$, 1% DCA/$CH_2Cl_2$, 10% AcOH/$CH_2Cl_2$, 1% AcOH/$CH_2Cl_2$. All reactions were carried out at room temperature for 16 h unless observed to be complete by TLC. Reaction of 6 with either $TiCl_4$, $SnCl_4$, 10% TFA/$CH_2Cl_2$, 1% TFA/$CH_2Cl_2$, 10% DCA/$CH_2Cl_2$ or 1% DCA/$CH_2Cl_2$ resulted in complete conversion within 5 min. Oxidative deprotection with CAN proceeded in 75% yield by TLC in 30 min. Treatment of 6 with either $ZnCl_2$, TMSOTf, NaOMe, DDQ, 10% AcOH/$CH_2Cl_2$ or 1% AcOH/$CH_2Cl_2$ did not afford deprotected product.

Under similar conditions, reaction of 7 with either $TiCl_4$, $SnCl_4$, 10% TFA/$CH_2Cl_2$, 1% TFA/$CH_2Cl_2$, 10% DCA/$CH_2Cl_2$ or 1% DCA/$CH_2Cl_2$, resulted in complete conversion within 5 min while $ZnCl_2$ provided deprotected product in quantitative yield in 30 min. Treatment of 7 with 10% AcOH/$CH_2Cl_2$ or 1% AcOH/$CH_2Cl_2$ did not afford deprotected product.

Reaction of 8 with either $TiCl_4$, $SnCl_4$, 10% TFA/$CH_2Cl_2$ or 1% TFA/$CH_2Cl_2$ provided deprotected product in 95% yield in 5 min. Treatment of 8 with $ZnCl_2$, 10% DCA/$CH_2Cl_2$, 1% DCA/$CH_2Cl_2$, 10% AcOH/$CH_2Cl_2$ or 1% AcOH/$CH_2Cl_2$ did not afford deprotected product.

Reaction of 9 with $TiCl_4$ resulted in complete conversion within 5 min. Treatment of 9 with $SnCl_4$, $ZnCl_2$, 10% TFA/$CH_2Cl_2$, 1% TFA/$CH_2Cl_2$, 10% DCA/$CH_2Cl_2$, 1% DCA/$CH_2Cl_2$, 10% AcOH/$CH_2Cl_2$ or 1% AcOH/$CH_2Cl_2$ did not afford deprotected product.

6-O-(4-Bromobenzyl)-1,2:3,4-di-O-isopropylidene-α-D-galactopyranoside 2.

General procedure A using 1,2:3,4-di-O-isopropylidene-α-D-galactopyranoside (3.12 g, 12.0 mmol), NaH (0.66 g, 13.2 mmol, 60% in mineral oil) and 4-bromobenzylbromide (3.30 g, 13.2 mmol) gave 4.96 g (96%) of 2 as a colorless oil after purification by flash column chromatography on silica gel (20% EtOAc/Hexanes). [°]$^{24}_D$: −49.6° (c 1.62, CH$_2$Cl$_2$); IR (thin film) 2987, 2933, 1478, 1070 cm$^{-1}$; $^1$H-NMR (CDCl$_3$) δ 7.43 (d, J=8.2 Hz, 2H), 7.20 (d, J=8.5 Hz, 2H), 5.53 (d, J=4.9 Hz, 1H), 4.58 (dd, J=2.4, 7.9 Hz, 1H), 4.55 (d, J=12.5 Hz, 1H), 4.47 (d, J=12.2 Hz, 1H), 4.30 (dd, J=2.4, 5.2 Hz, 1H), 4.24 (dd, J=1.8, 7.9 Hz, 1H), 3.98 (dt, J=1.8, 7.0 Hz, 1H), 3.68–3.58 (m, 2H), 1.52 (s, 3H), 1.42 (s, 3H), 1.32 (s, 3H), 1.31 (s, 3H); $^{13}$C-NMR (CDCl$_3$) δ 137.5, 131.5, 129.4, 121.5, 109.3, 108.6, 96.5, 72.6, 71.3, 70.8, 70.6, 69.2, 67.1, 26.2, 26.1, 25.1, 24.6; FAB MS m/z (M+Na)$^+$: calcd 451.0732, obsd 451.0722.

6-O-(4-Chlorobenzyl)-1,2:3,4-di-O-isopropylidene-α-D-galactopyranoside 3.

General procedure A using using 1,2:3,4-di-O-isopropylidene-α-D-galactopyranoside (2.60 g, 10.0 mmol), NaH (0.60 g, 12.0 mmol, 60% in mineral oil), 4-chlorobenzylchloride (1.93 g, 12.0 mmol) and tetrabutylammonium iodide (26 mg, 0.07 mmol) gave 3.65 g (95%) of 3 as a colorless oil after purification by flash column chromatography on silica gel (20% EtOAc/Hexanes). [α]$^{24}_D$: −59.6° (c 1.73, CH$_2$Cl$_2$); IR (thin film) 2987, 2934, 1382, 1070 cm$^{-1}$; $^1$H-NMR (CDCl$_3$) δ 7.31–7.26 (m, 4H), 5.54 (d, J=4.9 Hz, 1H), 4.61–4.56 (m, 2H), 4.50 (d, J=12.2 Hz, 1H), 4.30 (dd, J=2.4, 5.2 Hz, 1H), 4.25 (dd, J=1.8, 7.9 Hz, 1H), 4.00–3.97 (m, 1H), 3.69–3.58 (m, 2H), 1.53 (s, 3H), 1.43 (s, 3H), 1.33 (s, 3H), 1.32 (s, 3H); $^{13}$C-NMR (CDCl$_3$) δ 137.0, 133.3, 129.1, 128.6, 109.3, 108.7, 96.5, 72.6, 71.3, 70.6, 69.1, 67.0, 26.2, 26.1, 25.1, 24.6; FAB MS m/z (M+Na)$^+$: calcd 407.1237, obsd 407.1232.

6-O-(4-Iodobenzyl)-1,2:3,4-di-O-isopropylidene-α-D-galactopyranoside 4.

General procedure A using using 1,2:3,4-di-O-isopropylidene-α-D-galactopyranoside (1.00 g, 3.84 mmol), NaH (0.212 g, 4.23 mmol, 60% in mineral oil) and 4-iodobenzylbromide (1.25 g, 4.23 mmol) gave 1.65 g (90%) of 4 as a colorless oil after purification by flash column chromatography on silica gel (20% EtOAc/Hexanes). [α]$^{24}_D$: −50.3° (c 2.92, CH$_2$Cl$_2$); IR (thin film) 2986, 2932, 1484, 1381, 1070 cm$^{-1}$; $^1$H-NMR (CDCl$_3$) δ 7.66 (d, J=8.2 Hz, 2H), 7.00 (d, J=8.2 Hz, 2H), 5.55 (d, J=4.9 Hz, 1H), 4.60 (dd, J=2.4, 7.9 Hz, 1H), 4.56 (d, J=12.5 Hz, 1H), 4.49 (d, J=12.2 Hz, 1H), 4.31 (dd, J=2.4, 5.2 Hz, 1H), 4.26 (dd, J=1.8, 7.9 Hz, 1H), 4.01–3.97 (m, 1H), 3.68 (dd, J=5.8, 10.1 Hz, 1H), 3.62 (dd, J=7.0, 10.1 Hz, 1H), 1.54 (s, 3H), 1.44 (s, 3H), 1.34 (app s, 6H); $^{13}$C-NMR (CDCl$_3$) δ 137.6, 129.8, 109.4, 108.8, 96.5, 93.2, 72.8, 71.4, 70.8, 70.7, 69.2, 67.1, 26.3, 26.2, 25.1, 24.6; FAB MS m/z (M+Na)$^+$: calcd 499.0594, obsd 499.0584.

6-O-(2-Bromobenzyl)-1,2:3,4-di-O-isopropylidene-α-D-galactopyranoside 5.

General procedure A using using 1,2:3,4-di-O-isopropylidene-α-D-galactopyranoside (3.12 g, 12.0 mmol), NaH (0.66 g, 13.2 mmol, 60% in mineral oil) and 2-bromobenzylbromide (3.30 g, 13.2 mmol) gave 4.96 g (99%) of 5 as a colorless oil after purification by flash column chromatography on silica gel (20% EtOAc/Hexanes). [α]$^{24}_D$: −48.6° (c 1.39, CH$_2$Cl$_2$); IR (thin film) 2987, 2933, 1381, 1070 cm$^{-1}$; $^1$H-NMR (CDCl$_3$) δ 7.51–7.49 (m, 2H), 7.29 (dt, J=1.2, 7.0 Hz, 1H), 7.11 (dt, J=1.8, 7.6 Hz, 1H), 5.55 (d, J=5.2 Hz, 1H), 4.67–4.59 (m, 3H), 4.32–4.29 (m, 2H), 4.06 (dt, J=1.8, 6.4 Hz, 1H), 3.78–3.68 (m, 2H), 1.55 (s, 3H), 1.44 (s, 3H), 1.33 (s, 3H), 1.32 (s, 3H); $^{13}$C-NMR (CDCl$_3$) δ 137.7, 132.5, 129.1, 128.9, 127.4, 122.6, 109.3, 108.7, 96.5, 72.6, 71.3, 70.8, 70.7, 69.5, 66.8, 26.3, 26.1, 25.1, 24.6; FAB MS m/z (M+Na)$^+$: calcd 451.0732, obsd 451.0726.

6-O-(4-(N-Benzylamino)benzyl)-1,2:3,4-di-O-isopropylidene-α-D-galactopyranoside 6.

General procedure B using 2 (0.214 g, 0.50 mmol), benzylamine (66 μL, 0.60 mmol), Pd$_2$(dba)$_3$ (2.4 mg, 0.0026 mmol), (o-biphenyl)P(t-Bu)$_2$ (3.0 mg, 0.010 mmol), NaOtBu (68.0 mg, 0.70 mmol) gave 0.206 g (91%) of 6 as a yellow oil after purification by flash column chromatography on silica gel (30% EtOAc/Hexanes). [α]$^{24}_D$: −47.3° (c 1.35, CH$_2$Cl$_2$); IR (thin film) 3405, 2985, 2933, 1615, 1523 cm$^{-1}$; $^1$H-NMR (CDCl$_3$) δ 7.39–7.34 (m, 4H), 7.30–7.26 (m, 1H), 7.17 (d, J=8.5 Hz, 2H), 6.61 (d, J=8.5 Hz, 2H), 5.56 (d, J=4.9 Hz, 1H), 4.60 (dd, J=2.4, 7.9 Hz, 1H), 4.50 (d, J=11.3 Hz, 1H), 4.44 (d, J=11.6 Hz, 1H), 4.34 (s, 2H), 4.31 (dd, J=2.4, 5.2 Hz, 1H), 4.28 (dd, J=2.1, 7.9 Hz, 1H), 4.10 (br s, 1H), 3.99 (dt, J=1.8, 6.4 Hz, 1H), 3.68–3.59 (m, 2H), 1.54 (s, 3H), 1.46 (s, 3H), 1.35 (s, 3H), 1.34 (s, 3H); $^{13}$C-NMR (CDCl$_3$) δ 147.9, 139.5, 129.7, 128.8, 127.6, 127.4, 127.2, 112.8, 109.3, 108.6, 96.5, 73.5, 71.3, 70.8, 68.4, 67.0, 48.4, 26.3, 26.2, 25.1, 24.6; FAB MS m/z (M)$^+$: calcd 455.2308, obsd 455.2303.

6-O-(4-(N-Methyl-N-phenylamino)benzyl)-1,2:3,4-di-O-isopropylidene-α-D-galactopyranoside 7.

General procedure B using 2 (0.214 g, 0.50 mmol), N-methylaniline (65 μL, 0.60 mmol), Pd$_2$(dba)$_3$ (2.4 mg, 0.0026 mmol), (o-biphenyl)P(t-BU)$_2$ (3.0 mg, 0.010 mmol), NaOtBu (68.0 mg, 0.70 mmol) gave 0.219 g (96%) of 7 as a yellow oil after purification by flash column chromatography on silica gel (20% EtOAc/Hexanes). [α]$^{24}_D$: −52.4° (c 2.04, CH$_2$Cl$_2$); IR (thin film) 2985, 2933, 1594, 1497, 1069 cm$^{-1}$; $^1$H-NMR (CDCl$_3$) δ 7.30–7.26 (m, 4H), 7.04–6.95 (m, 5H), 5.57 (d, J=5.2 Hz, 1H), 4.62 (dd, J=2.4, 7.9 Hz, 1H), 4.58 (d, J=11.6 Hz, 1H), 4.52 (d, J=11.9 Hz, 1H), 4.34–4.30 (m, 2H), 4.04–4.01 (m, 1H), 3.73–3.63 (m, 2H), 3.32 (s, 3H), 1.56 (s, 3H), 1.48 (s, 3H), 1.37 (s, 3H), 1.35 (s, 3H); $^{13}$C-NMR (CDCl$_3$) δ 149.1, 148.7, 131.1, 129.3, 129.2, 121.4, 120.5, 120.4, 109.3, 108.7, 96.5, 73.2, 71.3, 70.8, 68.7, 67.0, 40.4, 26.3, 26.2, 25.1, 24.6; FAB MS m/z (M)$^+$: calcd 455.2308, obsd 455.2299.

6-O-(4-(N-Morpholino)benzyl)-1,2:3,4-di-O-isopropylidene-α-D-galactopyranoside 8.

General procedure C using 3 (0.192 g, 0.50 mmol), morpholine (52 μL, 0.60 mmol), Pd(OAc)$_2$ (2.2 mg, 0.001 mmol), (o-biphenyl)P(t-Bu)$_2$ (6.0 mg, 0.020 mmol), NaOtBu (68.0 mg, 0.70 mmol) gave 0.206 g (95%) of 8 as a yellow oil after purification by flash column chromatography on silica gel (30% EtOAc/Hexanes). [α]$^{24}_D$: −44.5° (c 1.31, CH$_2$Cl$_2$); IR (thin film) 2984, 1724, 1681, 1517, 1069 cm$^{-1}$; $^1$H-NMR (CDCl$_3$) δ 7.26 (d, J=8.6 Hz, 2H), 6.87 (d, J=8.6 Hz, 2H), 5.44 (d, J=5.2 Hz, 1H), 4.58 (dd, J=2.1, 7.9 Hz, 1H), 4.53 (d, J=11.6 Hz, 1H), 4.47 (d, J=11.6 Hz, 1H), 4.30 (dd, J=1.8, 4.9 Hz, 1H), 4.26 (dd, J=1.5, 7.9 Hz, 1H), 3.99–3.95 (m, 1H), 3.85 (t, J=4.9 Hz, 4H), 3.67–3.57 (m, 2H), 3.14 (t, J=4.9 Hz, 4H), 1.52 (s, 3H), 1.44 (s, 3H), 1.33 (s, 3H), 1.32 (s, 3H); $^{13}$C-NMR (CDCl$_3$) δ 151.0, 129.8, 129.3, 115.7, 109.3, 108.6, 96.5, 73.1, 71.3, 70.7, 68.6, 67.0, 49.5, 26.2, 26.1, 25.1, 24.6; FAB MS m/z (M)$^+$: calcd 435.2257, obsd 435.2247.

6-O-(2-(N-Benzylamino)benzyl)-1,2:3,4-di-O-isopropylidene-α-D-galactopyranoside 9.

General procedure B using 5 (0.214 g, 0.50 mmol), benzylamine (66 μL, 0.60 mmol), Pd$_2$(dba)$_3$ (4.6 mg, 0.005 mmol), (o-biphenyl)P(t-Bu)$_2$ (6.0 mg, 0.020 mmol), and NaOtBu (68.0 mg, 0.70 mmol) for 36 h gave 0.193 g (85%) of 9 as a yellow oil after purification by flash column chromatography on silica gel (20% EtOAc/Hexanes). [α]$^{24}_D$: −45.0° (c 0.18, CH$_2$Cl$_2$); IR (thin film) 3397, 2987, 2931, 1608, 1518 cm$^{-1}$; $^1$H-NMR (CDCl$_3$) δ 7.39 (d, J=7.6 Hz, 2H), 7.33 (t, J=7.3 Hz, 2H), 7.27–7.24 (m, 1H), 7.15 (dt, J=1.5, 7.9 Hz, 1H), 7.11 (dd, J=1.5, 7.3 Hz, 1H), 6.66 (dt, J=0.9, 7.3 Hz, 1H), 6.58 (d, J=7.9 Hz, 1H), 5.53–5.48 (m, 2H), 4.66 (d, J=11.0 Hz, 1H), 4.62 (d, J=11.0 Hz, 1H), 4.59 (dd, J=2.4, 7.9 Hz, 1H), 4.45 (d, J=4.9 Hz, 2H), 4.32 (dd, J=2.4, 5.2 Hz, 1H), 4.22 (dd, J=1.8, 7.9 Hz, 1H), 4.03–3.99 (m, 1H), 3.73–3.65 (m, 2H), 1.47 (s, 3H), 1.46 (s, 3H), 1.32 (s, 3H), 1.29 (s, 3H); $^{13}$C-NMR (CDCl$_3$) δ 147.8, 140.0, 130.1, 129.8, 128.6, 127.1, 126.9, 121.7, 116.4, 111.0, 109.5, 108.7, 96.5, 73.2, 71.3, 70.8, 70.6, 68.5, 66.8, 47.5, 26.2, 25.1, 24.7; FAB MS m/z (M)$^+$: calcd 455.2308, obsd 455.2294.

Methyl 6-O-benzyl-3-O-(4-bromobenzyl)-4-O-(4-chlorobenzyl)-2-O-(4-iodobenzyl)-β-D-glucopyranoside 10.

[α]$^{24}_D$: +9.8° (c 3.27, CH$_2$Cl$_2$); IR (thin film) 2865, 1488, 1452, 1074 cm$^{-1}$; $^1$H-NMR (CDCl$_3$) δ 7.62 (d, J=8.2 Hz, 2H), 7.41 (d, J=8.5 Hz, 2H), 7.35–7.27 (m, 5H), 7.23 (d, J=8.2 Hz, 2H), 7.09–7.00 (m, 6H), 4.84 (d, J=11.6 Hz, 1H), 4.79 (d, J=11.6 Hz, 1H), 4.70–4.64 (m, 3H), 4.60 (d, J=11.6 Hz, 1H), 4.54 (d, J=12.2 Hz, 1H), 4.46 (d, J=11.0 Hz, 1H), 4.28 (d, J=7.6 Hz, 1H), 3.76–3.67 (m, 2H), 3.60–3.54 (m, 5H), 3.44–3.41 (m, 1H), 3.40–3.37 (m, 1H); $^{13}$C-NMR (CDCl$_3$) δ 138.2, 138.1, 137.7, 137.6, 136.7, 133.7, 131.7, 131.6, 130.1, 129.5, 129.3, 129.2, 128.7, 128.6, 128.3, 128.1, 127.9, 121.7, 104.8, 84.6, 82.2, 77.9, 74.9, 74.8, 74.2, 74.0, 73.7, 68.8, 57.3; FAB MS m/z (M+Na)$^+$: calcd 815.0248, obsd 815.0275.

Methyl 6-O-benzyl-3-O-(4-bromobenzyl)-4-O-(4-chlorobenzyl)-β-D-glucopyranoside 11.

Glycoside 10 (0.138 g, 0.174 mmol) was loaded into a round-bottom flask and azeotropically dried with toluene (3×3 mL) followed by additional drying for 1 h under vacuum. The flask was purged with argon, N-methylaniline (20 μL, 0.182 mmol) was added and the residue dissolved in THF (0.60 mL). An oven-dried resealable Schlenk flask was evacuated and backfilled with argon. The flask was charged with Pd$_2$dba$_3$ (1.0 mol % Pd, 0.7 mg, 0.0008 mmol), 1-(N,N-dimethylamino)-1'-(dicyclohexylphosphino)biphenyl (1.0 mol %, 0.7 mg, 0.0017 mmol), NaOtBu (23.4 mg, 0.244 mmol), evacuated and backfilled with argon. A rubber septum was installed and glycoside/amine solution was added via cannula. The flask was sealed using a teflon screwcap and the reaction mixture was stirred at room temperature. After 4 h, the reaction solution was diluted with diethyl ether, filtered through a pad of celite and concentrated in vacuo. The aminated product was taken up in CH$_2$Cl$_2$ (1 mL) and treated with 2% dichloroacetic acid/CH$_2$Cl$_2$ (v/v) (1 mL). After stirring at room temperature for 30 min, the reaction mixture was diluted with CH$_2$Cl$_2$, washed with brine, saturated NaHCO$_{3(aq)}$, dried over Na$_2$SO$_4$, filtered and concentrated in vacuo. Purification by flash column chromatography on silica gel (20% EtOAc/Hexanes) gave 84.0 mg 11 (84%) as a white solid. [α]$^{24}_D$: −29.2° (c 2.19, CH$_2$Cl$_2$); IR (thin film) 3450, 2866, 1490, 1452, 1061 cm$^{-1}$; $^1$H-NMR (CDCl$_3$) δ 7.43 (d, J=8.2 Hz, 2H), 7.34–7.23 (m, 7H), 7.20 (d, J=8.2 Hz, 2H), 7.02 (d, J=8.5 Hz, 2H), 4.89 (d, J=11.6 Hz, 1H), 4.72 (d, J=11.6 Hz, 1H), 4.71 (d, J=11.0 Hz, 1H), 4.65 (d, J=12.2 Hz, 1H), 4.53 (d, J=12.2 Hz, 1H), 4.46 (d, J=11.0 Hz, 1H), 4.17 (d, J=7.6 Hz, 1H), 3.75–3.67 (m, 2H), 3.61–3.53 (m, 6H), 3.48–3.44 (m, 1H), 2.41 (d, J=1.5 Hz, 1H); $^{13}$C-NMR (CDCl$_3$) δ 138.1, 137.7, 136.7, 133.7, 131.7, 129.6, 129.2, 128.7, 128.6, 128.1, 127.9, 121.7, 103.9, 84.5, 77.5, 75.2, 75.0, 74.4, 74.3, 73.7, 68.7, 57.4; FAB MS m/z (M+Na)$^+$: calcd 599.0812, obsd 599.0795.

Methyl [2,3,4,6-tetra-O-benzyl-α-D-mannopyranoside-(1→2)]-6-O-benzyl-3-O-(4-bromobenzyl)-4-O-(4-chlorobenzyl)-β-D-glucopyranoside 13.

2,3,4,6-Tetra-O-benzyl-α-D-mannopyranosyl trichloroacetimidate 12 (0.754 g, 1.10 mmol; see Frick, W.; Bauer, A.; Bauer, J.; Wied, S.; Muller, G. *Biochemistry* 1998, 37, 13421) and glycosyl acceptor 11 (0.578 g, 1.00 mmol) were combined and azeotropically dried with toluene (3×10 mL) followed by additional drying for 1 h under vacuum. The mixture was dissolved in CH$_2$Cl$_2$ and a 0.50 M TMSOTf/CH$_2$Cl$_2$ solution (0.10 mL, 0.05 mmol) was added. After stirring for 30 min at room temperature the reaction mixture was diluted with CH$_2$Cl$_2$, washed with satured aqueous NaHCO$_3$, dried over Na$_2$SO$_4$, filtered and concentrated. Purification by flash column chromatography on silica gel (25% EtOAc/Hexanes) gave 0.92 g (88%) of 13 as a yellow oil. [α]$^{24}_D$: +14.9° (c 1.50, CH$_2$Cl$_2$); IR (thin film) 3029, 2864, 1494, 1453, 1361 cm$^{-1}$; $^1$H-NMR (CDCl$_3$) δ 7.46 (d, J=7.0 Hz, 2H), 7.40–7.24 (m, 23H), 7.17–7.09 (m, 6H), 7.02 (d, J=8.2 Hz, 2H), 5.54 (d, J=0.9 Hz, 1H), 4.92 (d, J=10.7 Hz, 1H), 4.84 (d, J=12.8 Hz, 1H), 4.78 (d, J=12.8 Hz, 1H), 4.70–4.47 (m, 10H), 4.41 (d, J=12.2 Hz, 1H), 4.19 (d, J=7.9 Hz, 1H), 4.13 (dd, J=9.5, 9.8 Hz, 1H), 3.93–3.86 (m, 3H), 3.77–3.67 (m, 3H), 3.63–3.57 (m, 2H), 3.51–3.43 (m, 6H); $^{13}$C-NMR (CDCl$_3$) δ 138.9, 138.6, 138.5, 138.0, 136.9, 136.5, 131.4, 129.7, 129.0, 128.7, 128.6, 128.5, 128.4, 128.3, 128.1, 128.0, 127.9, 127.8, 127.6, 127.5, 121.5, 104.6, 97.4, 83.7, 79.6, 78.3, 76.5, 75.2, 75.1, 75.0, 74.8, 74.2, 73.9, 73.7, 73.3, 72.1, 72.0, 71.9, 68.8, 68.6, 56.9; FAB MS m/z (M+Na)$^+$: calcd 1121.3218, obsd 1121.3189.

Methyl [2,3,4,6-tetra-O-benzyl-α-D-mannopyranoside-(1→2)]-6-O-benzyl-4-O-(4-chlorobenzyl)-β-D-glucopyranoside 14.

General procedure B using 13 (0.263 g, 0.25 mmol), N-methylaniline (33 μL, 0.30 mmol), Pd$_2$(dba)$_3$ (2.4 mg, 0.0024 mmol), (o-biphenyl)P(t-Bu)$_2$ (2.8 mg, 0.010 mmol) and NaOtBu (34.0 mg, 0.70 mmol) at 80° C. for 16 h gave a yellow oil. Cleavage with 1.0 M SnCl$_4$ in heptane (0.25 mL, 0.25 mmol) using general procedure D gave 0.181 g (81%) of 14 as a white solid after purification by flash column chromatography on silica gel (30% EtOAc/Hexanes). [α]$^{24}_D$: +26.6° (c 1.66, CH$_2$Cl$_2$); IR (thin film) 3386, 2916, 1494, 1453, 1089 cm$^{-1}$; $^1$H-NMR (CDCl$_3$) δ 7.40–7.26 (m, 23H), 7.23–7.18 (m, 4H), 7.09 (d, J=8.2 Hz, 2H), 5.13 (d, J=1.8 Hz, 1H), 4.86 (d, J=11.0 Hz, 1H), 4.78–4.69 (m, 3H), 4.64–4.47 (m, 7H), 4.39 (d, J=11.3 Hz, 1H), 4.11 (d, J=7.9 Hz, 1H), 4.10–4.06 (m, 1H), 3.86–3.60 (m, 8H), 3.43 (s, 3H), 3.41–3.32 (m, 4H); $^{13}$C-NMR (CDCl$_3$) δ 138.6, 138.4, 138.3, 138.2, 137.1, 133.5, 129.5, 128.6, 128.5, 128.2, 128.1, 128.0, 127.9, 127.8, 127.7, 103.4, 99.7, 82.8, 79.7, 78.0, 76.8, 75.4, 75.0, 74.8, 74.7, 74.0, 73.7, 72.6, 72.4, 69.8, 69.1, 57.3; FAB MS m/z (M+Na)$^+$: calcd 953.3644, obsd 953.3666.

Methyl [2,3,4,6-tetra-O-benzyl-α-D-mannopyranoside-(1→2)]-3-O-propyl-6-O-benzyl-4-O-(4-chlorobenzyl)-β-D-glucopyranoside 15.

Glycoside 14 (0.140 g, 0.158 mmol) and 1-iodopropane (17 μL, 0.174 mmol) were combined and dissolved in DMF (2 mL). NaH (9.0 mg, 0.174 mmol, 60% in mineral oil) was added and the reaction mixture was stirred for 3 h. After quenching with H$_2$O, the solution was diluted with diethyl ether, washed with H$_2$O, dried over Na$_2$SO$_4$, filtered and concentrated. Purification by flash column chromatography on silica gel (25% EtOAc/hexanes) gave 0.144 g 15 (99%) as a colorless oil. [α]$^{24}_D$: +30.8° (c 1.69, CH$_2$Cl$_2$); IR (thin film) 3028, 2864, 1495, 1453, 1090 cm$^{-1}$; $^1$H-NMR (CDCl$_3$) δ 7.42 (d, J=6.4 Hz, 2H), 7.38 (d, J=7.3 Hz, 2H), 7.34–7.20 (m, 23H), 7.09 (d, J=8.5 Hz, 2H), 5.47 (d, J=1.5 Hz, 1H), 4.94 (d, J=11.3 Hz, 1H), 4.79 (d, J=11.3 Hz, 1H), 4.76–4.72 (m, 3H), 4.64–4.51 (m, 6H), 4.44 (d, J=11.0 Hz, 1H), 4.14–4.04 (m, 3H), 3.88–84 (m, 2H), 3.80–3.79 (m, 1H), 3.76–3.73 (m, 1H), 3.70–3.53 (m, 5H), 3.49–3.42 (m, 4H), 3.38–3.35 (m, 1H), 3.22 (t, J=9.2 Hz, 1H), 1.58–1.54 (m, 2H), 0.77 (t, J=7.3 Hz, 3H); $^{13}$C-NMR (CDCl$_3$) δ 139.4, 138.9, 138.7, 138.2, 136.8, 133.7, 132.1, 129.3, 128.7, 128.6, 128.5, 128.4, 128.3, 128.0, 127.9, 127.7, 127.6, 127.5, 127.3, 104.7, 97.2, 83.8, 79.9, 78.3, 76.3, 75.9, 75.1, 74.9, 74.2, 73.7, 73.5, 72.2, 72.1, 69.4, 68.9, 56.9, 23.6, 10.6; FAB MS m/z (M+Na)$^+$: calcd 995.4113, obsd 995.4095.

Methyl [2,3,4,6-tetra-O-benzyl-α-D-mannopyranoside-(1–2)]-3-O-propyl-6-O-benzyl-β-D-glucopyranoside 16.

General procedure C using 15 (0.062 g, 0.067 mmol), N-methylaniline (8.7 μL, 0.081 mmol), Pd(OAc)$_2$ (0.7 mg, 0.0033 mmol, (o-biphenyl)P(t-Bu)$_2$ (2.0 mg, 0.0066 mmol) and NaOtBu (9.0 mg, 0.090 mmol) for 36 h gave a yellow oil. Cleavage with 1.0 M SnCl$_4$ in heptane (67 μL, 0.067 mmol) using general procedure D gave 52 mg (91%) of 16 as a colorless oil after purification by flash column chromatography on silica gel (30% EtOAc/Hexanes). [α]$^{24}_D$: +10.9° (c 2.00, CH$_2$Cl$_2$); IR (thin film) 3458, 3029, 2869, 1496, 1091 cm$^{-1}$; $^1$H-NMR (CDCl$_3$) δ 7.41 (d, J=7.9 Hz, 2H), 7.37–7.24 (m, 21H), 7.19 (d, J=7.9 Hz, 2H), 5.44 (s, 1H), 4.93 (d, J=11.3 Hz, 1H), 4.79–4.71 (m, 3H), 4.63–4.56 (m, 5H), 4.51 (d, J=11.9 Hz, 1H), 4.15–4.09 (m, 2H), 4.04–4.01 (m, 1H), 3.88–3.63 (m, 7H), 3.58–3.52 (m, 3H), 3.44–3.40 (m, 4H), 3.13 (dd, J=0.9, 9.5 Hz, 1H), 2.67 (s, 1H), 1.60–1.52 (m, 2H), 0.80 (dt, J=1.2, 7.3 Hz, 3H); $^{13}$C-NMR (CDCl$_3$) δ 139.3, 138.8, 138.7, 138.6, 138.0, 128.7, 128.5, 128.4, 128.3, 128.0, 127.9, 127.8, 127.7, 127.6, 127.5, 127.4, 104.7, 97.4, 83.5, 79.9, 76.2, 75.5, 74.9, 74.8, 74.2, 74.1, 73.9, 73.5, 72.4, 72.2, 72.1, 70.6, 69.3, 56.9, 23.5, 10.5; FAB MS m/z (M+Na)$^+$: calcd 871.4033, obsd 871.4016.

Dibutyl 2-O-pivaloyl-3,4,6-tri-O-benzyl-β-D-glucopyranoside phosphate 17. (See Plante, O. J.; Andrade, R. B.; Seeberger, P. H. *Org. Lett.* 1999, 1, 211)

3,4,6-Tri-O-benzylglucal (1.12 g, 2.70 mmol) was dissolved in CH$_2$Cl$_2$ (5 mL) and cooled to 0° C. A 0.08 M solution of dimethyldioxirane in acetone (51 mL, 4.06 mmol) was added and the reaction was stirred for 15 min. After the solvent was removed in a stream of N$_2$ and the remaining residue dried in vacuo for 15 min at 0° C., 20 mL CH$_2$Cl$_2$ were added. The solution was cooled to −78° C. for 15 min. Dibutylphosphate (0.563 mL, 1.06 mmol) was added dropwise over 5 min. After complete addition, the reaction was warmed to 0° C. and DMAP (1.32 g, 10.8 mmol) and pivaloyl chloride (0.665 mL, 5.40 mmol) were added. The solution was warmed to room temperature over 1 h. The solvent was removed in vacuo and the residue was purified by flash column chromatography on silica gel to afford 1.74 g (89%) of 17 as a colorless oil. [α]$^{24}_D$: −1.9° (c 1.50, CH$_2$Cl$_2$); IR (thin film) 2946, 1740, 1454, 1282, 1016 cm$^{-1}$; $^1$H-NMR (CDCl$_3$) δ 7.33–7.25 (m, 13H), 7.16–7.14 (m, 2H), 5.24 (dd, J=7.3, 7.3 Hz, 1H), 5.17 (dd, J=8.5, 8.5 Hz, 1H), 4.80–4.75 (m, 2H), 4.70 (d, J=11.0 Hz, 1H), 4.69–4.54 (m, 2H), 4.51 (d, J=11.0 Hz, 1H), 4.08–4.00 (m, 4H), 3.82 (dd, J=9.5, 9.5 Hz, 1H), 3.78–3.70 (m, 3H), 3.64–3.61 (m, 1H), 1.64–1.59 (m, 4H), 1.40–1.34 (m, 4H), 1.20 (s, 9H), 0.96–0.88 (m, 6H); $^{13}$C-NMR (CDCl$_3$) δ 177.2, 138.2, 138.1, 128.7, 128.3, 128.2, 128.1, 128.0, 127.6, 97.0, 96.5, 83.1, 76.2, 75.9, 73.9, 73.3, 68.4, 68.2, 68.1, 39.2, 32.7, 26.9, 19.1, 14.0; $^{31}$P-NMR (CDCl$_3$) δ −2.2; FAB MS m/z (M$^+$) calcd 726.3532, obsd 726.3537.

Methyl 2-O-pivaloyl-3,4,6-tri-O-benzyl-β-D-glucopyranoside-(1→4) [2,3,4,6-tetra-O-benzyl-α-D-mannopyranoside-(1→2)]-3-O-propyl-6-O-benzyl-β-D-glucopyranoside 18.

Glycosyl donor 17 (13.2 mg, 0.0183 mmol) and glycosyl acceptor 16 (13.0 mg, 0.0153 mmol) were combined and azeotropically dried with toluene (3×3 mL) followed by additional drying for 1 h under vacuum. The mixture was dissolved in CH$_2$Cl$_2$ (1 mL) and cooled to −78° C. for 15 min. TMSOTf (3.4 μL, 0.0183 mmol) was added dropwise. After stirring for 10 min at −78° C., the solution was warmed to room temperature and concentrated in vacuo. Purification by flash column chromatography on silica gel (25% EtOAc/Hexanes) gave 17.7 mg (85%) of 18 as a colorless oil. [α]$^{24}_D$: +19.6° (c 1.68, CH$_2$Cl$_2$); IR (thin film) 3029, 2870, 1740, 1453, 1363 cm$^{-1}$; $^1$H-NMR (CDCl$_3$) δ 7.42–7.40 (m, 2H), 7.36–7.16 (m, 38H), 5.44 (d, J=1.5 Hz, 1H), 4.97–4.91 (m, 2H), 4.78–4.69 (m, 6H), 4.62–4.54 (m, 6H), 4.51 (d, J=11.9 Hz, 1H), 4.45 (d, J=11.9 Hz, 1H), 4.42–4.39 (m, 2H), 4.17–4.07 (m, 3H), 3.93–3.86 (m, 2H), 3.81–3.64 (m, 9H), 3.55 (dd, J=7.9, 9.2 Hz, 1H), 3.48–3.40 (m, 5H), 3.35–3.32 (m, 1H), 3.23–3.15 (m, 2H), 1.60–1.49 (m, 2H), 1.14 (s, 9H), 0.67 (t, J=7.3 Hz, 3H); $^{13}$C-NMR (CDCl$_3$) δ 176.8, 139.5, 138.9, 138.8, 138.7, 138.4, 138.3, 138.1, 128.8, 128.7, 128.6, 128.5, 128.4, 128.3, 128.2, 128.1, 128.0, 127.9, 127.8, 127.7, 127.4, 127.3, 127.2, 104.8, 99.5, 97.0, 83.3, 81.6, 80.0, 78.3, 75.9, 75.8, 75.4, 75.3, 75.2, 75.1, 75.0, 74.9, 74.8, 74.4, 73.9, 73.6, 73.4, 72.2, 72.1, 71.9, 69.1, 68.8, 68.2, 56.9, 39.0, 27.5, 23.3, 10.5; FAB MS m/z (M+Na)$^+$: calcd 1387.6545, obsd 1387.6583.

3-O-(4-Bromobenzyl)-4-O-(4-methoxybenzyl)-6-O-triisopropylsilyl-D-arabino-hex-1-enitol 19.

General procedure A using 3-O-(4-bromobenzyl)-6-O-triisopropylsilyl-D-arabino-hex-1-enitol (0.48 g, 1.02 mmol), NaH (61 mg, 1.22 mmol, 60% in mineral oil) and 4-methoxybenzyl chloride (0.17 mL, 1.22 mmol) gave 0.43 g (72%) of 19 as a colorless oil after purification by flash column chromatography on silica gel (10% EtOAc/Hexanes). [α]$^{24}_D$: −13.5° (c 1.80, CH$_2$Cl$_2$); IR (thin film) 2941, 2846, 1647, 1513, 1247 cm$^{-1}$; $^1$H-NMR (CDCl$_3$) δ 7.45 (d, J=8.2 Hz, 2H), 7.25 (d, J=8.2 Hz, 2H), 7.21 (d, J=8.2 Hz, 2H), 6.86 (d, J=8.5 Hz, 2H), 6.40 (dd, J=1.2, 6.1 Hz, 1H), 4.81 (dd, J=2.8, 6.1 Hz, 1H), 4.76 (d, J=11.0 Hz, 1H), 4.71 (d, J=11.0 Hz, 1H), 4.58 (d, J=11.9 Hz, 1H), 4.53–4.48 (m, 2H), 4.17–4.15 (m, 1H), 4.02–3.98 (m, 1H), 3.92–3.90 (m, 2H), 3.81 (s, 3H), 1.13–1.06 (m, 21H); $^{13}$C-NMR (CDCl$_3$) δ 159.5, 145.1, 137.8, 131.7 (2 lines), 130.7, 129.8, 129.6 (2 lines), 129.5, 121.6, 114.0, 99.6, 78.3, 76.0, 73.8, 73.7, 72.1, 71.2, 70.0, 62.1, 55.5, 18.2 (2 lines), 12.2; FAB MS m/z (M+Na)$^+$: calcd 613.1961, obsd 613.1946.

Methyl 2-O-acetyl-3,4-di-O-benzyl-6-O-(4-chlorobenzyl)-β-D-glucopyranoside 20.

Methyl 3,4-di-benzyl-6-O-(4-chlorobenzyl)-β-D-glucopyranoside (0.233 g, 0.467 mmol) was dissolved in 5 mL CH$_2$Cl$_2$. Acetic anhydride (53 μL, 0.560 mmol) and DMAP (0.114 g, 0.934 mmol) were added and the reaction mixture was stirred at room temperature for 1 h. The solution was filtered through silica, eluted with EtOAc and concentrated. Purification by flash column chromatography on silica gel (30% EtOAc/Hexanes) gave 224 mg (89%) of 20 as a colorless oil. [α]$^{24}_D$: −0.5° (c 0.79, CH$_2$Cl$_2$); IR (thin film) 2867, 1747, 1233, 1087, 1060 cm$^{-1}$; $^1$H-NMR (CDCl$_3$) δ 7.35–7.27 (m, 12H), 7.20–7.18 (m, 2H), 5.00 (dd, J=7.9, 8.8 Hz, 1H), 4.81 (d, J=10.7 Hz, 1H), 4.80 (d, J=11.6 Hz, 1H), 4.68 (d, J=11.3 Hz, 1H), 4.59 (d, J=12.5 Hz, 1H), 4.56 (d, J=10.7 Hz, 1H), 4.52 (d, J=12.2 Hz, 1H), 4.30 (d, J=7.9 Hz, 1H), 3.74–3.67 (m, 4H), 3.51–3.37 (m, 4H), 1.99 (s, 3H); $^{13}$C-NMR (CDCl$_3$) δ 169.8, 138.2, 138.0, 136.8, 129.2, 128.7, 128.6, 128.2, 128.1, 128.0, 102.0, 83.2, 78.1, 75.3, 75.2, 73.2, 72.9, 68.9, 56.9, 21.2; FAB MS m/z (M+Na)$^+$: calcd 563.1813, obsd 563.1817.

Methyl 2-O-benzoyl-3,4-di-O-benzyl-6-O-(4-chlorobenzyl)-β-D-glucopyranoside 21.

Methyl 3,4-di-O-benzyl-6-O-(4-chlorobenzyl)-β-D-glucopyranoside (0.244 g, 0.481 mmol) was dissolved in 5 mL CH$_2$Cl$_2$. Benzoyl chloride (67 μL, 0.577 mmol) and DMAP (0.118 g, 0.962 mmol) were added and the reaction mixture was stirred at room temperature for 1 h. A 30% EtOAc/Hexanes solution was added (a white precipitate formed) and the solution was filtered through silica, eluted with EtOAc and concentrated. Purification by flash column chromatography on silica gel (25–30% EtOAc/Hexanes) gave 243 mg (84%) of 21 as a white solid. [α]$^{24}_D$: +33.4° (c 1.29, CH$_2$Cl$_2$); IR (thin film) 2865, 1726, 1268, 1089 cm$^{-1}$; $^1$H-NMR (CDCl$_3$) δ 8.05 (d, J=7.0 Hz, 2H), 7.59 (t, J=7.3 Hz, 1H), 7.46 (t, J=7.9 Hz, 2H), 7.36–7.29 (m, 8H), 7.26–7.21 (m, 2H), 7.15 (s, 4H), 5.30 (dd, J=7.9, 9.2 Hz, 1H), 4.86 (d, J=10.7 Hz, 1H), 4.77 (d, J=11.0 Hz, 1H), 4.70 (d, J=11.0 Hz, 1H), 4.62 (d, J=12.2 Hz, 1H), 4.59 (d, J=11.0 Hz, 1H), 4.56 (d, J=12.5 Hz, 1H), 4.48 (d, J=7.9 Hz, 1H), 3.86 (dd, J=9.2, 9.2 Hz, 1H), 3.80–3.74 (m, 3H), 3.61–3.58

(m, 1H), 3.50 (s, 3H); $^{13}$C-NMR (CDCl$_3$) δ 165.4, 138.0, 137.9, 136.8, 133.5, 133.3, 130.1, 130.0, 129.2, 128.7, 128.6, 128.5, 128.4, 128.2, 128.1, 128.0, 127.8, 102.1, 83.0, 78.1, 75.4, 75.3, 75.2, 73.9, 72.9, 68.9, 57.0; FAB MS m/z (M+Na)$^+$: calcd 625.1969, obsd 625.1973.

Methyl 3,4-di-O-benzyl-2-O-(tert-butyldimethylsilyl)-6-O-(4-chlorobenzyl)-β-D-glucopyranoside 22.

Methyl 3,4-di-O-benzyl-6-O-(4-chlorobenzyl)-β-D-glucopyranoside (0.258 g, 0.517 mmol) was dissolved in 3 mL CH$_2$Cl$_2$. 2,6-lutidine (240 μL, 2.06 mmol) and tert-butyldimethylsilyltrifluoromethane sulfonate (0.284 mL, 1.24 mmol) were added and the reaction mixture was stirred at room temperature for 30 min. The solution was filtered through silica, eluted with EtOAc and concentrated. Purification by flash column chromatography on silica gel (10% EtOAc/Hexanes) gave 283 mg (89%) of 22 as a colorless oil. [α]$^{24}_D$: −9.2° (c 2.01, CH$_2$Cl$_2$); IR (thin film) 2928, 2855, 1492, 1069 cm$^{-1}$; $^1$H-NMR (CDCl$_3$) δ 7.41–7.29 (m, 12H), 7.16–7.13 (m, 2H), 4.97 (d, J=11.3 Hz, 1H), 4.90 (d, J=11.3 Hz, 1H), 4.82 (d, J=11.0 Hz, 1H), 4.61 (d, J=12.5 Hz, 1H), 4.56–4.53 (m, 2H), 4.17 (d, J=7.3 Hz, 1H), 3.78–3.76 (m, 1H), 3.71 (dd, J=4.6, 10.7 Hz, 1H), 3.63–3.53 (m, 6H), 0.95 (s, 9H), 0.17 (s, 3H), 0.13 (s, 3H); $^{13}$C-NMR (CDCl$_3$) δ 138.8, 138.1, 136.8, 133.5, 129.2, 128.6, 128.5, 128.4, 128.3, 128.0, 127.9, 127.5, 104.9, 86.0, 78.3, 75.8, 75.4, 75.1, 74.9, 72.8, 69.1, 57.9, 26.1, 18.4, −4.1, −4.2; FAB MS m/z (M+Na)$^+$: calcd 635.2572, obsd 635.2574.

Methyl 3,4-di-O-benzyl-6-O-(tert-butyldiphenylsilyl)-2-O-(4-chlorobenzyl)-β-D-glucopyranoside 23.

General procedure A using using methyl 3,4-di-O-benzyl-6-O-(tert-butyldiphenylsilyl)-β-D-glucopyranoside (0.124 g, 0.202 mmol), NaH (15 mg, 0.303 mmol, 60% in mineral oil) and 4-chlorobenzylchloride (34.2 mg, 0.212 mmol) and gave 72 mg (48%) of 23 as a colorless oil after purification by flash column chromatography on silica gel (10% EtOAc/Hexanes). [α]$^{24}_D$: +6.9° (c 1.16, CH$_2$Cl$_2$); IR (thin film) 2929, 1492, 1428, 1072 cm$^{-1}$; $^1$H-NMR (CDCl$_3$) δ 7.82 (dd, J=1.5, 7.9 Hz, 2H), 7.76 (dd, J=1.2, 7.9 Hz, 2H), 7.49–7.31 (m, 18H), 7.27–7.24 (m, 2H), 4.97–4.88 (m, 4H), 4.76 (d, J=10.7 Hz, 1H), 4.75 (d, J=11.3 Hz, 1H), 4.37 (d, J=7.6 Hz, 1H), 3.99 (s, 2H), 3.83 (dd, J=9.2, 9.5 Hz, 1H), 3.71 (dd, J=9.2, 9.2 Hz, 1H), 3.64 (s, 3H), 3.49 (dd, J=7.9, 8.8 Hz, 1H), 3.41–3.39 (m, 1H), 1.12 (s, 9H); $^{13}$C-NMR (CDCl$_3$) δ 138.7, 138.4, 137.4, 136.1, 135.8, 135.0, 133.8, 133.5, 133.3, 129.8, 129.5, 128.7, 128.6, 128.1, 128.0, 127.9, 127.8, 104.6, 84.8, 82.7, 77.9, 76.1, 75.8, 75.4, 74.1, 62.8, 56.9, 27.0, 26.8, 19.5; FAB MS m/z (M)+: calcd 759.2885, obsd 759.2881.

Methyl 2-O-pivaloyl-3,4,6-tri-O-benzyl-β-D-glucopyranoside-(1→6)-3,4-di-O-benzyl-2-O-(4-chlorobenzyl)-β-D-glucopyranoside 24.

Glycosyl donor 17 (0.322 g, 0.429 mmol) and methyl 3,4-di-O-benzyl-2-O-(4-chlorobenzyl)-β-D-glucopyranoside (0.179 g, 0.358 mmol) were combined and azeotropically dried with toluene (3×5 mL) followed by 1 h under vacuum. The mixture was dissolved in CH$_2$Cl$_2$ and cooled to −78° C. for 15 min. TMSOTf (79 μL, 0.43 mmol) was added dropwise. After stirring for 10 min at −78° C., triethylamine (100 μL) was added. The solution was warmed to room temperature and the solvent was removed in a stream of N$_2$. The resulting crude product was purified by flash silica column chromatography (20% EtOAc/Hexanes) to afford 0.296 g (82%) of 24 as a colorless oil. [α]$^{24}_D$: +4.2° (c 0.36, CH$_2$Cl$_2$); IR (thin film) 2909, 1740, 1452, 1070 cm$^{-1}$; $^1$H-NMR (CDCl$_3$) δ 7.33–7.23 (m, 27H), 7.16–7.13 (m, 2H), 5.10 (dd, J=7.9, 9.5 Hz, 1H), 4.88–4.74 (m, 5H), 4.69–4.49 (m, 7H), 4.26 (d, J=7.9 Hz, 1H), 4.03 (dd, J=1.5, 11.6 Hz, 1H), 3.77–3.50 (m, 12H), 3.37–3.33 (m, 2H), 1.12 (s, 9H); $^{13}$C-NMR (CDCl$_3$) δ 176.9, 138.7, 138.3, 138.1, 138.0, 137.1, 133.6, 129.6, 128.7 (2 lines), 128.6 (2 lines), 128.3, 128.2, 128.1, 128.0, 127.9, 127.8 (2 lines), 127.5, 104.4, 101.1, 84.7, 83.6, 82.3, 78.4, 78.0, 75.9, 75.6, 75.4, 75.2 (2 lines), 74.0, 73.7, 73.1, 69.0, 67.6, 57.2, 29.9, 27.4; FAB MS m/z (M++H) calcd 1037.4219, obsd 1037.4188.

4-O-(4-Methoxybenzyl)-6-O-triisopropylsilyl-D-arabino-hex-1-enitol 25.

The general procedure B using 19 (0.15 g, 0.250 mmol), N-methylaniline (33 μL, 0.30 mmol), Pd$_2$(dba)$_3$ (2.4 mg, 0.0026 mmol), (o-biphenyl)P(t-Bu)$_2$ (3.0 mg, 0.010 mmol) and NaOtBu (34.0 mg, 0.350 mmol) gave 0.152 g (99%) of aminated product as a yellow oil after purification by flash column chromatography on silica gel (15% EtOAc/Hexanes). Cleavage of the aminated intermediate (54.8 mg, 0.080 mmol) with ZnCl$_2$ (80 μL 1.0 M in Et$_2$O, 0.080 mmol) using general procedure D gave 34.6 mg (97%) of 25 as a colorless oil after purification by flash column chromatography on silica gel (20% EtOAc/Hexanes). [α]$^{24}_D$: +11.4° (c 0.59, CH$_2$Cl$_2$); IR (thin film) 3372, 2940, 2865, 1649, 1514 cm$^{-1}$; $^1$H-NMR (CDCl$_3$) δ 7.31 (d, J=8.5 Hz, 2H), 6.89 (d, J=8.5 Hz, 2H), 6.36 (dd, J=1.2, 6.1 Hz, 1H), 4.76–4.70 (m, 3H), 4.20–4.27 (m, 1H), 4.05 (d, J=2.4 Hz, 2H), 3.86–3.84 (m, 1H), 3.81 (s, 3H), 3.73–3.70 (m, 1H), 2.17 (d, J=5.8 Hz, 1H), 1.13–1.06 (m, 21H); $^{13}$C-NMR (CDCl$_3$) δ 159.6, 144.8, 130.8, 129.8, 114.2, 102.2, 77.9, 76.9, 73.6, 68.4, 62.7, 55.5, 18.2, 18.1, 12.2; FAB MS m/z (M+Na)$^+$: calcd 445.2386, obsd 445.2396.

Methyl 2-O-acetyl-3,4-di-O-benzyl-β-D-glucopyranoside 26.

The general procedure C using 20 (73.1 mg, 0.135 mmol), morpholine (14.1 μL, 0.162 mmol), Pd(OAc)$_2$ (1.2 mg, 0.0054 mmol), 1-(N,N-dimethylamino)-1'-(dicyclohexylphosphino) biphenyl (5.4 mg, 0.0054 mmol) and K$_3$PO$_4$ (40.0 mg, 0.189 mmol) for 12 h at 100° C. afforded a yellow oil. Cleavage of the aminated intermediate with SnCl$_4$ (162 μL 1.0 M in CH$_2$Cl$_2$, 0.162 mmol) using general procedure D gave 49.0 mg (87%) of 26 as a white solid after purification by flash column chromatography on silica gel (50% EtOAc/Hexanes). [α]$^{24}_D$: −23.5° (c 3.24, CH$_2$Cl$_2$); IR (thin film) 3474, 2879, 1747, 1234, 1082 cm$^{-1}$; $^1$H-NMR (CDCl$_3$) δ 7.37–7.26 (m, 10H), 5.00–4.92 (m, 1H), 4.85 (d, J=11.0 Hz, 1H), 4.83 (d, J=11.9 Hz, 1H), 4.69 (d, J=11.0 Hz, 1H), 4.67 (d, J=11.0 Hz, 1H), 4.34 (d, J=7.9 Hz, 1H), 3.92–3.88 (m, 1H), 3.77–3.69 (m, 3H), 3.49 (s, 3H), 3.42–3.40 (m, 1H), 1.98 (s, 3H); $^{13}$C-NMR (CDCl$_3$) δ 169.8, 138.2, 137.9, 128.7, 128.6, 128.2, 128.1, 128.0, 127.9, 102.1, 82.7, 77.7, 75.4, 75.3, 75.2, 73.2, 61.9, 57.1, 21.1; FAB MS m/z (M+Na)$^+$: calcd 439.1733, obsd 439.1730.

Methyl 2-O-benzoyl-3,4-di-O-benzyl-β-D-glucopyranoside 27.

The general procedure C using 21 (70.3 mg, 0.117 mmol), morpholine (12.2 μL, 0.140 mmol), Pd(OAc)$_2$ (1.0 mg, 0.0046 mmol), 1-(N,N-dimethylamino)-1'-(dicyclohexylphosphino) biphenyl (1.8 mg, 0.0046 mmol) and K$_3$PO$_4$ (34.8 mg, 0.164 mmol) for 12 h at 100° C. afforded a yellow oil. Cleavage of the aminated intermediate with SnCl$_4$ (140 μL 1.0 M in CH$_2$Cl$_2$, 0.140 mmol) using general procedure D gave 44.0 mg (79%) of 27 as a colorless oil after purification by flash column chromatography on silica gel (50% EtOAc/Hexanes). [α]$^{24}_D$: −28.1° (c 3.24, CH$_2$Cl$_2$); IR (thin film) 3454, 2878, 1726, 1269, 1086 cm$^{-1}$; $^1$H-NMR (CDCl$_3$) δ 8.04 (d, J=8.2 Hz, 2H), 7.59 (t, J=8.5 Hz, 1H), 7.38–7.32 (m, 4H), 7.15 (s, 4H), 5.26 (dd, J=8.2, 9.4 Hz, 1H), 4.88 (d, J=11.0 Hz, 1H), 4.78 (d, J=11.0 Hz, 1H), 4.70 (d, J=11.0 Hz, 1H), 4.69 (d, J=11.3 Hz, 1H), 4.51 (d, J=7.9 Hz, 1H), 3.96–3.94 (m, 1H), 3.88 (dd, J=9.2, 9.5 Hz, 1H), 3.80–3.75 (m, 2H), 3.51–3.48 (m, 4H), 2.09–2.07 (m, 1H); $^{13}$C-NMR (CDCl$_3$) δ 165.4, 138.0, 137.9, 133.3, 130.0, 128.7, 128.6, 128.5, 128.3, 128.2, 127.9, 102.2, 82.7, 77.8, 75.5, 75.3, 73.9, 62.0, 57.2; FAB MS m/z (M+Na)$^+$: calcd 501.1890, obsd 501.1888.

Methyl 3,4-di-O-benzyl-2-O-(tert-butyldimethylsilyl)-β-D-glucopyranoside 28.

The general procedure C using 22 (0.123 g, 0.20 mmol), N-methylaniline (26 μL, 0.24 mmol), Pd(OAc)$_2$ (0.9 mg, 0.004 mmol), (o-biphenyl)P(t-Bu)$_2$ (2.4 mg, 0.008 mmol) and NaOtBu (26.9 mg, 0.28 mmol) for 12 h at room temperature afforded a yellow oil. Cleavage of the aminated intermediate with ZnCl$_2$ (240 1L 1.0 M in Et$_2$O, 0.240 mmol) using general procedure D gave 78.2 mg (80%) of 28 as a colorless oil after purification by flash column chromatography on silica gel (25% EtOAc/Hexanes). [α]$^{24}_D$: −28.8° (c 1.32, CH$_2$Cl$_2$); IR (thin film) 3475, 2954, 2855, 1071 cm$^{-1}$; $^1$H-NMR (CDCl$_3$) δ 7.38–7.24 (m, 10H), 4.94 (d, J=11.3 Hz, 1H), 4.89 (d, J=11.3 Hz, 1H), 4.82 (d, J=11.0 Hz, 1H), 4.64 (d, J=10.7 Hz, 1H), 4.18 (d, J=7.3 Hz, 1H), 3.91–3.88 (m, 1H), 3.76–3.72 (m, 1H), 3.61–3.49 (m, 6H), 3.42–3.38 (m, 1H), 2.04–2.02 (m, 1H), 0.92 (s, 9H), 0.13 (s, 3H), 0.09 (s, 3H); $^{13}$C-NMR (CDCl$_3$) δ 138.7, 138.1, 128.6, 128.4, 128.2, 128.1, 127.6, 127.5, 105.0, 85.7, 78.0, 75.7, 75.4, 75.2, 62.1, 57.4, 26.1, 18.4, −4.1, −4.2; FAB MS m/z (M+Na)$^+$: calcd 511.2492, obsd 511.2492.

Methyl 3,4-di-O-benzyl-6-O-(tert-butyldiphenylsilyl)-β-D-glucopyranoside 29.

The general procedure C using 23 (56.8 mg, 0.077 mmol), N-methylaniline (10 μL, 0.092 mmol), Pd(OAc)$_2$ (0.7 mg, 0.003 mmol), (o-biphenyl)P(t-Bu)$_2$ (1.8 mg, 0.006 mmol) and NaOtBu (10.4 mg, 0.11 mmol) for 12 h at room temperature afforded a yellow oil. Cleavage of the aminated intermediate with SnCl$_4$ (92 μL 1.0 M in CH$_2$Cl$_2$, 0.092 mmol) using general procedure D gave 38.0 mg (81%) of 29 as a colorless oil after purification by flash column chromatography on silica gel (25% EtOAc/Hexanes). [α]$^{24}_D$: −13.60 (c 6.02, CH$_2$Cl$_2$); IR (thin film) 3456, 3070, 2930, 1113, 1055 cm$^{-1}$; $^1$H-NMR (CDCl$_3$) δ 7.89 (dd, J=0.6, 6.7 Hz, 2H), 7.83 (dd, J=0.9, 6.7 Hz, 2H), 7.54–7.33 (m, 16H), 5.0 (d, J=11.3 Hz, 1H), 5.04 (d, J=11.0 Hz, 1H), 5.01 (d, J=11.0 Hz, 1H), 4.84 (d, J=11.0 Hz, 1H), 4.32 (d, J=7.6 Hz, 1H), 4.10–4.04 (m, 2H), 3.91 (dd, J=9.2, 9.2 Hz, 1H), 3.76–3.67 (m, 5H), 3.51–3.46 (m, 1H), 2.83 (br s, 1H), 1.18 (s, 9H); $^{13}$C-NMR (CDCl$_3$) δ 138.9, 138.4, 136.2, 135.8, 133.9, 133.3, 129.9, 128.8, 128.7, 128.3, 128.2, 128.0, 127.8, 103.8, 84.8, 77.7, 76.2, 75.6, 75.4, 75.0, 62.9, 56.9, 27.0, 19.6; FAB MS m/z (M+Na)$^+$: calcd 635.2805, obsd 635.2804.

Methyl 2-O-pivaloyl-3,4,6-tri-O-benzyl-β-D-glucopyranoside-(1→6)-3,4-di-O-benzyl-β-D-glucopyranoside 30.

General procedure C using methyl 2-O-pivaloyl-3,4,6-tri-O-benzyl-β-D-glucopyranoside-(1→6)-3,4-di-O-benzyl-2-O-(4-chlorobenzyl)-β-D-glucopyranoside (0.202 g, 0.20 mmol), N-methylaniline (26 μL, 0.24 mmol), Pd(OAc)$_2$ (0.9 mg, 0.004 mmol), (o-biphenyl)P(t-Bu)$_2$ (2.4 mg, 0.008 mmol), NaOtBu (27 mg, 0.280 mmol) for 16 h at room temperature gave 0.193 g (89%) aminated product as a yellow oil after purification by flash column chromatography on silica gel (10–20% EtOAc/Hexanes). Cleavage of the aminated intermediate (0.138 g, 0.127 mmol) with SnCl$_4$ (0.13 mL 1.0 M in heptane, 0.13 mmol) using general procedure D gave 0.112 g (99%) of 30 as a white solid after purification by flash column chromatography on silica gel (35% EtOAc/Hexanes). [α]$^{24}_D$: −3.5° (c 0.40, CH$_2$Cl$_2$); IR (thin film) 3454, 2870, 1739, 1453, 1061 cm$^{-1}$; $^1$H-NMR (CDCl$_3$) δ 7.40–7.26 (m, 23H), 7.18–7.16 (m, 2H), 5.13 (dd, J=8.2, 9.2 Hz, 1H), 4.93 (d, J=11.6 Hz, 1H), 4.86 (d, J=10.4 Hz, 2H), 4.78 (d, J=11.0 Hz, 1H), 4.77 (d, J=10.7 Hz, 1H), 4.70 (d, J=11.0 Hz, 1H), 4.63–4.61 (m, 3H), 4.55 (d, J=10.7 Hz, 1H), 4.52 (d, J=11.9 Hz, 1H), 4.17 (d, J=7.6 Hz, 1H), 4.06 (dd, J=1.5, 11.6 Hz, 1H), 3.79–3.75 (m, 4H), 3.69 (dd, J=9.2, 9.2 Hz, 1H), 3.61–3.50 (m 7H), 3.43–3.39 (m, 1H), 2.40 (d, J=2.1 Hz, 1H), 1.22 (s, 9H); $^{13}$C-NMR (CDCl$_3$) δ 176.8, 138.7, 138.3, 138.2, 138.1, 138.0, 128.7, 128.6 (2 lines), 128.5 (2 lines), 128.2, 128.1, 128.0 (2 lines), 127.9, 127.8 (2 lines), 127.5, 103.4, 101.1, 84.5, 83.5, 78.1, 77.9, 75.8, 75.4, 75.3, 75.2, 75.1, 75.0, 74.7, 73.7, 73.0, 68.9, 67.5, 57.3, 39.0, 27.3; FAB MS m/z (M+Na)$^+$: calcd 913.4139, obsd 913.4118.

Incorporation by Reference

All of the patents and publications cited herein are hereby incorporated by reference.

Equivalents

Those skilled in the art will recognize, or be able to ascertain using no more than routine experimentation, many equivalents to the specific embodiments of the invention described herein. Such equivalents are intended to be encompassed by the following claims.

We claim:

1. A compound represented by general structure 53:

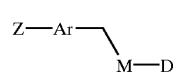

53 wherein

D represents an optionally substituted alllopyranoside, altropyranoside, gulopyranoside, idopyranoside, talopyranoside, arabinofuranoside, or lyxofuranoside;

M represents O, S, or NR;

R represents independently for each occurrence H, alkyl, acyl, aryl or heteroaromatic;

Z represents Cl, Br, or I;

hetereoaromatic represents independently for each occurrence an aromatic group with 5–7 ring atoms, of which one to four are S, O and/or N;

Ar represents a monocyclic or polycyclic aryl or heteroaromatic groups that is optionally substituted with one or more substituents independently selected from the group consisting of halide, alkyl, alkenyl, alkynyl, hydroxyl, amino, nitro, sulfhydryl, —R$_9$SR$_8$, —C(O)N(R$_8$)$_2$, —Q$_2$—P(Q$_1$)R$_8$(OR$_8$), carboxyl, —R$_9$C(O)OC(O)R$_8$, silyl, —SR$_8$, alkylsulfonyl, arylsulfonyl, —R$_9$(O)CR$_8$, —R$_9$C(O)H, —R$_9$C(O)OR, —OC(O)R, heteroalkyl, —R$_9$CN, aryl, monocyclic or bicyclic heteroaromatic, and aralky; wherein CH$_2$MD and Z are bonded to the same aromatic ring of Ar;

R$_8$ represents independently for each occurrence hydrogen, alkyl, alkenyl, alkynyl, or aryl;

R$_9$ represents independently for each occurrence a bond or an alkyl, alkenyl, alkynyl, or aryl biradical;

Q$_1$ represents independently for each occurrence S or O; and

Q$_2$ represents independently for each occurrence O, S, or NR$_8$.

2. The compound of claim 1, wherein Ar represents a phenyl group that is optionally substituted with one or more substituents independently selected from the group consisting of halide, alkyl, alkenyl, alkynyl, hydroxyl, amino, nitro, sulfhydryl, —R$_9$SR$_8$, —C(O)N(R$_8$)$_2$, —Q$_2$—P(Q$_1$)R$_8$(OR$_8$), carboxyl, —R$_9$C(O)OC(O)R$_8$, silyl, —SR$_8$, alkylsulfonyl, arylsulfonyl, —R$_9$(O)CR$_8$, —R$_9$C(O)H, —R$_9$C(O)OR, —OC(O)R, heteroalkyl, —R$_9$CN, aryl, monocyclic or bicyclic heteroaromatic, and aralkyl.

3. The compound of claim 1, wherein M represents O.

4. The compound of claim 1, wherein Z represents Cl or Br.

5. The compound of claim 1, wherein Ar represents a phenyl group that is optionally substituted with one or more substituents independently selected from the group consisting of halide, alkyl, alkenyl, alkynyl, hydroxyl, amino, nitro, sulfhydryl, —$R_9SR_8$, —$C(O)N(R_8)_2$, —$Q_2$—$P(Q_1)R_8(OR_8)$, carboxyl, —$R_9C(O)OC(O)R_8$, silyl, —$SR_8$, alkylsulfonyl, arylsulfonyl, —$R_9(O)CR_8$, —$R_9C(O)H$, —$R_9C(O)OR$, —$OC(O)R$, heteroalkyl, —$R_9CN$, aryl, monocyclic or bicyclic heteroaromatic, and aralkyl; and Z represents Cl or Br.

6. The compound of claim 1, wherein Ar represents a phenyl group that is optionally substituted with one or more substituents independently selected from the group consisting of halide, alkyl, alkenyl, alkynyl, hydroxyl, amino, nitro, sulfhydryl, —$R_9SR_8$, —$C(O)N(R_8)_2$, —$Q_2$—$P(Q_1)R_8(OR_8)$, carboxyl, —$R_9C(O)OC(O)R_8$, silyl, —$SR_8$, alkylsulfonyl, arylsulfonyl, —$R_9(O)CR_8$, —$R_9C(O)H$, —$R_9C(O)OR$, —$OC(O)R$, heteroalkyl, —$R_9CN$, aryl, monocyclic or bicyclic heteroaromatic, and aralkyl; and M represents O.

7. The compound of claim 1, wherein Ar represents a phenyl group that is optionally substituted with one or more substituents independently selected from the group consisting of halide, alkyl, alkenyl, alkynyl, hydroxyl, amino, nitro, sulfhydryl, —$R_9SR_8$, —$C(O)N(R_8)_2$, —$Q_2$—$P(Q_1)R_8(OR_8)$, carboxyl, —$R_9C(O)OC(O)R_8$, silyl, —$SR_8$, alkylsulfonyl, arylsulfonyl, —$R_9(O)CR_8$, —$R_9C(O)H$, —$R_9C(O)OR$, —$OC(O)R$, heteroalkyl, —$R_9CN$, aryl, monocyclic or bicyclic heteroaromatic, and aralkyl; Z represents Cl or Br; and M represents O.

8. A compound selected from the group consisting of:
6-O-(4-iodobenzyl)-1,2:3,4-di-O-isopropylidene-α-D-galactopyranoside;
6-O-(4-bromobenzyl)-1,2:3,4-di-O-isopropylidene-α-D-galactopyranoside;
6-O-(4-chlorobenzyl)-1,2:3,4-di-O-isopropylidene-α-D-galactopyranoside;
6-O-(2-bromobenzyl)-1,2:3,4-di-O-isopropylidene-α-D-galactopyranoside;
6-O-(2-chlorobenzyl)-1,2:3,4-di-O-isopropylidene-α-D-galactopyranoside;
methyl 3,4-di-O-benzyl-6-O-(4-bromobenzyl)-2-O-(4-chlorobenzyl)-β-D-glucopyranoside;
methyl 3,4-di-O-benzyl-2-O-(2-bromobenzyl)-6-O-(4-bromobenzyl)-β-D-glucopyranoside;
methyl 3,4-di-O-benzyl-6-O-(4-chlorobenzyl)-β-D-glucopyranoside;
methyl 3,4-di-O-benzyl-2-O-(2-bromobenzyl)-6-O-(4-chlorobenzyl)-β-D-glucopyranoside;
methyl 3,4-di-O-benzyl-2-O-(2-chlorobenzyl)-6-O-(4-chlorobenzyl)-β-D-glucopyranoside;
methyl 3,4-di-O-benzyl-6-O-(4-(N-benzylamino)benzyl)-2-O-(4-chlorobenzyl)-β-D-glucopyranoside;
methyl 3,4-di-O-benzyl-2-O-(4-chlorobenzyl)-β-D-glucopyranoside;
methyl 2-O-pivaloyl-3,4,6-tri-O-benzyl-β-D-glucopyranoside-(1→6)-3,4-di-O-benzyl-2-O-(4-chlorobenzyl)-β-D-glucopyranoside;
methyl 3,4-di-O-benzyl-6-O-(4-bromobenzyl)-2-O-(2-(N-morpholino)benzyl)-β-D-glucopyranoside;
methyl 3,4-di-O-benzyl-6-O-(4-(N-morpholino)benzyl)-2-O-(2-bromobenzyl)-β-D-glucopyranoside;
methyl 6-O-benzyl-3-O-(4-bromobenzyl)-4-O-(4-chlorobenzyl)-2-O-(4-iodobenzyl)-β-D-glucopyranoside;
methyl 6-O-benzyl-3-O-(4-bromobenzyl)-4-O-(4-chlorobenzyl)-β-D-glucopyranoside;
methyl [2,3,4,6-tetra-O-benzyl-α-D-mannopyranoside-(1→2)]-6-O-benzyl-3-O-(4-bromobenzyl)-4-O-(4-chlorobenzyl)-β-D-glucopyranoside;
methyl [2,3,4,6-tetra-O-benzyl-α-D-mannopyranoside-(1→2)]-6-O-benzyl-4-O-(4-chlorobenzyl)-β-D-glucopyranoside;
methyl [2,3,4,6-tetra-O-benzyl-α-D-mannopyranoside-(1→2)]-3-O-propyl-6-O-benzyl-4-O-(4-chlorobenzyl)-β-D-glucopyranoside;
methyl 2-O-acetyl-3,4-di-O-benzyl-6-O-(4-chlorobenzyl)-β-D-glucopyranoside;
methyl 2-O-benzoyl-3,4-di-O-benzyl-6-O-(4-chlorobenzyl)-β-D-glucopyranoside;
methyl 3,4-di-O-benzyl-2-O-(tert-butyldimethylsilyl)-6-O-(4-chlorobenzyl)-β-D-glucopyranoside;
methyl 3,4-di-O-benzyl-6-O-(tert-butyldiphenylsilyl)-2-O-(4-chlorobenzyl)-β-D-glucopyranoside; and
methyl 2-O-pivaloyl-3,4,6-tri-O-benzyl-β-D-glucopyranoside-(1→6)-3,4-di-O-benzyl-2-O-(4-chlorobenzyl)-β-D-glucopyranoside.

9. A compound reDresented by structure 54:

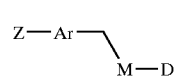

54 wherein

D represents an optionally substituted glucopyranoside, galactopyranoside, ribofuranoside, or xylofuranoside;

M represents O, S, or NR;

R represents independently for each occurrence H, alkyl, acyl, aryl or heteroaromatic;

Z represents Br or I;

hetereoaromatic represents independently for each occurrence an aromatic group with 5–7 ring atoms, of which one to four are S, O and/or N;

Ar represents a monocyclic or polycyclic aryl or heteroaromatic group that is optionally substituted with one or more substituents independently selected from the group consisting of halide, alkyl, alkenyl, alkynyl, hydroxyl, amino, nitro, sulfhydryl, —$R_9SR_8$, —$C(O)N(R_8)_2$, —$Q_2$—$P(Q_1)R_8(OR_8)$, carboxyl, —$R_9C(O)OC(O)R_8$, silyl, —$SR_8$, alkylsulfonyl, arylsulfonyl, —$R_9(O)CR_8$, —$R_9C(O)H$, —$R_9C(O)OR$, —$OC(O)R$, heteroalkyl, —$R_9CN$, aryl, monocyclic or bicyclic heteroaromatic, and aralkyl; wherein $CH_2MD$ and Z are bonded to the same aromatic ring of Ar;

$R_8$ represents independently for each occurrence hydrogen, alkyl, alkenyl, alkynyl, or aryl;

$R_9$ represents independently for each occurrence a bond or an alkyl, alkenyl, alkynyl, or aryl biradical;

$Q_1$ represents independently for each occurrence S or O; and $Q_2$ represents independently for each occurrence O, S, or $NR_8$.

10. A compound represented by structure 55:

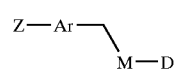

55 wherein

D represents an optionally substituted mannopyranoside;

M represents O, S, or NR;

R represents independently for each occurrence H, alkyl, acyl, aryl or heteroaromatic;

Z represents Cl or I;

hetereoaromatic represents independently for each occurrence an aromatic group with 5–7 ring atoms, of which one to four are S, O and/or N;

Ar represents a monocyclic or polycyclic aryl or heteroaromatic group that is optionally substituted with one or more substituents independently selected from the group consisting of halide, alkyl, alkenyl, alkynyl, hydroxyl, amino, nitro, sulfhydryl, —$R_9SR_8$, —C(O)N($R_8$)$_2$, —$Q_2$—P($Q_1$)$R_8$(O$R_8$), carboxyl, —$R_9$C(O)OC(O)$R_8$, silyl, —$SR_8$, alkylsulfonyl, arylsulfonyl, —$R_9$(O)C$R_8$, —$R_9$C(O)H, —$R_9$C(O)OR, —OC(O)R, heteroalkyl, —$R_9$CN, aryl, monocyclic or bicyclic heteroaromatic, and aralkyl; wherein $CH_2MD$ and Z are bonded to the same aromatic ring of Ar;

$R_8$ represents independently for each occurrence hydrogen, alkyl, alkenyl, alkynyl, or aryl;

$R_9$ represents independently for each occurrence a bond or an alkyl, alkenyl, alkynyl, or aryl biradical;

$Q_1$ represents independently for each occurrence S or O; and $Q_2$ represents independently for each occurrence O, S, or $NR_8$.

\* \* \* \* \*

UNITED STATES PATENT AND TRADEMARK OFFICE
CERTIFICATE OF CORRECTION

| | | |
|---|---|---|
| PATENT NO. | : 6,693,178 B2 | Page 1 of 1 |
| APPLICATION NO. | : 10/146711 | |
| DATED | : February 17, 2004 | |
| INVENTOR(S) | : Stephen L. Buchwald et al. | |

It is certified that error appears in the above-identified patent and that said Letters Patent is hereby corrected as shown below:

Column 1, lines 15-18, replace:

"This invention was made with support provided by the National Institutes of Health (Grant Number GM 58160). Therefore, the government has certain rights in the invention."

with

--This invention was made with government support under Grant No. R01 GM058160, awarded by the National Institutes of Health. The government has certain rights in this invention.--

Signed and Sealed this
Sixth Day of September, 2011

David J. Kappos
*Director of the United States Patent and Trademark Office*